US012617759B2

(12) United States Patent
Su et al.

(10) Patent No.: US 12,617,759 B2
(45) Date of Patent: May 5, 2026

(54) MODIFIER OF FOUR-MEMBERED RING DERIVATIVE, PREPARATION METHOD AND APPLICATION THEREOF

(71) Applicants: Shanghai Hansoh Biomedical Co., Ltd., Shanghai (CN); Jiangsu Hansoh Pharmaceutical Group Co., Ltd., Lianyungang (CN)

(72) Inventors: Yidong Su, Shanghai (CN); Xiaofeng Mao, Shanghai (CN); Kailong Li, Shanghai (CN); Jun Wang, Shanghai (CN); Jiaqiang Cai, Shanghai (CN); Rudi Bao, Shanghai (CN)

(73) Assignees: Shanghai Hansoh Biomedical Co., Ltd., Shanghai (CN); Jiangsu Hansoh Pharmaceutical Group Co., Ltd., Lianyungang (CN)

( * ) Notice: Subject to any disclaimer, the term of this patent is extended or adjusted under 35 U.S.C. 154(b) by 1042 days.

(21) Appl. No.: 17/754,837

(22) PCT Filed: Oct. 29, 2020

(86) PCT No.: PCT/CN2020/124609
§ 371 (c)(1),
(2) Date: Apr. 13, 2022

(87) PCT Pub. No.: WO2021/083246
PCT Pub. Date: May 6, 2021

(65) Prior Publication Data

US 2023/0076435 A1 Mar. 9, 2023

(30) Foreign Application Priority Data

Oct. 29, 2019 (CN) ......................... 201911039123.5
Jan. 10, 2020 (CN) ......................... 202010028151.3
Jul. 24, 2020 (CN) ......................... 202010725922.4

(51) Int. Cl.

| | |
|---|---|
| ***C07D 241/04*** | (2006.01) |
| ***A61P 25/18*** | (2006.01) |
| ***C07D 401/12*** | (2006.01) |
| ***C07D 403/12*** | (2006.01) |
| ***C07D 405/12*** | (2006.01) |
| ***C07D 409/04*** | (2006.01) |
| ***C07D 413/12*** | (2006.01) |
| ***C07D 417/12*** | (2006.01) |

(52) U.S. Cl.
CPC ............ *C07D 241/04* (2013.01); *A61P 25/18* (2018.01); *C07D 401/12* (2013.01); *C07D 403/12* (2013.01); *C07D 405/12* (2013.01); *C07D 409/04* (2013.01); *C07D 413/12* (2013.01); *C07D 417/12* (2013.01)

(58) Field of Classification Search
None
See application file for complete search history.

(56) References Cited

U.S. PATENT DOCUMENTS

| | | | |
|---|---|---|---|
| 9,376,396 | B2 | 6/2016 | Haupt et al. |
| 9,388,148 | B2 | 7/2016 | Haupt et al. |
| 2014/0194437 | A1 | 7/2014 | Haupt |
| 2014/0303176 | A1 | 10/2014 | Haupt et al. |

FOREIGN PATENT DOCUMENTS

| | | | |
|---|---|---|---|
| CN | 104854103 | A | 8/2015 |
| CN | 105339357 | A | 2/2016 |
| WO | WO-2005012266 | A1 | 2/2005 |
| WO | WO-2007093540 | A1 | 8/2007 |
| WO | WO-2009013212 | A2 | 1/2009 |
| WO | WO-2010031735 | A1 | 3/2010 |
| WO | WO-2012117001 | A1 | 9/2012 |
| WO | WO-2014086098 | A1 | 6/2014 |
| WO | WO-2020156312 | A1 | 8/2020 |
| WO | WO-2021083246 | A1 | 5/2021 |

OTHER PUBLICATIONS

"International Application No. PCT/CN2020/124609, International Search Report and Written Opinion mailed Jan. 4, 2021", (Jan. 4, 2021), 13 pgs.

Belliotti, Thomas R., et al., "Novel Cyclohexyl Amides as Potent and Selective D3 Dopamine Receptor Ligands", Bioorganic & Medicinal Chemistry Letters, vol. 7, No. 18, (Sep. 23, 1997), 2403-2407.

*Primary Examiner* — Samantha L Shterengarts

(74) *Attorney, Agent, or Firm* — Foley Hoag LLP; Dana M. Gordon; Alexander J. J. Chatterley D.

(57) ABSTRACT

Provided is a modifier of a four-membered ring derivative, a preparation method and application thereof. In particular, provided is a compound represented by the general formula (IX-A), a preparation method thereof, a pharmaceutical composition containing the compound, and a use thereof as a G protein-coupled receptor modulator in the treatment or prevention of central nervous system diseases and/or mental diseases. The definition of each substituents in the general formula (IX-A) is same as the definition in the specification.

(IX-A)

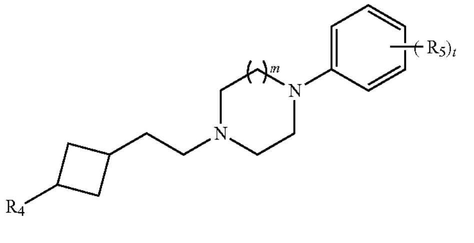

20 Claims, No Drawings

MODIFIER OF FOUR-MEMBERED RING DERIVATIVE, PREPARATION METHOD AND APPLICATION THEREOF

PRIORITY CLAIM TO RELATED APPLICATIONS

This application is a U.S. national stage filing under 35 U.S.C. § 371 from International Application No. PCT/CN2020/124609, filed on 29 Oct. 2020, which claims priority to Chinese Application No. 201911039123.5, filed on 29 Oct. 2019, and to Chinese Application No. 202010028151.3, filed on 10 Jan. 2020, and to Chinese Application No. 202010725922.4, filed on 24 Jul. 2020. This application incorporates by reference the entirety of International Application No. PCT/CN2020/124609 and its published version WO2021/083246 (published 6 May 2021).

FIELD OF THE INVENTION

The present invention belongs to the field of drug synthesis, and specifically relates to a four-membered ring derivative inhibitor, a method for preparing the same, and a use thereof.

BACKGROUND OF THE INVENTION

Dopamine D3 receptor is a member of the G protein-coupled receptor family, and is a subtype of the dopamine receptor. It belongs to D2-like inhibitory receptor along with dopamine D2 and D4 receptors. Upon binding to DA, it reduces cAMP level by inhibiting G-protein. D3 receptors are mainly distributed in the mesolimbic system, especially the nucleus accumbens, olfactory tubercle and calleja's islets which are not related to motor function. Highly active D3 receptor modulators may have good anti-schizophrenia activity. D3 receptor is closely related to mood, cognition, spirit, addiction, etc., and can improve the negative symptoms of schizophrenia patients. D3 receptor may play a regulatory role in cognition by regulating the release of acetylcholine and regulating glutamate receptor. Partial agonism of the D3 receptor can improve cognition.

5-Hydroxytryptamine 2A (5-HT2A) receptor is a member of the G protein-coupled receptor family, and is a major excitatory receptor subtype of the 5-HT receptor. They are distributed in the center and periphery, and are closely related to spirit, emotion, learning, memory, etc. Highly active 5-HT2A receptor inhibitors have significant anti-schizophrenia effects, and can reduce the side effects of extrapyramidal symptoms.

Schizophrenia is a mental illness with the highest prevalence, with a slow course of disease, is prone to repeated attacks, aggravation or exacerbation, resulting in serious burden and adverse consequences for patients and their families. Psychopaths may experience positive symptoms such as delusion, hallucination and disturbance in thought, language and behavior, negative symptoms such as lack of emotion and expression, poor speech and lack of pleasure, and other symptoms such as cognitive disorder. Although the research, development and clinical application of anti-schizophrenia drugs have developed greatly in the past few decades, both traditional antipsychotics (first-generation) (haloperidol, droperidol, thioridazine, etc.) and atypical antipsychotics (second-generation) (clozapine, risperidone, olanzapine, aripiprazole, etc.) are effective in treating positive symptoms, while poor in improving negative symptoms and cognitive disorder. Therefore, there is an urgent need to develop anti-schizophrenia drugs that can improve not only positive symptoms but also negative symptoms and cognitive disorder. Highly active dopamine D3 receptor modulators can improve negative symptoms, positive symptoms and cognitive disorder in patients with schizophrenia, without the side effects of the first- and second-generation antipsychotics such as extrapyramidal symptoms and weight gain.

Antagonists or partial agonists of D3 receptor have a good efficacy on improving the positive symptoms, negative symptoms and cognitive disorder of schizophrenia. International patent applications WO2007093540, WO2009013212A2, WO2010031735A1 and WO2012117001A1 report D3 receptor and $5HT_{2A}$ dual modulator compounds, but most of the binding activities Ki of the compounds to D3 receptor and $5HT_{2A}$ are above 10 nM. Patent application WO2014086098A1 filed by Jiangsu Hengyi Pharmaceutical Co., LTD reports D3 selective inhibitors, but no study on the binding activity to $5HT_{2A}$ is reported. Cariprazine, a D3 antagonist developed by Gedeon Richter Plc., was available in 2015 and applied for the international patent application WO2005012266A1. Cariprazine has a potent D3 receptor agonist activity, and its use in the treatment of schizophrenia for negative symptoms has significant advantages over existing drugs. However, Cariprazine has weak inhibitory activity on $5\text{-}HT_{2A}$ receptor, resulting in severe side effects of extrapyramidal symptoms (ESP). Therefore, there is an urgent need to develop highly active D3 receptor modulators with optimized $5HT_{2A}$ binding activity to reduce the side effects of extrapyramidal symptoms and improve the effects on negative symptoms and cognitive improvement in schizophrenia.

SUMMARY OF THE INVENTION

All content involved in patent application PCT/CN2020/073153 is incorporated into the present invention by way of reference.

The objective of the present invention is to provide a compound of formula (IX-A), a stereoisomer thereof or a pharmaceutically acceptable salt thereof, wherein the structure of the compound of formula (IX-A) is as follows:

(IX-A)

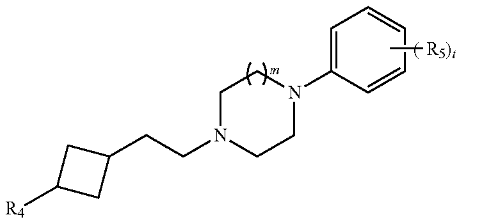

wherein:

$R_4$ is selected from the group consisting of 5 to 6 membered N-containing heterocyclyl

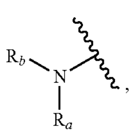

,

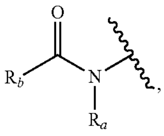

,

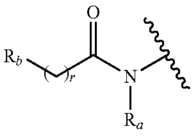

,

-continued

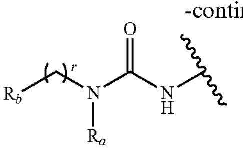

and

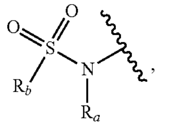

the 5 to 6 membered N-containing heterocyclyl is preferably an oxazolidinonyl;

$R_a$ is selected from the group consisting of hydrogen, deuterium, halogen, amino, nitro, hydroxy, cyano, $C_{1-6}$ alkyl, $C_{1-6}$ deuterated alkyl, $C_{1-6}$ haloalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl;

$R_b$ is selected from the group consisting of hydrogen, deuterium, halogen, amino, nitro, hydroxy, cyano, $C_{1-6}$ alkyl, $C_{1-6}$ deuterated alkyl, $C_{1-6}$ haloalkyl, $C_{1-6}$ alkoxy, $C_{1-6}$ hydroxyalkyl, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl, wherein the amino, $C_{1-6}$ alkyl, $C_{1-6}$ deuterated alkyl, $C_{1-6}$ haloalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl are each optionally further substituted by one or more substituents selected from the group consisting of hydrogen, deuterium, halogen, amino, nitro, hydroxy, cyano, $C_{1-6}$ alkyl, $C_{1-6}$ deuterated alkyl, $C_{1-6}$ haloalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl;

$R_5$ is selected from the group consisting of hydrogen, deuterium, $C_{1-6}$ alkyl, $C_{1-6}$ deuterated alkyl, $C_{1-6}$ haloalkyl, $C_{1-6}$ alkoxy, $C_{1-6}$ haloalkoxy, halogen, amino, nitro, hydroxy, cyano, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl;

preferably selected from the group consisting of hydrogen, cyano, halogen, $C_{1-3}$ alkyl, $C_{1-3}$ haloalkyl, $C_{1-3}$ alkoxy and $C_{3-6}$ cycloalkyl;

and more preferably selected from the group consisting of hydrogen and chlorine;

or, any adjacent two $R_5$ are bonded to form a 5 to 6 membered heterocyclyl or 5 to 6 membered heteroaryl;

preferably a 5 to 6 membered heteroaryl containing 1 to 2 N, S or O heteroatoms; and more preferably thienyl;

r is 0, 1 or 2;

m is 0 or 1; and t is 0, 1, 2 or 3; and preferably 2.

The present invention also provides a preferred embodiment, as for the compound of formula (IX-A), the stereoisomer thereof or the pharmaceutically acceptable salt thereof, when

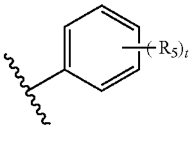

is

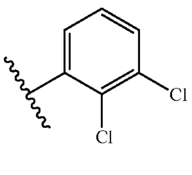

and m is 1, then $R_4$ is not

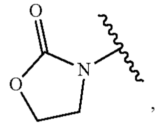

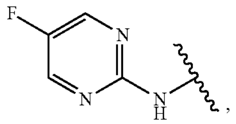

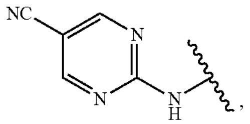

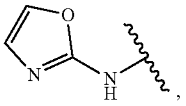

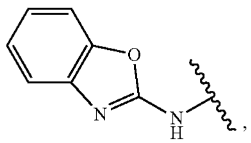

$-NHC(O)C_2H_5$, $-NHC(O)N(CH_3)_2$, $-NHC(O)NHCH_3$, $-NHC(O)NC_2H_5CH_3$, $-NHC(O)NHC_2H_5$,

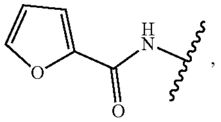

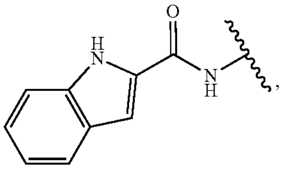

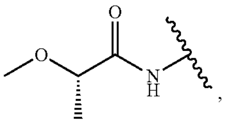

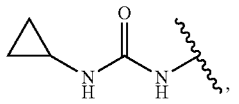

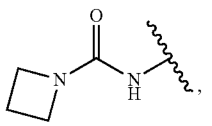

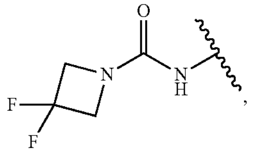

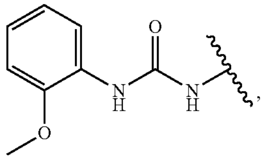

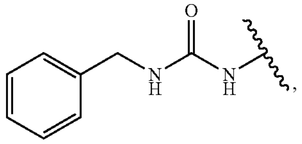

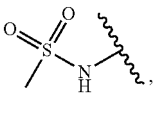

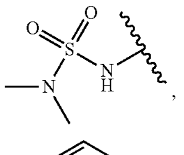

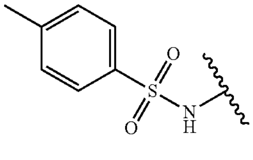

or

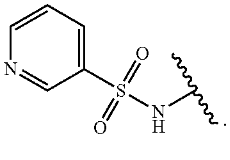

The present invention also provides a preferred embodiment, the compound, the stereoisomer thereof or the pharmaceutically acceptable salt thereof, wherein the compound is as shown in formula (X) or formula (X-A):

(X)

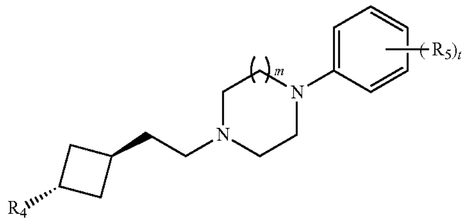

(X-A)

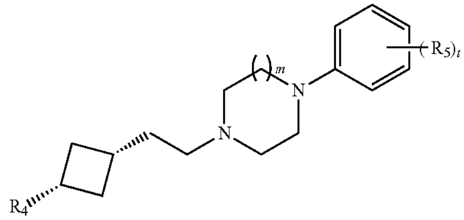

wherein:

$R_4$ and m are as defined in formula (IX-A).

In a further preferred embodiment of the present invention, $R_4$ is selected from the group consisting of 5 to 6 membered N-containing heterocyclyl,

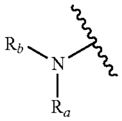, 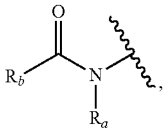, 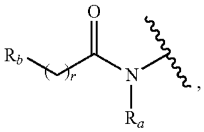,

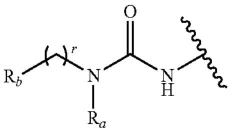 and 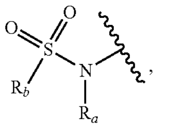, the 5 to 6 membered N-containing heterocyclyl is preferably an oxazolidinonyl;

$R_a$ is selected from the group consisting of hydrogen, deuterium, halogen, amino, nitro, hydroxy, cyano, $C_{1-6}$ alkyl, $C_{1-6}$ deuterated alkyl, $C_{1-6}$ haloalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl;

preferably, $R_a$ is selected from the group consisting of hydrogen, cyano, halogen, $C_{1-3}$ alkyl, $C_{1-3}$ haloalkyl, $C_{1-3}$ alkoxy and $C_{3-6}$ cycloalkyl;

and more preferably, $R_a$ is selected from the group consisting of hydrogen and methyl;

$R_b$ is selected from the group consisting of hydrogen, deuterium, halogen, amino, nitro, hydroxy, cyano, $C_{1-6}$ alkyl, $C_{1-6}$ deuterated alkyl, $C_{1-6}$ haloalkyl, $C_{1-6}$ alkoxy, $C_{1-6}$ hydroxyalkyl, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl, wherein the amino, $C_{1-6}$ alkyl, $C_{1-6}$ deuterated alkyl, $C_{1-6}$ haloalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl are each optionally further substituted by one or more substituents selected from the group consisting of hydrogen, deuterium, halogen, amino, nitro, hydroxy, cyano, $C_{1-6}$ alkyl, $C_{1-6}$ deuterated alkyl, $C_{1-6}$ haloalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl;

preferably, R is selected from the group consisting of amino, $C_{1-3}$ alkyl, $C_{1-3}$ alkoxy, $C_{1-3}$ hydroxyalkyl, $C_{3-6}$ cycloalkyl, 3 to 6 membered heterocyclyl, $C_{6-10}$ aryl and 5 to 10 membered heteroaryl, wherein the amino, $C_{1-3}$ alkyl, $C_{1-3}$ alkoxy, $C_{1-3}$ hydroxyalkyl, $C_{3-6}$ cycloalkyl, 3 to 6 membered heterocyclyl, $C_{6-10}$ aryl and 5 to 10 membered heteroaryl are each optionally further substituted by one or more substituents selected from the group consisting of hydrogen, halogen, hydroxy, cyano, $C_{1-3}$ alkyl and $C_{1-3}$ alkoxy;

and more preferably, $R_b$ is selected from the group consisting of amino, methyl, ethyl, methoxy, hydroxyisopropyl, cyclopropyl, azetidinyl, phenyl, pyridyl, furanyl, pyrimidinyl, oxazolyl, thiazolyl, isoxazolyl, indolyl, quinolyl and benzoxazolyl, wherein the amino, methyl, ethyl, methoxy, hydroxyisopropyl, cyclopropyl, azetidinyl, phenyl, pyridyl, furanyl, pyrimidinyl, oxazolyl, thiazolyl, isoxazolyl, indolyl, quinolyl and benzoxazolyl are each optionally further substituted by one or more substituents selected from the group consisting of hydrogen, fluorine, cyano, hydroxy, methyl and methoxy; and r is 0, 1 or 2.

The present invention also provides a preferred embodiment, the compound, the stereoisomer thereof or the pharmaceutically acceptable salt thereof, wherein the formula (IX-A) is as shown in formula (XI):

(XI)

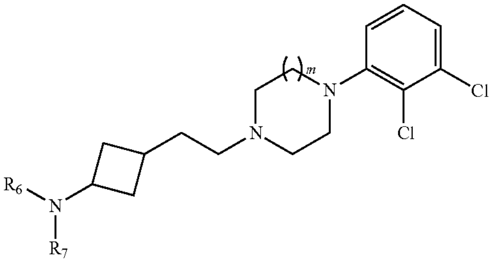

wherein:

$R_6$ is selected from the group consisting of hydrogen, deuterium, $C_{1-6}$ alkyl, $C_{1-6}$ deuterated alkyl, $C_{1-6}$ haloalkyl, $C_{1-6}$ alkoxy, $C_{1-6}$ haloalkoxy, halogen, amino, nitro, hydroxy, cyano, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl;

$R_7$ is selected from the group consisting of hydrogen, deuterium, halogen, amino, nitro, hydroxy, cyano, $C_{1-6}$ alkyl, $C_{1-6}$ deuterated alkyl, $C_{1-6}$ haloalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl, 5 to 12 membered heteroaryl, $R_{ee}$, $-C(O)(CH_2)_{n2}R_{ee}$, $-(CH_2)_{n2}C(O)NR_{ee}R_{ff}$, $-C(O)NR_{ee}R_{ff}$, $-(CH_2)_{n2}C(O)NR_{ee}C(O)R_{ff}$, $-(CH_2)_{n2}S(O)_{m2}R_{ee}$, $-(CH_2)_{n2}NR_{ee}S(O)_{m2}R_{ff}$, $-(CH_2)_{n2}S(O)_{m2}NR_{ee}R_{ff}$, $-(CH_2)_{n1}S(O)_{m2}NR_{ee}R_{ff}$, $-(CH_2)_{n2}OR_{ee}$, $-C(O)NR_{ee}(CH_2)_{n2}R_{ff}$, $-C(O)(CH_2)_{n2}OR_{ee}$, $-(CH_2)_{n2}SR_{ee}$, $-(CH_2)_{n2}C(O)OR_{ee}$, $-P(O)R_{ee}R_{ff}$, $-(CH_2)_{n2}NR_{ee}C(O)R_{ff}$ and $-(CH_2)_{n2}NR_{ee}S(O)_{m2}R_{ff}$, wherein the $C_{1-6}$ alkyl, $C_{1-6}$ deuterated alkyl, $C_{1-6}$ haloalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl are each optionally further substituted by one or more substituents selected from the group consisting of deuterium, halogen, amino, nitro, hydroxy, cyano, $C_{1-6}$ alkyl, $C_{1-6}$ deuterated alkyl, $C_{1-6}$ haloalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl; and preferably selected from the group consisting of 5 to 10 membered heteroaryl, $R_{ee}$, $—C(O)(CH_2)_{n2}R_{ee}$, $—C(O)NR_{ee}R_{ff}$, $—C(O)NR_{ff}(CH_2)_{n2}R_{ee}$, $—S(O)_{m2}R_{ee}$ and $—S(O)_{m2}NR_{ee}R_{ff}$;

$R_{ee}$ and $R_{ff}$ are each independently selected from the group consisting of hydrogen, amino, $C_{1-6}$ alkyl, $C_{1-6}$ haloalkyl, $C_{1-6}$ alkoxy, $C_{3-8}$ cycloalkyl, 3 to 8 membered heterocyclyl, $C_{6-14}$ aryl and 5 to 14 membered heteroaryl, wherein the amino, $C_{1-6}$ alkyl, $C_{1-6}$ haloalkyl, $C_{1-6}$ alkoxy, $C_{3-8}$ cycloalkyl, 3 to 8 membered heterocyclyl, $C_{6-14}$ aryl and 5 to 14 membered heteroaryl are each optionally further substituted by one or more substituents selected from the group consisting of hydrogen, halogen, hydroxy, cyano, oxo, $C_{1-6}$ alkyl, $C_{1-6}$ haloalkyl and $C_{1-6}$ alkoxy;

preferably, $R_{ee}$ and $R_{ff}$ are each independently selected from the group consisting of amino, $C_{1-6}$ alkyl, $C_{1-6}$ hydroxyalkyl, $C_{3-6}$ cycloalkyl, phenyl, naphthyl, biphenyl, 4 to 6-membered heterocyclyl containing 1 to 2 nitrogen atoms and 5 to 10 membered heteroaryl containing 1 to 2 oxygen, nitrogen, sulfur atoms, wherein the amino, $C_{1-6}$ alkyl, $C_{1-6}$ hydroxyalkyl, $C_{3-6}$ cycloalkyl, phenyl, naphthyl, biphenyl, 4 to 6-membered heterocyclyl containing 1 to 2 nitrogen atoms and 5 to 10 membered heteroaryl containing 1 to 2 oxygen, nitrogen, sulfur atoms are each optionally substituted by one or more substituents selected from the group consisting of halogen, hydroxy, cyano, oxo, $C_{1-6}$ alkyl and $C_{1-6}$ alkoxy;

and more preferably, $R_{ee}$ and $R_{ff}$ are each independently selected from the group consisting of:

$(CH_3)_2N—$, $CH_3NH—$, $CH_3—$, $CH_3CH_2—$, $CH_3CH_2NH—$, $CH_3CH_2NCH_3—$, $(CH_3)_2COH—$, $(CH_3)_2COHCH_2—$, $CH_3OCH_2—$,

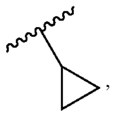, 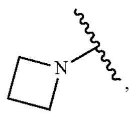, 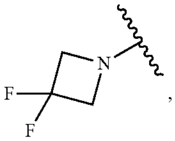, 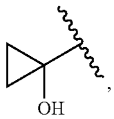, 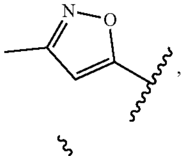, 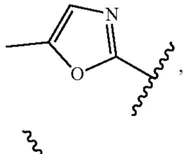, 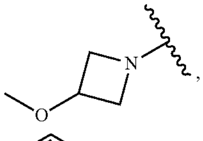, 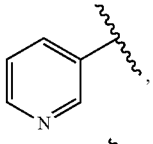, 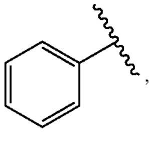, 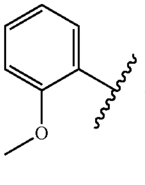, 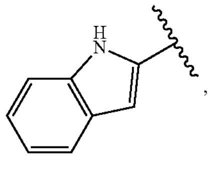, 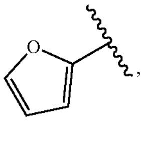, -continued

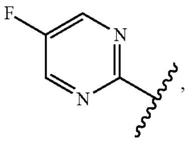, 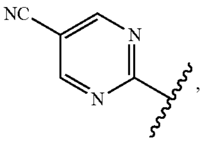, 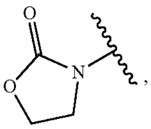, 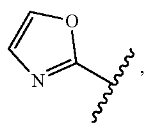, 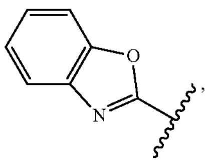, 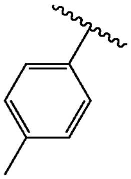, 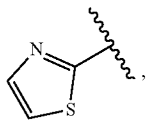, 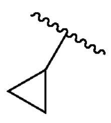 and 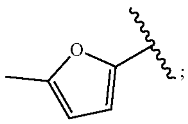;

n2 is selected from the group consisting of 0, 1 and 2;

m2 is selected from the group consisting of 0, 1 and 2; and m is selected from the group consisting of 0, 1 and 2.

In a further preferred embodiment of the present invention, $R_{ee}$ and $R_{ff}$ are each independently selected from the group consisting of hydrogen and the following substituents:

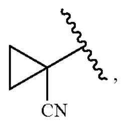, 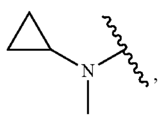, 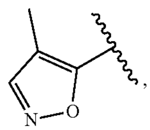, 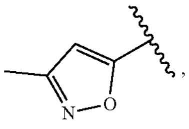, 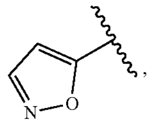, 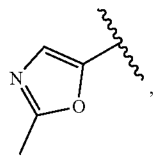, 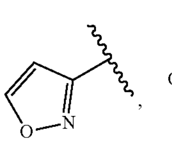, 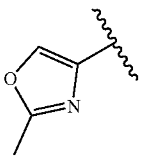 and 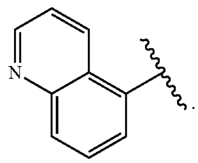.

The present invention also provides a preferred embodiment, the compound, the stereoisomer thereof or the pharmaceutically acceptable salt thereof, wherein the formula (XI) is as shown in formula (XI-A) or formula (XI-B):

(XI-A)

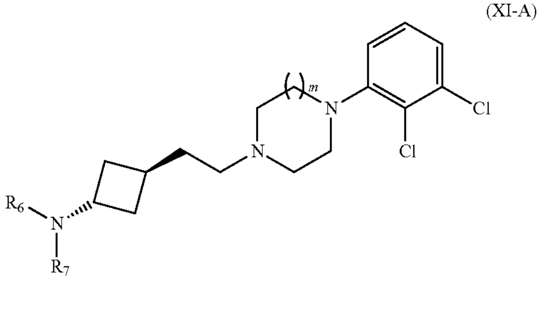

-continued (XI-B)

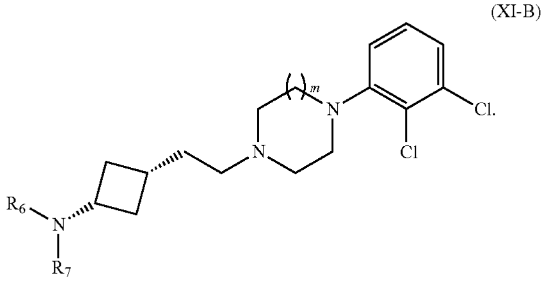

In a preferred embodiment of the present invention, $R_6$ is selected from the group consisting of hydrogen, deuterium, halogen, amino, nitro, hydroxy, cyano, $C_{1-3}$ alkyl, $C_{1-3}$ deuterated alkyl, $C_{1-3}$ haloalkyl, $C_{1-3}$ alkoxy, $C_{1-3}$ haloalkoxy, $C_{2-3}$ alkenyl and $C_{2-3}$ alkynyl; and preferably hydrogen;

$R_7$ is selected from the group consisting of $R_{ee}$, —C(O)$(CH_2)_{n2}R_{ee}$, —C(O)$NR_{ee}R_{ff}$, —C(O)$NR_{ff}(CH_2)_{n2}R_{ee}$, —$S(O)_{m2}R_{ee}$ and —$S(O)_{m2}NR_{ee}R_{ff}$;

$R_{ee}$ is selected from the group consisting of hydrogen, amino, $C_{1-6}$ alkyl, $C_{1-6}$ haloalkyl, $C_{1-6}$ alkoxy, $C_{3-8}$ cycloalkyl, 3 to 8 membered heterocyclyl, $C_{6-14}$ aryl and 5 to 14 membered heteroaryl, wherein the amino, $C_{1-6}$ alkyl, $C_{1-6}$ haloalkyl, $C_{1-6}$ alkoxy, $C_{3-8}$ cycloalkyl, 3 to 8 membered heterocyclyl, $C_{6-14}$ aryl and 5 to 14 membered heteroaryl are each optionally further substituted by one or more substituents selected from the group consisting of halogen, hydroxy, cyano, oxo, $C_{1-6}$ alkyl, $C_{1-6}$ haloalkyl and $C_{1-6}$ alkoxy;

preferably, $R_{ee}$ is selected from the group consisting of amino, $C_{1-6}$ alkyl, $C_{1-6}$ hydroxyalkyl, $C_{3-6}$ cycloalkyl, phenyl, naphthyl, biphenyl, 4 to 6-membered heterocyclyl containing 1 to 2 oxygen, nitrogen, sulfur heteroatoms and 5 to 10 membered heteroaryl containing 1 to 2 oxygen, nitrogen, sulfur heteroatoms, wherein the amino, $C_{1-6}$ alkyl, $C_{1-6}$ hydroxyalkyl, $C_{3-6}$ cycloalkyl, phenyl, naphthyl, biphenyl, 4 to 6-membered heterocyclyl containing 1 to 2 oxygen, nitrogen, sulfur heteroatoms and 5 to 10 membered heteroaryl containing 1 to 2 oxygen, nitrogen, sulfur heteroatoms are each optionally substituted by one or more substituents selected from the group consisting of halogen, hydroxy, cyano, oxo, $C_{1-6}$ alkyl and $C_{1-6}$ alkoxy;

and more preferably, $R_{ee}$ is selected from the group consisting of: $(CH_3)_2N$—, $CH_3NH$—, $CH_3$—, $CH_3CH_2$—, $CH_3CH_2NH$—, $CH_3CH_2NCH_3$—, $(CH_3)_2C(OH)$—, $(CH_3)_2C(OH)CH_2$—, $CH_3OCH_2$—,

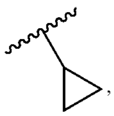,
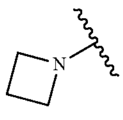,
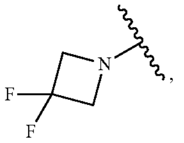,
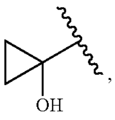,
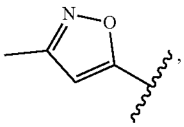,
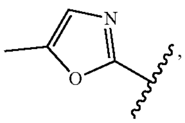,
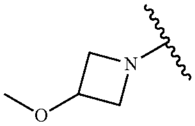,
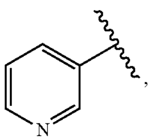,
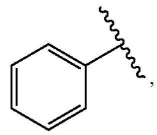, -continued

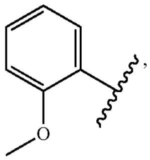,
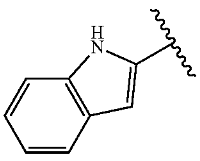,
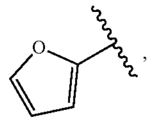,
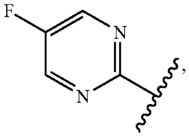,
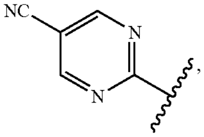,
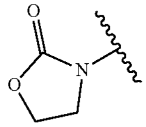,
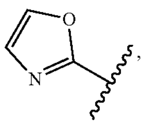,
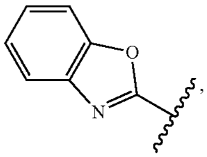,
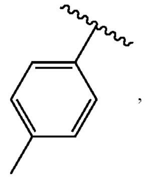,
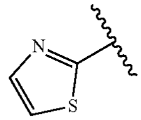,
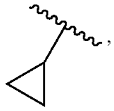,
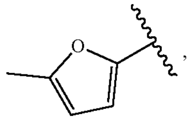,
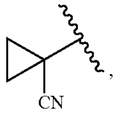,
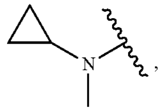,
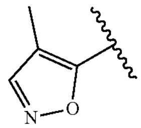,
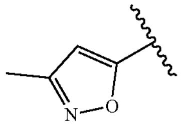,
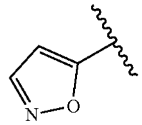,
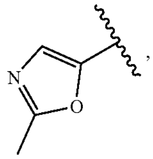,
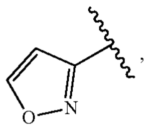,
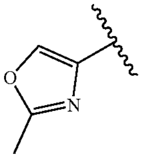 and
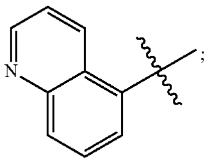;

$R_{ff}$ is selected from the group consisting of hydrogen, deuterium, halogen, amino, nitro, hydroxy, cyano, $C_{1-6}$ alkyl, $C_{1-6}$ deuterated alkyl, $C_{1-6}$ haloalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl;

preferably, $R_{ff}$ is selected from the group consisting of hydrogen, cyano, halogen, $C_{1-3}$ alkyl, $C_{1-3}$ haloalkyl, $C_{1-3}$ alkoxy and $C_{3-6}$ cycloalkyl;

and more preferably, $R_{ff}$ is selected from the group consisting of hydrogen and methyl;

n2 is selected from the group consisting of 0, 1 and 2; and m2 is selected from the group consisting of 0, 1 and 2.

The present invention also provides a preferred embodiment, the compound, the stereoisomer thereof or the pharmaceutically acceptable salt thereof, characterized in that

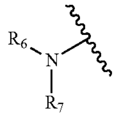

is selected from the group consisting of

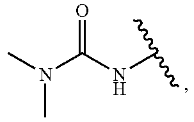
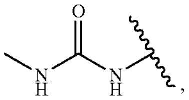
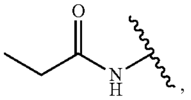
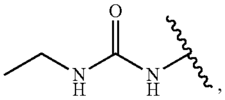
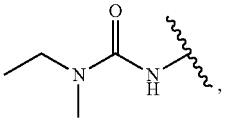
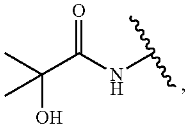
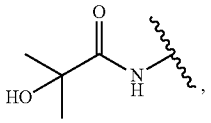
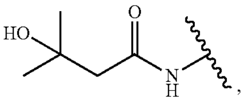
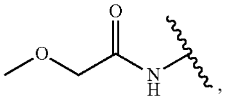
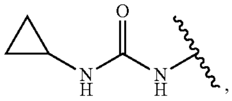
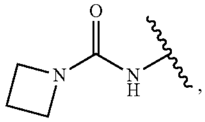
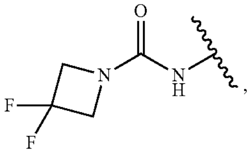
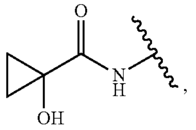
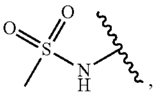
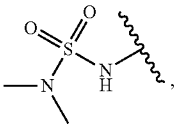
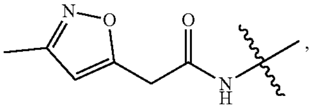
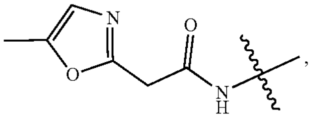
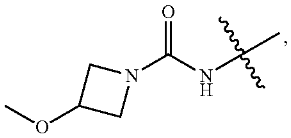
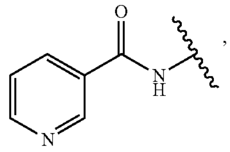
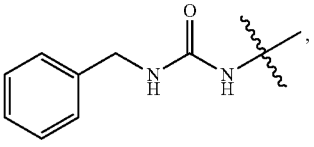
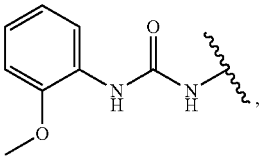
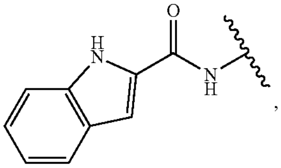
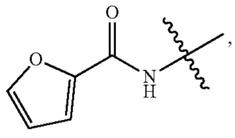
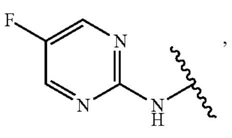

-continued

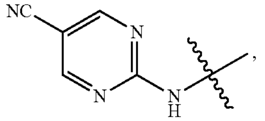
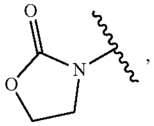
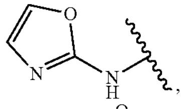
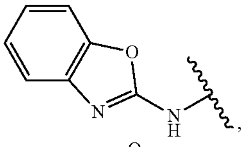
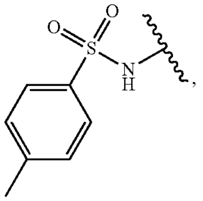
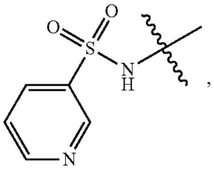
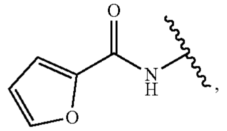
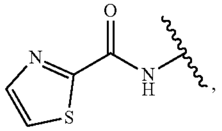
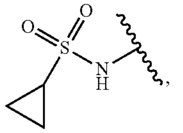
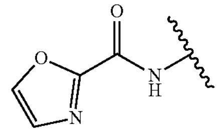

and

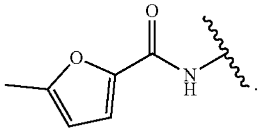

The present invention also provides a preferred embodiment, the compound, the stereoisomer thereof or the pharmaceutically acceptable salt thereof, wherein the formula (XI) is as shown in formula (XII):

(XII)

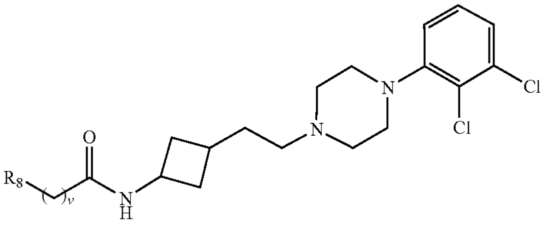

wherein:

$R_8$ is selected from the group consisting of hydrogen, deuterium, halogen, amino, nitro, hydroxy, cyano, $C_{1-6}$ alkyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl, wherein the amino, $C_{1-6}$ alkyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl are each optionally further substituted by one or more substituents selected from the group consisting of hydrogen, deuterium, halogen, amino, nitro, hydroxy, cyano, $C_{1-6}$ alkyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl;

preferably selected from the group consisting of amino, $C_{1-3}$ alkyl, $C_{1-3}$ hydroxyalkyl, $C_{3-6}$ cycloalkyl, 3 to 6 membered heterocyclyl, $C_{6-10}$ aryl and 5 to 10 membered heteroaryl, wherein the amino, $C_{1-3}$ alkyl, $C_{1-3}$ hydroxyalkyl, $C_{3-6}$ cycloalkyl, 3 to 6 membered heterocyclyl, $C_{6-10}$ aryl and 5 to 10 membered heteroaryl are each optionally further substituted by one or more substituents selected from the group consisting of hydrogen, hydroxy, cyano, $C_{1-3}$ alkyl and $C_{1-3}$ alkoxy;

and further selected from the group consisting of: $CH_3O—$, $HOC(CH_3)_2—$,

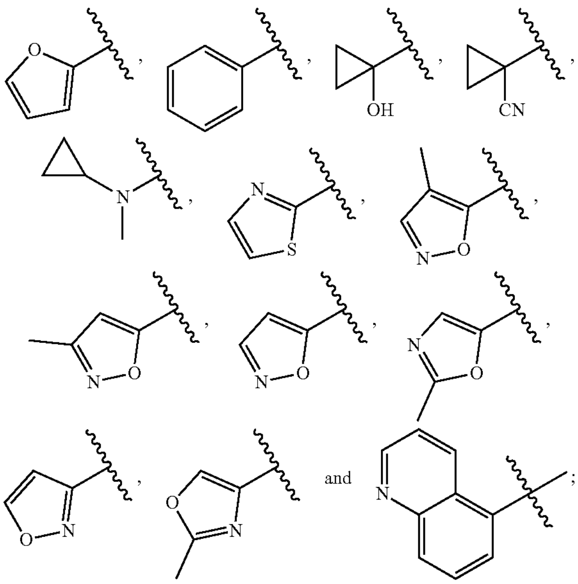

and v is 0 or 1.

The present invention also provides a preferred embodiment, the compound, the stereoisomer thereof or the pharmaceutically acceptable salt thereof, wherein the formula (XI) is as shown in formula (XII):

(XII)

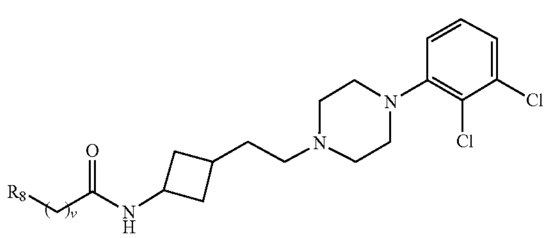

wherein:

$R_8$ is selected from the group consisting of hydrogen, deuterium, halogen, amino, nitro, hydroxy, cyano, $C_{1-6}$ alkyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl, wherein the amino, $C_{1-6}$ alkyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl are each optionally further substituted by one or more substituents selected from the group consisting of deuterium, halogen, amino, nitro, hydroxy, cyano, $C_{1-6}$ alkyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl;

preferably selected from the group consisting of amino, $C_{1-3}$ alkyl, $C_{1-3}$ hydroxyalkyl, $C_{3-6}$ cycloalkyl, 3 to 6 membered heterocyclyl, $C_{6-10}$ aryl and 5 to 10 membered heteroaryl, wherein the amino, $C_{1-3}$ alkyl, $C_{1-3}$ hydroxyalkyl, $C_{3-6}$ cycloalkyl, 3 to 6 membered heterocyclyl, $C_{6-10}$ aryl and 5 to 10 membered heteroaryl are each optionally further substituted by one or more substituents selected from the group consisting of hydroxy, cyano, $C_{1-3}$ alkyl, $C_{1-3}$ alkoxy and $C_{3-6}$ cycloalkyl;

and further selected from the group consisting of: $CH_3O—$, $HOC(CH_3)_2—$,

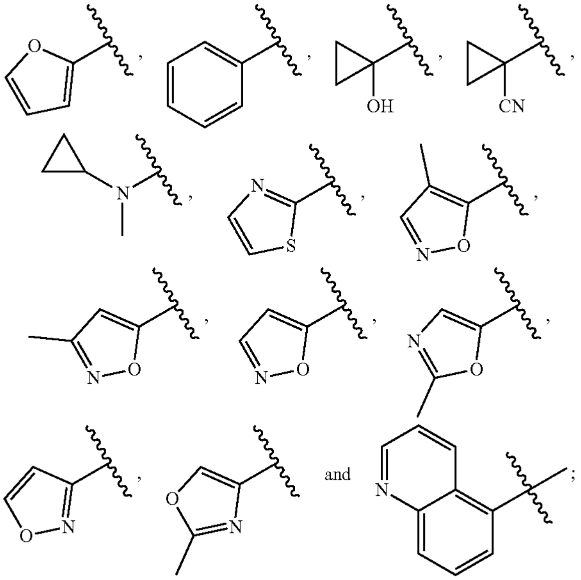

and v is 0 or 1.

The present invention also provides a preferred embodiment, the compound of formula (XII), the stereoisomer thereof or the pharmaceutically acceptable salt thereof, when v is 0, then $R_8$ is not $—C_2H_5$, $—N(CH_3)_2$, $—NHCH_3$, $—NC_2H_5CH_3$, $—NHC_2H_5$,

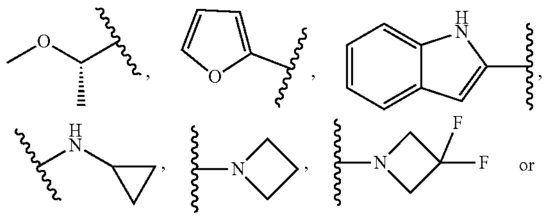

or

-continued

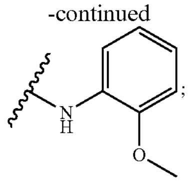;

when v is 1, then $R_8$ is not phenyl.

The present invention also provides a preferred embodiment, the compound, the stereoisomer thereof or the pharmaceutically acceptable salt thereof, wherein the formula (XII) is as shown in formula (XII-A) or formula (XII-B):

(XII-A)

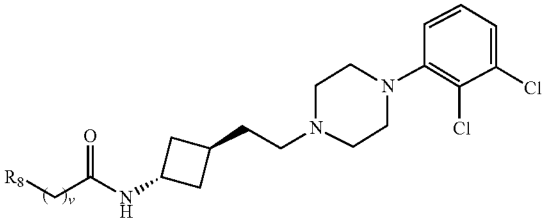

or (XII-B)

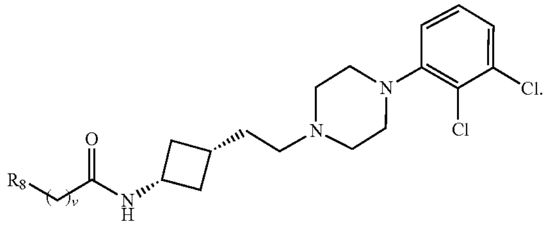

The present invention also provides a preferred embodiment, the compound of formula (IX-A), the stereoisomer thereof or the pharmaceutically acceptable salt thereof, wherein:

$R_4$ is

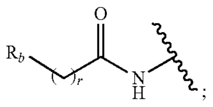;

$R_b$ is selected from the group consisting of $C_{3-6}$ cycloalkyl and 5 to 10 membered heteroaryl containing 1 to 2 nitrogen, oxygen, sulfur atoms, optionally further substituted by one or more substituents selected from the group consisting of deuterium, halogen, amino, hydroxy, $C_{1-3}$ alkyl, $C_{1-3}$ haloalkyl, $C_{1-3}$ alkoxy and $C_{1-3}$ haloalkoxy;

$R_5$ is selected from the group consisting of hydrogen, halogen and $C_{1-3}$ alkyl;

m is 1;

t is 1, 2 or 3.

The present invention also provides a preferred embodiment, the compound of formula (IX-A), the stereoisomer thereof or the pharmaceutically acceptable salt thereof, when r is 0 and $R_b$ is

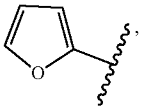, then $R_b$ is substituted by at least one substituent;

when r is 0 and $R_b$ is

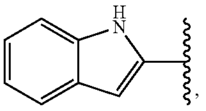 [SMILES: *c1cc2ccccc2[nH]1], then $R_b$ is substituted by at least one substituent.

The present invention also provides a more preferred embodiment, the compound of formula (IX-A), the stereoisomer thereof or the pharmaceutically acceptable salt thereof, wherein:

$R_b$ is selected from the group consisting of $C_{3-6}$ cycloalkyl, 5 to 10 membered heteroaryl containing nitrogen or oxygen and 9 to 10 membered fused heteroaryl containing nitrogen, optionally further substituted by one or more substituents selected from the group consisting of deuterium, halogen, $C_{1-3}$ alkyl, $C_{1-3}$ haloalkyl, $C_{1-3}$ alkoxy and $C_{1-3}$ haloalkoxy;

$R_5$ is selected from the group consisting of hydrogen, halogen, methyl and ethyl.

The present invention also provides a more preferred embodiment, the compound of formula (IX-A), the stereoisomer thereof or the pharmaceutically acceptable salt thereof, wherein:

$R_b$ is selected from the group consisting of cyclopropyl, pyridyl, furanyl, thiazolyl, oxazolyl, isoxazolyl and quinolyl, optionally further substituted by one or more substituents selected from the group consisting of halogen, $C_{1-3}$ alkyl and $C_{1-3}$ haloalkyl.

The compound of the present invention not only has a potent D3 receptor agonistic activity, but also has significantly better inhibitory activity on 5-HT2A than Cariprazine, leading to a good clinical efficacy in treating negative symptoms of schizophrenia and significant reduction of the risk of EPS side effects.

The present invention also relates to a method for preparing the compound of formula (XII), the stereoisomer thereof or the pharmaceutically acceptable salt thereof, comprising the following step of:

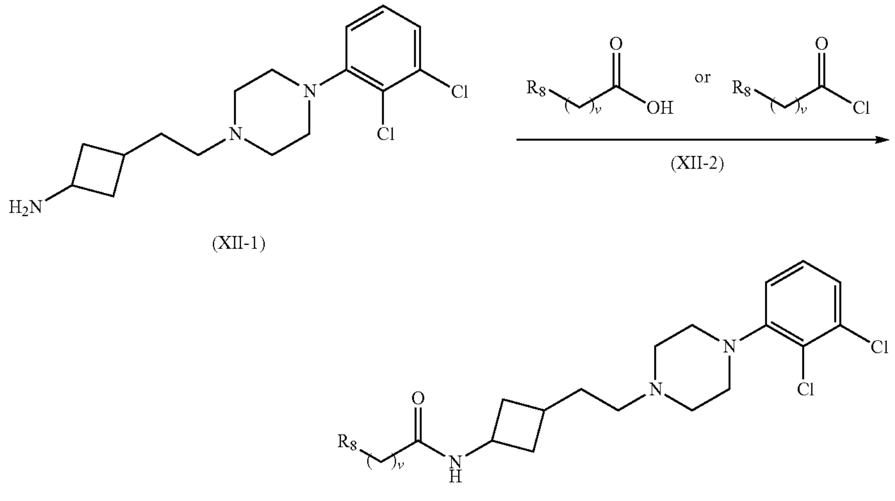

(XII-2)

(XII-1)

(XII)

reacting a compound of formula (XII-1) with an acyl chloride or carboxylic acid of formula (XII-2) to obtain the compound of formula (XII), the stereoisomer thereof or the pharmaceutically acceptable salt thereof.

The present invention also relates to a compound of formula (XII-1), a stereoisomer thereof or a pharmaceutically acceptable salt thereof, (XII-1)

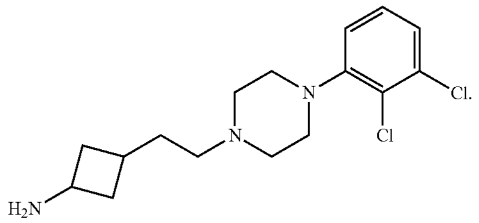

The present invention also relates to a method for preparing the compound of formula (XII-1), the stereoisomer thereof or the pharmaceutically acceptable salt thereof, comprising the following step of,

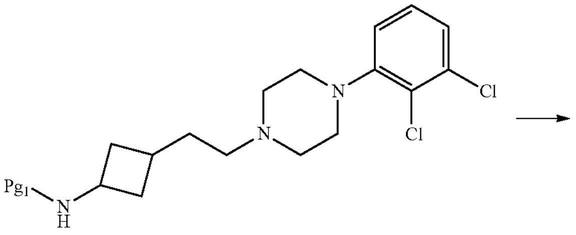

(XII-3)

-continued

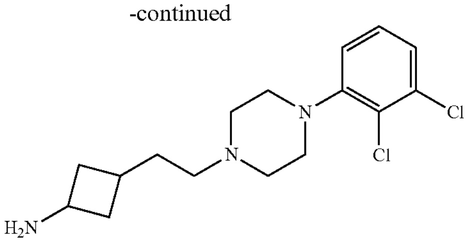

(XII-1)

deprotecting a compound of formula (XII-3) to obtain the compound of formula (XII-1), the stereoisomer thereof or the pharmaceutically acceptable salt thereof, wherein:

$Pg_1$ is an amino protecting group, selected from the group consisting of allyloxycarbonyl (Alloc), trifluoroacetyl, 2,4-dimethoxybenzyl, nitrobenzenesulfonyl, trityl, fluorenemethoxycarbonyl (FMOC), p-toluenesulfonyl (Tos), formate, acetyl, benzyloxycarbonyl (Cbz), tert-butoxycarbonyl (Boc), benzyl (Bn) and p-methoxyphenyl (PMP), and preferably tert-butoxycarbonyl (Boc).

The present invention also relates to a method for preparing the intermediate compound of formula (XII-3), the stereoisomer thereof or the pharmaceutically acceptable salt thereof, comprising the following step of,

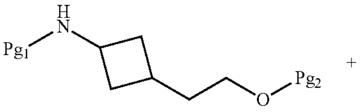

(XII-4)

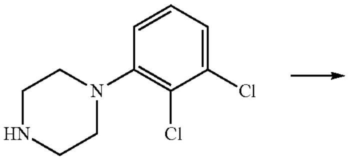

(XII-5)

-continued

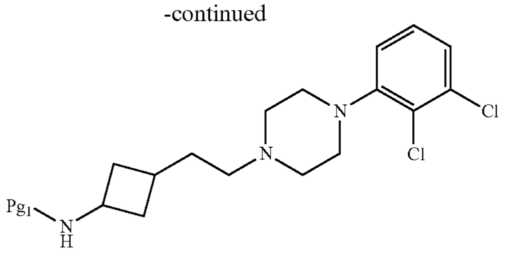

(XII-3)

reacting a compound of formula (XII-4) with a compound of formula (XII-5) to obtain the compound of formula (XII-3), the stereoisomer thereof or the pharmaceutically acceptable salt thereof;

wherein:

$Pg_2$ is a hydroxy protecting group, selected from the group consisting of methyl (—$CH_3$), tert-butyl (—$C(CH_3)_3$), triphenyl (—$CPh_3$), methylthiomethyl ether (MTM), 2-methoxyethoxymethyl ether (MEM), methoxymethyl ether (MOM), p-methoxybenzyl ether (PMB), pivaloyl (Piv), benzyl ether group (—$CH_2Ph$), methoxymethyl (—$CH_2OCH_3$), trimethylsilyl (—$Si(CH_3)_3$), tetrahydrofuranyl (-THP), tert-butyldisilyl (—$SiMe_2$(t-Bu)), acetyl (—Ac), benzoyl (—COPh) and p-toluenesulfonyl (—$SO_2PhMe$), and preferably p-toluenesulfonyl.

The present invention also relates to a pharmaceutical composition, comprising a therapeutically effective dose of the compound of the general formula, the specific compounds, the stereoisomer thereof or the pharmaceutically acceptable salt thereof as described above, and one or more pharmaceutically acceptable carriers, diluents or excipients.

The present invention also relates to a use of the compound of the general formula, the specific compounds, the stereoisomer thereof or the pharmaceutically acceptable salt thereof as described above, or the pharmaceutical composition as described above in the preparation of a G protein-coupled receptor modulator medicament, particularly a dopamine D3 receptor modulator medicament and 5-HT2A receptor modulator medicament.

The present invention further relates to a method for treating an inflammatory disease by the compound of formula (IX-A), the stereoisomer thereof or the pharmaceutically acceptable salt thereof or the pharmaceutical composition thereof.

The present invention also relates to a method for treating and/or preventing a central nervous system disease and/or psychiatric disease or disorder, comprising a step of administering to a patient a therapeutically effective dose of the compound of formula (IX-A), the stereoisomer thereof or the pharmaceutically acceptable salt thereof or the pharmaceutical composition thereof.

The present invention also provides a method for treating a disease condition by using the compound or pharmaceutical composition according to the present invention, wherein the disease condition includes but is not limited to a condition related to a dopamine receptor modulator and 5-HT2A receptor modulator.

The present invention also relates to a method for treating a nervous system disease and/or psychiatric disease in a mammal, comprising a step of administering to the mammal a therapeutically effective amount of the compound or the pharmaceutically acceptable salt, ester, prodrug, solvate, hydrate or derivative thereof according to the present invention.

In some embodiments, the method involves the treatment of conditions such as cancer, bone disease, inflammatory disease, immune disease, neurological disease, metabolic disease, respiratory disease and heart disease.

In some embodiments, the method involves the treatment and/or prevention of a central nervous system disease and/or psychiatric disease or disorder selected from the group consisting of schizophrenia, depression, sleep disorder, mood disorder, schizophrenia spectrum disorder, spastic disorder, memory disorder and/or cognitive disorder, movement disorder, personality disorder, autism spectrum disorder, pain, traumatic brain injury, vascular disease, substance abuse disorder and/or withdrawal syndrome, tinnitus, depression, autism, senile dementia, Alzheimer's disease, seizures, neuralgia, drug withdrawal symptomatic major depressive disorder and mania.

The treatment method provided herein comprises a step of administering to a subject a therapeutically effective amount of the compound of the present invention. In an embodiment, the present invention provides a method for treating a nervous system disease and/or psychiatric disease in a mammal. The method comprises a step of administering to the mammal a therapeutically effective amount of the compound or the pharmaceutically acceptable salt, ester, prodrug, solvate, hydrate or derivative thereof according to the present invention.

Definitions

Unless otherwise stated, the terms used in the specification and claims have the meanings described below.

The term "alkyl" refers to a saturated aliphatic hydrocarbon group, which is a straight or branched chain group comprising 1 to 20 carbon atoms, preferably an alkyl having 1 to 8 carbon atoms, more preferably an alkyl having 1 to 6 carbon atoms, and most preferably an alkyl having 1 to 3 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. More preferably, the alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. The alkyl group can be substituted or unsubstituted. When substituted, the substituent group(s) can be substituted at any available connection point. The substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl. The alkyl of the present invention is preferably selected from the group consisting of methyl, ethyl, isopropyl, tert-butyl, haloalkyl, deuterated alkyl, alkoxy-substituted alkyl and hydroxy-substituted alkyl.

The term “alkylene” refers to an alkyl of which a hydrogen atom is further substituted, for example, “methylene” refers to $—CH_2—$, “ethylene” refers to $—(CH_2)_2—$, “propylene” refers to $—(CH_2)_3—$, “butylene” refers to $—(CH_2)_4—$ and the like. The term “alkenyl” refers to an alkyl as defined above that consists of at least two carbon atoms and at least one carbon-carbon double bond, for example, ethenyl, 1-propenyl, 2-propenyl, 1-, 2- or 3-butenyl and the like. The alkenyl group can be substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio and heterocyclylthio.

The term “cycloalkyl” refers to a saturated or partially unsaturated monocyclic or polycyclic hydrocarbon substituent group having 3 to 20 carbon atoms, preferably 3 to 12 carbon atoms, more preferably 3 to 8 carbon atoms, and most preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Polycyclic cycloalkyl includes a cycloalkyl having a spiro ring, fused ring or bridged ring. The cycloalkyl is preferably cyclopropyl, cyclobutyl, cyclohexyl, cyclopentyl and cycloheptyl, and more preferably cyclopropyl, cyclobutyl and cyclohexyl.

The term “spiro cycloalkyl” refers to a 5 to 20 membered polycyclic group with individual rings connected through one shared carbon atom (called a spiro atom), wherein the rings can contain one or more double bonds, but none of the rings has a completely conjugated π-electron system. The spiro cycloalkyl is preferably a 6 to 14 membered spiro cycloalkyl, and more preferably a 7 to 10 membered spiro cycloalkyl. According to the number of the spiro atoms shared between the rings, the spiro cycloalkyl can be divided into a mono-spiro cycloalkyl, a di-spiro cycloalkyl, or a poly-spiro cycloalkyl, and the spiro cycloalkyl is preferably a mono-spiro cycloalkyl or di-spiro cycloalkyl, and more preferably a 4-membered/4-membered, 4-membered/5-membered, 4-membered/6-membered, 5-membered/5-membered, or 5-membered/6-membered mono-spiro cycloalkyl. Non-limiting examples of spiro cycloalkyl include:

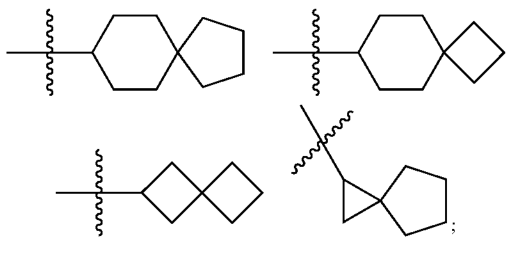
;

and also include spiro cycloalkyl in which a cycloalkyl and a heterocyclyl are connected through one spiro atom, non-limiting examples thereof include:

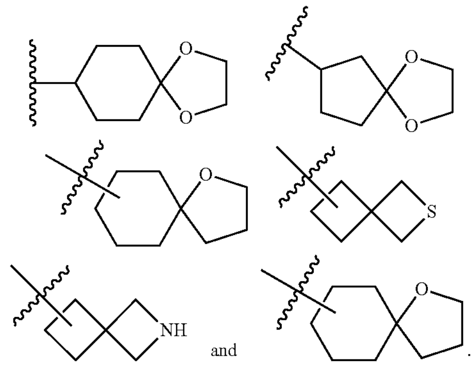
and .

The term “fused cycloalkyl” refers to a 5 to 20 membered all-carbon polycyclic group, wherein each ring in the system shares an adjacent pair of carbon atoms with another ring, one or more rings can contain one or more double bonds, but none of the rings has a completely conjugated π-electron system. The fused cycloalkyl is preferably a 6 to 14 membered fused cycloalkyl, and more preferably a 7 to 10 membered fused cycloalkyl. According to the number of membered rings, the fused cycloalkyl can be divided into a bicyclic, tricyclic, tetracyclic or polycyclic fused cycloalkyl, and the fused cycloalkyl is preferably a bicyclic or tricyclic fused cycloalkyl, and more preferably a 4-membered/4-membered, 5-membered/5-membered or 5-membered/6-membered bicyclic fused cycloalkyl. Non-limiting examples of fused cycloalkyl include:

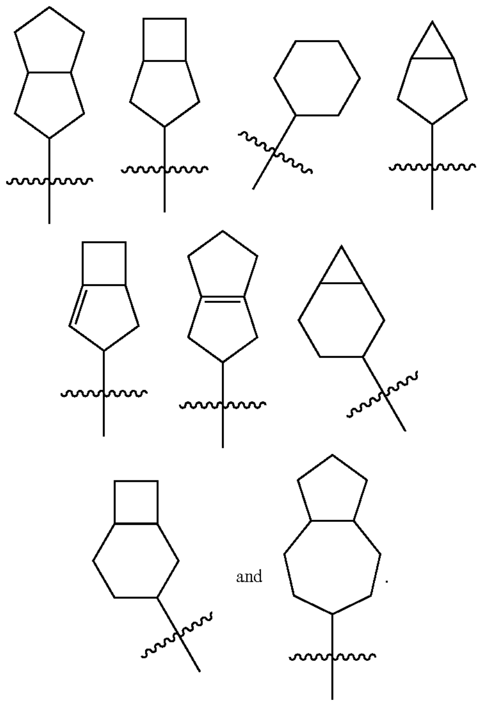
and .

The term “bridged cycloalkyl” refers to a 5 to 20 membered all-carbon polycyclic group, wherein every two rings in the system share two disconnected carbon atoms, the rings can have one or more double bonds, but none of the rings has a completely conjugated π-electron system. The bridged cycloalkyl is preferably a 6 to 14 membered bridged cycloalkyl, and more preferably a 7 to 10 membered bridged cycloalkyl. According to the number of membered rings, the bridged cycloalkyl can be divided into a bicyclic, tricyclic, tetracyclic or polycyclic bridged cycloalkyl, and the bridged cycloalkyl is preferably a bicyclic, tricyclic or tetracyclic bridged cycloalkyl, and more preferably a bicyclic or tricyclic bridged cycloalkyl. Non-limiting examples of bridged cycloalkyl include:

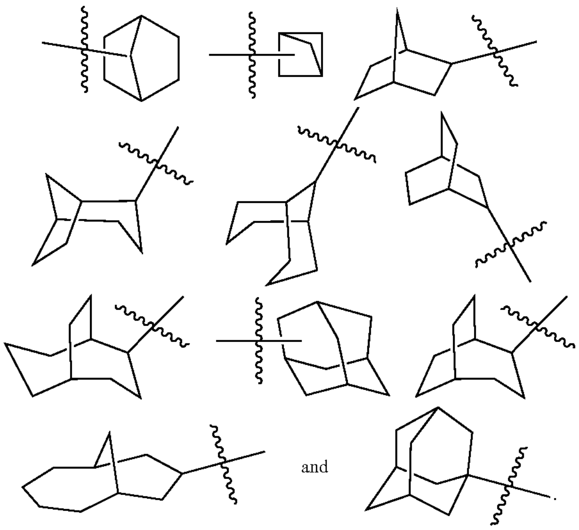

and

The cycloalkyl ring can be fused to the ring of aryl, heteroaryl or heterocyclyl, wherein the ring bound to the parent structure is cycloalkyl. Non-limiting examples include indanyl, tetrahydronaphthyl, benzocycloheptyl and the like. The cycloalkyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl.

The term "heterocyclyl" refers to a 3 to 20 membered saturated or partially unsaturated monocyclic or polycyclic hydrocarbon group, wherein one or more ring atoms are heteroatoms selected from the group consisting of nitrogen, oxygen, boron, phosphorus, $S(O)_m$ (wherein m is an integer of 0 to 2) and $P(O)_n$ (wherein n is an integer of 0 to 2), but excluding —O—O—, —O—S— or —S—S— in the ring, with the remaining ring atoms being carbon atoms. Preferably, the heterocyclyl has 3 to 12 ring atoms wherein 1 to 4 atoms are heteroatoms; more preferably, 3 to 8 ring atoms; and most preferably 3 to 8 ring atoms. Non-limiting examples of monocyclic heterocyclyl include oxacyclobutyl, oxacyclobutyl, pyrrolidinyl, oxazolidin-2-one group, azepinyl, imidazolidinyl, tetrahydrofuranyl, tetrahydrothienyl, dihydroimidazolyl, dihydrofuranyl, dihydropyrazolyl, dihydropyrrolyl, piperidinyl, piperazinyl, morpholinyl, thiomorpholinyl, homopiperazinyl, pyranyl and the like, preferably oxacyclobutyl, tetrahydrofuranyl, pyrrolidinyl, pyrazolidinyl, piperazinyl, oxazolidin-2-one group, morpholinyl, piperazinyl and azepinyl, and more preferably oxacyclobutyl, pyrrolidinyl, piperidinyl, piperazinyl, azepinyl and oxazolidin-2-one group. Polycyclic heterocyclyl includes a heterocyclyl having a spiro ring, fused ring or bridged ring. The heterocyclyl having a spiro ring, fused ring or bridged ring is optionally bonded to other group via a single bond, or further bonded to other cycloalkyl, heterocyclyl, aryl and heteroaryl via any two or more atoms on the ring.

The term "spiro heterocyclyl" refers to a 3 to 20 membered polycyclic heterocyclyl group with individual rings connected through one shared atom (called a spiro atom), wherein one or more ring atoms are heteroatoms selected from the group consisting of nitrogen, oxygen, boron, phosphorus, $S(O)_m$ (wherein m is an integer of 0 to 2) and $P(O)_n$ (wherein n is an integer of 0 to 2), with the remaining ring atoms being carbon atoms, and the rings can contain one or more double bonds, but none of the rings has a completely conjugated π-electron system. The spiro heterocyclyl is preferably a 6 to 14 membered spiro heterocyclyl, and more preferably a 7 to 10 membered spiro heterocyclyl. According to the number of the spiro atoms shared between the rings, the spiro heterocyclyl can be divided into a mono-spiro heterocyclyl, di-spiro heterocyclyl, or poly-spiro heterocyclyl, and the spiro heterocyclyl is preferably a mono-spiro heterocyclyl or di-spiro heterocyclyl, and more preferably a 3-membered/5-membered, 4-membered/4-membered, 4-membered/5-membered, 4-membered/6-membered, 5-membered/5-membered, or 5-membered/6-membered mono-spiro heterocyclyl.

Non-limiting examples of spiro heterocyclyl include:

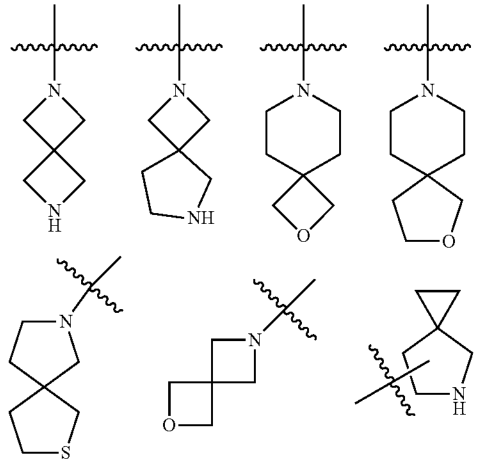

The term "fused heterocyclyl" refers to a 5 to 20 membered polycyclic heterocyclyl group, wherein each ring in the system shares an adjacent pair of atoms with another ring, one or more rings can contain one or more double bonds, but none of the rings has a completely conjugated π-electron system, and one or more ring atoms are heteroatoms selected from the group consisting of nitrogen, oxygen and $S(O)_m$ (wherein m is an integer of 0 to 2), with the remaining ring atoms being carbon atoms. The fused heterocyclyl is preferably a 6 to 14 membered fused heterocyclyl, and more preferably a 7 to 10 membered fused heterocyclyl. According to the number of membered rings, the fused heterocyclyl can be divided into a bicyclic, tricyclic, tetracyclic or polycyclic fused heterocyclyl, and preferably a bicyclic or tricyclic fused heterocyclyl, and more preferably a 3-membered/5-membered, 4-membered/5-membered or 5-membered/6-membered bicyclic fused heterocyclyl. Non-limiting examples of fused heterocyclyl include:

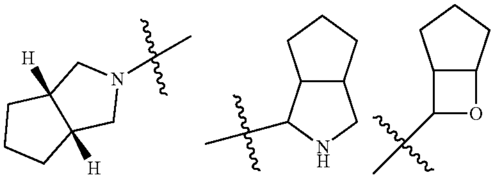

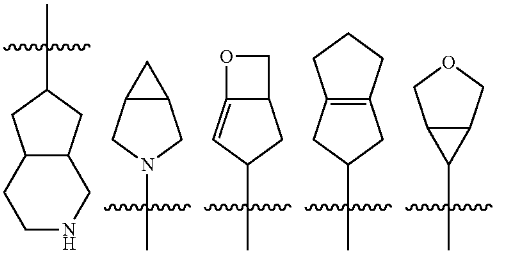

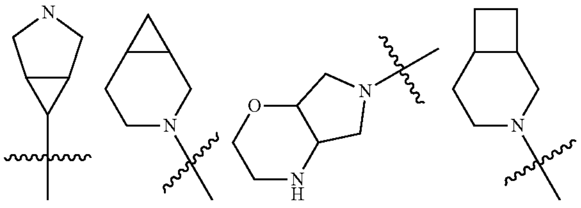

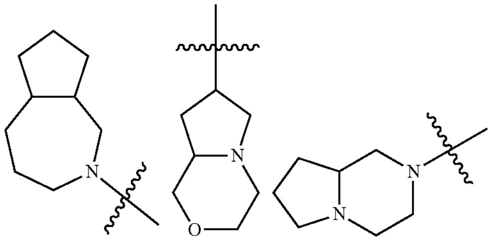

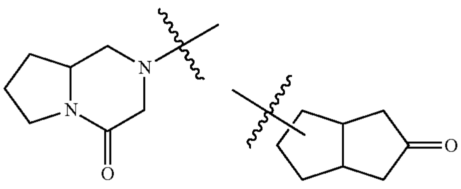

and the like.

The term "bridged heterocyclyl" refers to a 5 to 14 membered polycyclic heterocyclyl group, wherein every two rings in the system share two disconnected atoms, wherein the rings can have one or more double bond(s), but none of the rings has a completely conjugated π-electron system, and one or more ring atoms are heteroatoms selected from the group consisting of nitrogen, oxygen and $S(O)_m$ (wherein m is an integer of 0 to 2), with the remaining ring atoms being carbon atoms. The bridged heterocyclyl is preferably a 6 to 14 membered bridged heterocyclyl, and more preferably a 7 to 10 membered bridged heterocyclyl. According to the number of membered rings, the bridged heterocyclyl can be divided into a bicyclic, tricyclic, tetracyclic or polycyclic bridged heterocyclyl, and the bridged heterocyclyl is preferably a bicyclic, tricyclic or tetracyclic bridged heterocyclyl, and more preferably a bicyclic or tricyclic bridged heterocyclyl. Non-limiting examples of bridged heterocyclyl include:

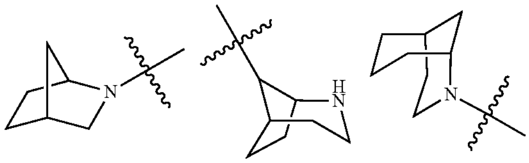

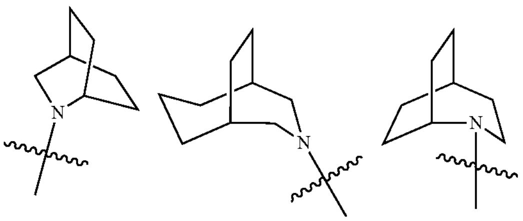

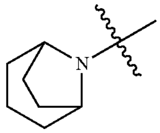

and

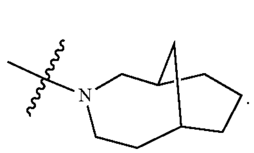

The heterocyclyl ring can be fused to the ring of aryl, heteroaryl or cycloalkyl, wherein the ring bound to the parent structure is heterocyclyl. Non-limiting examples thereof include:

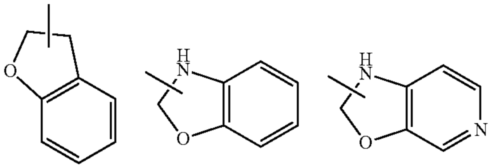

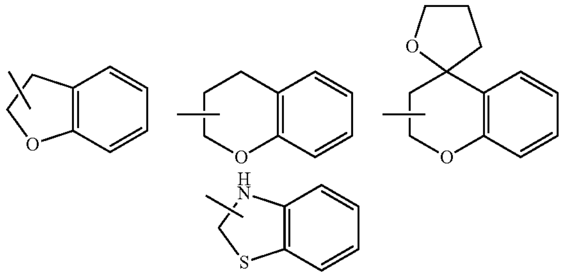

and the like.

The heterocyclyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl.

The term "aryl" refers to a 6 to 14 membered all-carbon monocyclic ring or polycyclic fused ring (i.e. each ring in the system shares an adjacent pair of carbon atoms with another ring in the system) having a conjugated π-electron system, preferably a 6 to 10 membered aryl, for example, phenyl and naphthyl. The aryl is more preferably phenyl. The aryl ring can be fused to the ring of heteroaryl, heterocyclyl or cycloalkyl, wherein the ring bound to the parent structure is aryl ring. Non-limiting examples thereof include:

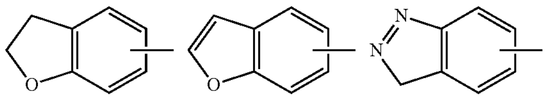
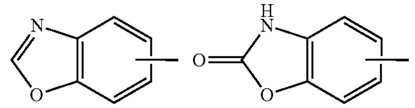
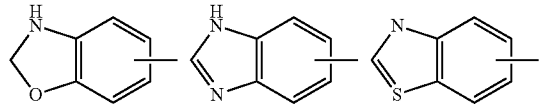
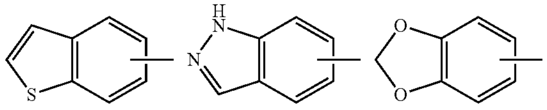
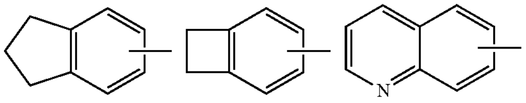
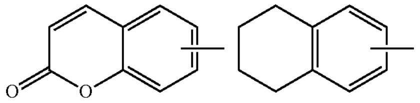
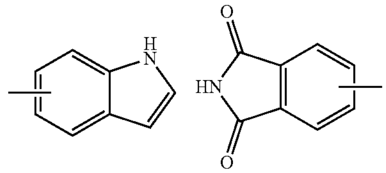
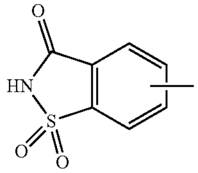

and the like.

The aryl can be substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

The term "heteroaryl" refers to a 5 to 14 membered heteroaromatic system having 1 to 4 heteroatoms selected from the group consisting of oxygen, sulfur and nitrogen. The heteroaryl is preferably a 5 to 12 membered heteroaryl, more preferably a 5 to 10 membered heteroaryl, and further preferably a 5 or 6 membered heteroaryl, wherein the heteroatom is 1 to 2 heteroatom(s) selected from the group consisting of oxygen, sulfur and nitrogen atom, for example imidazolyl, furanyl, thienyl, thiazolyl, pyrazolyl, oxazolyl, pyrrolyl, triazolyl, tetrazolyl, pyridyl, pyrimidinyl, thiadiazolyl, isoxazolyl, oxadiazolyl, pyrazinyl and the like, preferably pyridyl, thiazolyl, oxazolyl, isoxazolyl, oxadiazolyl, tetrazolyl, triazolyl, thienyl, imidazolyl, pyrazolyl, pyrimidinyl and thiazolyl, and more preferably pyridyl, thiazolyl, oxazolyl, isoxazolyl, furanyl and pyrimidinyl. The heteroaryl ring can be fused to the ring of aryl, heterocyclyl or cycloalkyl, wherein the ring bound to the parent structure is heteroaryl ring. Non-limiting examples thereof include:

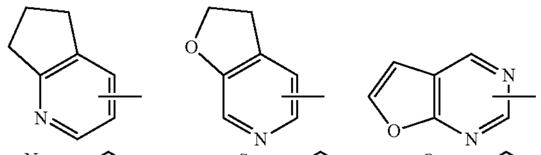
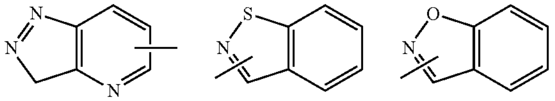
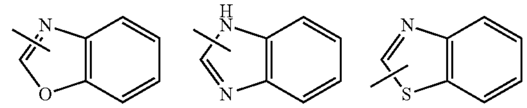
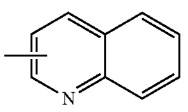

and

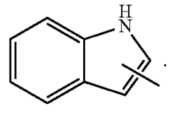

.

The heteroaryl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

The term "alkoxy" refers to an —O-(alkyl) or an —O-(unsubstituted cycloalkyl) group, wherein the alkyl is as defined above. Non-limiting examples of alkoxy include methoxy, ethoxy, propoxy, butoxy, cyclopropyloxy, cyclobutyloxy, cyclopentyloxy and cyclohexyloxy. The alkoxy can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

"Haloalkyl" refers to an alkyl group substituted by one or more halogen(s), wherein the alkyl is as defined above.

"Haloalkoxy" refers to an alkoxy group substituted by one or more halogen(s), wherein the alkoxy is as defined above.

"Hydroxyalkyl" refers to an alkyl group substituted by hydroxy(s), wherein the alkyl is as defined above.

"Alkenyl" refers to a chain alkenyl, also known as alkene group. The alkenyl can be further substituted by other related group, for example alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy or alkoxycarbonyl.

"Alkynyl" refers to (CH≡C—). The alkynyl can be further substituted by other related group, for example alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy or alkoxycarbonyl.

"Hydroxy" refers to an —OH group.

"Halogen" refers to fluorine, chlorine, bromine or iodine.

"Amino" refers to a $—NH_2$ group.

"Cyano" refers to a —CN group.

"Nitro" refers to a $—NO_2$ group.

"Carboxy" refers to a —C(O)OH group.

"THF" refers to tetrahydrofuran.

"EtOAc" refers to ethyl acetate.

"MeOH" refers to methanol.

"DMF" refers to N,N-dimethylformamide.

"DIPEA" refers to diisopropylethylamine.

"TFA" refers to trifluoroacetic acid.

"MeCN" refers to acetonitrile.

"DMA" refers to N,N-dimethylacetamide.

"$Et_2O$" refers to diethyl ether.

"DCE" refers to 1,2-dichloroethane.

"DIPEA" refers to N,N-diisopropylethylamine.

"NBS" refers to N-bromosuccinimide.

"NIS" refers to N-iodosuccinimide.

"Cbz-Cl" refers to benzyl chloroformate.

"$Pd_2(dba)_3$" refers to tris(dibenzylideneacetone)dipalladium.

"Dppf" refers to 1,1'-bisdiphenylphosphinoferrocene.

"HATU" refers to 2-(7-azabenzotriazol-1-yl)-N,N,N',N'-tetramethyluronium hexafluorophosphate.

"KHMDS" refers to potassium hexamethyldisilazide.

"LiHMDS" refers to lithium bis(trimethylsilyl)amide.

"MeLi" refers to methyl lithium.

"n-BuLi" refers to n-butyl lithium.

"$NaBH(OAc)_3$" refers to sodium triacetoxyborohydride.

Different expressions such as "X is selected from the group consisting of A, B or C", "X is selected from the group consisting of A, B and C", "X is A, B or C", "X is A, B and C" and the like, express the same meaning, that is, X can be any one or more of A, B and C.

The hydrogen atom of the present invention can be substituted by its isotope deuterium. Any of the hydrogen atoms in the compounds of the examples of the present invention can also be substituted by deuterium atom.

"Optional" or "optionally" means that the event or circumstance described subsequently can, but need not, occur, and such a description includes the situation in which the event or circumstance does or does not occur. For example, "the heterocyclyl optionally substituted by an alkyl" means that an alkyl group can be, but need not be, present, and such a description includes the situation of the heterocyclyl being substituted by an alkyl and the heterocyclyl being not substituted by an alkyl.

"Substituted" refers to one or more hydrogen atoms in a group, preferably up to 5, and more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without excessive efforts. For example, the combination of amino or hydroxy having free hydrogen and carbon atoms having unsaturated bonds (such as olefinic) may be unstable.

A "pharmaceutical composition" refers to a mixture of one or more of the compounds according to the present invention or physiologically/pharmaceutically acceptable salts or prodrugs thereof with other chemical components, and other components such as physiologically/pharmaceutically acceptable carriers and excipients. The purpose of the pharmaceutical composition is to facilitate administration of a compound to an organism, which is conducive to the absorption of the active ingredient so as to exert biological activity.

In general, the compound of formula (IX-A) or the pharmaceutically acceptable salt thereof is administered in a therapeutically effective amount by any acceptable administration mode of an agent with similar use. The therapeutically effective amount of the compound of the present disclosure may range from about 0.01 to about 500 mg per kg patient body weight per day, which can be administered in single dose or multiple doses. Suitable dose level can be about 0.1 to about 250 mg/kg per day, about 0.5 to about 100 mg/kg per day. Suitable dose level can be about 0.01 to about 250 mg/kg per day, about 0.05 to about 100 mg/kg per day, or about 0.1 to about 50 mg/kg per day. Within this range, the dose can be about 0.05 to about 0.5, about 0.5 to about 5 or about 5 to about 50 mg/kg per day. When administered orally, the composition may be provided in the form of a tablet containing about 1.0 to about 1000 mg of the active ingredient, particularly about 0.1, 0.5, 1, 1.5, 2, 2.5, 3, 3.5, 4, 4.5, 5, 6, 7.5, 10, 15, 20, 25, 50, 75, 100, 150, 200, 250, 300, 400, 500, 600, 750, 800, 900 and 1000 mg of the active ingredient, and preferably 0.1, 0.2, 0.25, 0.5, 1, 1.5, 2, 2.5, 3, 3.5, 4, 4.5, 5, 6, 7.5, 10, 15 and 20 mg of the active ingredient. The actual amount of the compound of the present disclosure, i.e., the active ingredient, depends on many factors, such as the severity of the disease to be treated, the age and relative health condition of the patient, the efficacy of the compound used, the route and form of administration and the like.

A "pharmaceutically acceptable salt" refers to a salt of the compound of the present invention, which is safe and effective in mammals and has the desired biological activity.

DETAILED DESCRIPTION OF THE INVENTION

The present invention will be further described with reference to the following examples, but the examples should not be considered as limiting the scope of the present invention.

EXAMPLES

The structures of the compounds of the present invention were identified by nuclear magnetic resonance (NMR) and/or liquid chromatography-mass spectrometry (LC-MS). NMR shifts (δ) are given in parts per million (ppm). NMR was determined by a Bruker AVANCE-400 machine. The solvents for determination were deuterated-dimethyl sulfoxide (DMSO-$d_6$), deuterated-methanol ($CD_3OD$) and deuterated-chloroform ($CDCl_3$), and the internal standard was tetramethylsilane (TMS).

Liquid chromatography-mass spectrometry (LC-MS) was determined on an Agilent 1200 Infinity Series mass spectrometer. High performance liquid chromatography (HPLC) was determined on an Agilent 1200DAD high pressure liquid chromatograph (Sunfire C18 150×4.6 mm chromatographic column), and a Waters 2695-2996 high pressure liquid chromatograph (Gimini C18 150×4.6 mm chromatographic column).

Yantai Huanghai HSGF254 or Qingdao GF254 silica gel plate was used as the thin-layer silica gel chromatography (TLC) plate. The dimension of the silica gel plate used in TLC was 0.15 mm to 0.2 mm, and the dimension of the silica gel plate used in product purification was 0.4 mm to 0.5 mm. Yantai Huanghai 200 to 300 mesh silica gel was generally used as a carrier for column chromatography.

The raw materials used in the examples of the present invention are known and commercially available, or can be synthesized by adopting or according to known methods in the art.

Unless otherwise stated, all reactions of the present invention were carried out under continuous magnetic stirring under dry nitrogen or argon atmosphere, the solvent was dry, and the reaction temperature was in degrees celsius.

Example 1

1-Benzyl-3-(trans-4-(2-(4-(2,3-dichlorophenyl)piperazin-1-yl)propyl)cyclohexyl)urea

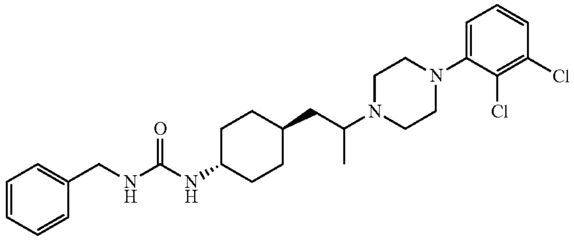 [SMILES: CC(C[C@H]1CC[C@H](NC(=O)NCc2ccccc2)CC1)N1CCN(c2cccc(Cl)c2Cl)CC1]

Step 1: 1-Benzyl-3-(trans-4-(2-(4-(2,3-dichlorophenyl)piperazin-1-yl)propyl)cyclohexyl)urea

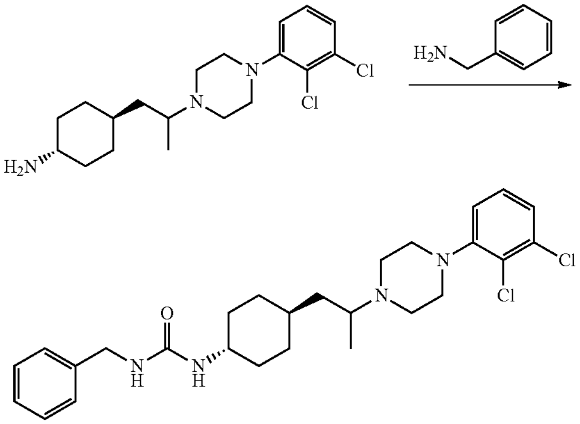

Trans-4-(2-(4-(2,3-dichlorophenyl)piperazin-1-yl)propyl)cyclohexan-1-amine (60 mg, 0.162 mmol) and triethylamine (50 mg, 0.49 mmol) were added to DCM (3 mL). CDI (29 mg, 0.178 mmol) was added, and the reaction solution was stirred at room temperature for 1 hour. Benzylamine (36 mg, 0.324 mmol) was added, and the reaction solution was stirred at room temperature for 16 hours. Water (20 mL) was added to the reaction solution, which was then extracted with ethyl acetate (20 mL×3). The organic phases were combined, washed with saturated brine (30 mL), dried over anhydrous sodium sulfate and filtered. The filtrate was concentrated under reduced pressure, and purified by preparative chromatography to obtain 1-benzyl-3-(trans-4-(2-(4-(2,3-dichlorophenyl)piperazin-1-yl)propyl)cyclohexyl)urea as a white solid (10 mg, yield: 12%).

$^1$H NMR (400 MHz, $CDCl_3$) δ 7.36-7.27 (m, 5H), 7.18-7.04 (m, 2H), 6.97 (d, J=6.9 Hz, 1H), 4.58 (s, 1H), 4.37 (d, J=5.7 Hz, 2H), 4.17 (d, J=7.5 Hz, 1H), 3.48 (s, 1H), 3.11-2.79 (m, 8H), 2.00 (s, 2H), 1.79-1.64 (m, 4H), 1.33-1.00 (m, 9H).

MS m/z (ESI): 503.2 $[M+H]^+$.

Example 2

3-(3-(2-(4-(2,3-Dichlorophenyl)piperazin-1-yl)ethyl)cyclobutyl)-1,1-dimethylurea

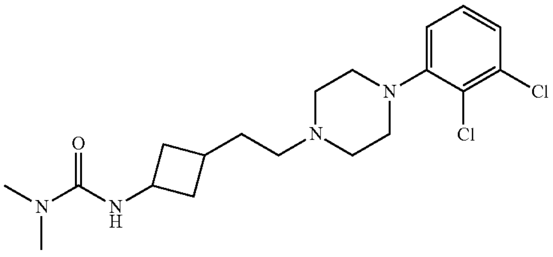 [SMILES: CN(C)C(=O)NC1CC(CCN2CCN(c3cccc(Cl)c3Cl)CC2)C1]

Step 1: Tert-butyl (3-oxocyclobutyl)carbamate

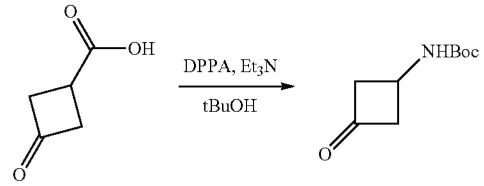 [SMILES: "tBuOH" ; O=C1CC(C(=O)O)C1 ; CC(C)(C)OC(=O)NC1CC(=O)C1]

3-Oxocyclobutane-1-carboxylic acid (1.5 g, 13.2 mmol), triethylamine (2.0 mL, 14.5 mmol) and toluene (30 mL) were added to a 100 mL eggplant-shaped flask successively. Diphenylphosphoryl azide (4.0 g, 14.5 mmol) was slowly added at −5° C. to 0° C. The reaction solution was stirred at 0° C. for 16 hours. The reaction solution was washed with saturated aqueous sodium bicarbonate solution (30 mL×1) and saturated aqueous sodium chloride solution (30 mL×1) at 0° C., and the organic phase was dried over anhydrous sodium sulfate. Tert-butanol (7.5 mL, 74.8 mmol) was added to the organic phase, and the reaction solution was heated to 100° C. and stirred for 16 hours. The reaction solution was concentrated to dryness by rotary evaporation to obtain the crude product. The crude product was purified by column chromatography (petroleum ether/ethyl acetate: 5/1) to obtain tert-butyl (3-oxocyclobutyl)carbamate (500 mg, yield: 20.5%).

$^1$H NMR (400 MHz, $CDCl_3$) δ 4.86 (s, 1H), 4.27 (s, 1H), 3.50-3.33 (m, 2H), 3.11-2.97 (m, 2H), 1.46 (s, 9H).

Step 2: Methyl 2-(3-((tert-butoxycarbonyl)amino)cyclobutylidene)acetate

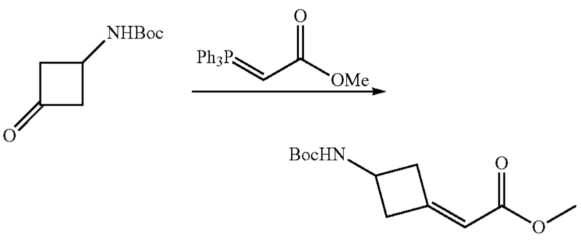

Tert-butyl (3-oxocyclobutyl)carbamate (450 mg, 2.43 mmol) and toluene (20 mL) were added to a 50 mL eggplant-shaped flask successively, followed by the slow addition of methyl (triphenylphosphoranylidene)acetate (1.22 g, 3.64 mmol). The reaction solution was refluxed under a nitrogen atmosphere for 16 hours, cooled, and concentrated to dryness by rotary evaporation to obtain the crude product. The crude product was purified by column chromatography (petroleum ether/ethyl acetate: 6/1) to obtain methyl 2-(3-((tert-butoxycarbonyl)amino)cyclobutylidene)acetate (450 mg, yield: 76.8%).

$^1H$ NMR (400 MHz, $CDCl_3$) δ 5.76-5.66 (m, 1H), 4.80 (br, 1H), 4.24 (s, 1H), 3.69 (s, 3H), 3.63-3.49 (m, 1H), 3.27-3.10 (m, 1H), 3.00-2.86 (m, 1H), 2.82-2.64 (m, 1H), 1.45 (s, 9H).

Step 3: Methyl 2-(3-((tert-butoxycarbonyl)amino)cyclobutyl)acetate

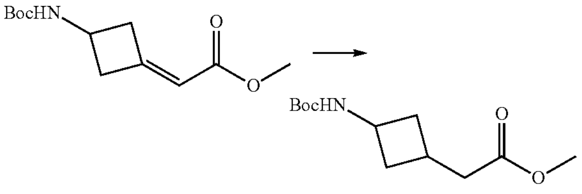

Methyl 2-(3-((tert-butoxycarbonyl)amino)cyclobutylidene)acetate (450 mg, 1.9 mmol) and methanol (10 mL) were added to a 50 mL eggplant-shaped flask successively. Pd/C (45 mg, containing 10% palladium and 50% water) were added slowly under a nitrogen atmosphere. The reaction solution was stirred under a hydrogen atmosphere (1 atm) for 5 hours, filtered, and concentrated to dryness by rotary evaporation to remove the solvent and obtain the crude product methyl 2-(3-((tert-butoxycarbonyl)amino)cyclobutyl)acetate (450 mg), which was used directly in the next step.

MS m/z (ESI): 244.2 $[M+H]^+$.

Step 4: Tert-butyl (3-(2-hydroxyethyl)cyclobutyl)carbamate

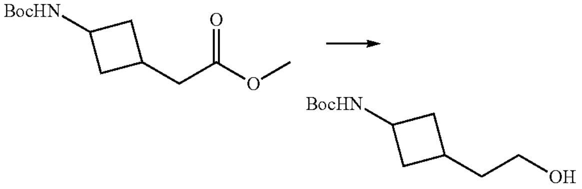

Methyl 2-(3-((tert-butoxycarbonyl)amino)cyclobutyl)acetate (450 mg, 1.9 mmol) and anhydrous tetrahydrofuran (10 mL) were added to a 50 mL eggplant-shaped flask successively. Lithium aluminum tetrahydride (210 mg, 5.6 mmol) was added slowly at 0° C. under a nitrogen atmosphere. The reaction solution was stirred at 0° C. for 2 hours, and the reaction was quenched by saturated aqueous sodium bicarbonate solution. The reaction solution was dried over anhydrous sodium sulfate directly, and stirred for 15 minutes. The organic phase was filtered, and concentrated to dryness by rotary evaporation to obtain the crude product tert-butyl (3-(2-hydroxyethyl)cyclobutyl)carbamate (450 mg), which was used directly in the next step.

MS m/z (ESI): 216.2 $[M+H]^+$.

Step 5: 2-(3-((Tert-butoxycarbonyl)amino)cyclobutyl)ethyl 4-methylbenzenesulfonate

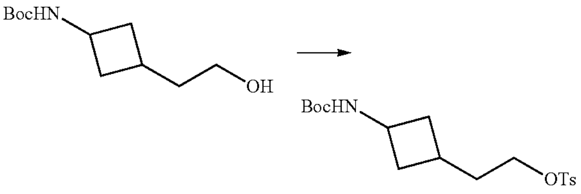

Tert-butyl (3-(2-hydroxyethyl)cyclobutyl)carbamate (450 mg, 2.1 mmol), triethylamine (634 mg, 6.3 mmol) and dichloromethane (10 mL) were added to a 50 mL eggplant-shaped flask successively, followed by the slow addition of 4-tosyl chloride (438 mg, 2.3 mmol). The reaction solution was stirred at room temperature overnight, followed by the addition of dichloromethane (20 mL), and washed with water (30 mL×1). The organic phase was dried and concentrated to dryness by rotary evaporation to obtain the crude product. The crude product was purified by column chromatography (petroleum ether/ethyl acetate: 5/1) to obtain 2-(3-((tert-butoxycarbonyl)amino)cyclobutyl)ethyl 4-methylbenzenesulfonate (710 mg, yield: 84%).

MS m/z (ESI): 370.2 $[M+H]^+$.

Step 6: Tert-butyl (3-(2-(4-(2,3-dichlorophenyl)piperazin-1-yl)ethyl)cyclobutyl)carbamate

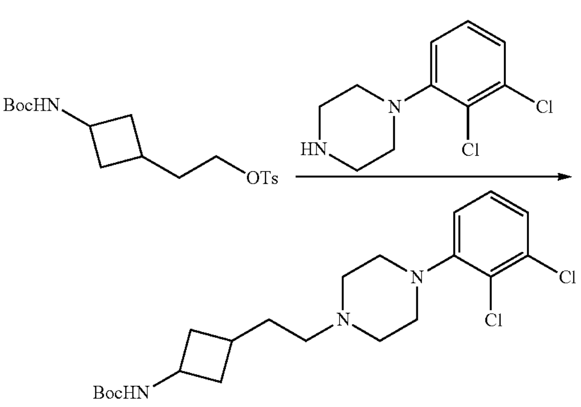

2-(3-((Tert-butoxycarbonyl)amino)cyclobutyl)ethyl 4-methylbenzenesulfonate (350 mg, 0.95 mmol), potassium carbonate (392 mg, 2.84 mmol) and acetonitrile (10 mL) were added to a 50 mL eggplant-shaped flask successively, followed by the slow addition of 1-(2,3-dichlorophenyl) piperazine (219 mg, 0.95 mmol). The reaction solution was refluxed overnight. The reaction solution was cooled, followed by the addition of dichloromethane (20 mL), and washed with water (30 mL×3). The organic phase was dried and concentrated to dryness by rotary evaporation to obtain the crude product. The crude product was purified by column chromatography (dichloromethane/methanol: 50/1) to obtain tert-butyl (3-(2-(4-(2,3-dichlorophenyl)piperazin-1-yl)ethyl)cyclobutyl)carbamate (310 mg, yield: 76%).

MS m/z (ESI): 428.2 $[M+H]^+$.

Step 7: 3-(2-(4-(2,3-Dichlorophenyl)piperazin-1-yl)ethyl)cyclobutan-1-amine hydrochloride

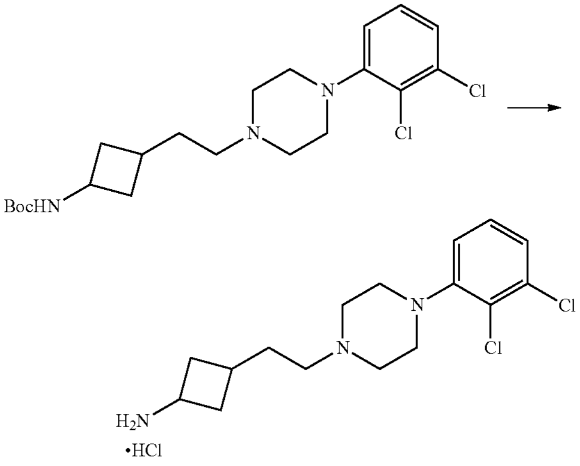

Tert-butyl (3-(2-(4-(2,3-dichlorophenyl)piperazin-1-yl)ethyl)cyclobutyl)carbamate (310 mg, 0.72 mmol) and ethyl acetate (2 mL) were added to a 25 mL eggplant-shaped flask successively, followed by the addition of hydrochloric acid in ethyl acetate (10 mL, 4M) at 0° C. The reaction solution was stirred at room temperature for 1 hour, and concentrated to dryness by rotary evaporation to remove the solvent and obtain the crude product 3-(2-(4-(2,3-dichlorophenyl)piperazin-1-yl)ethyl)cyclobutan-1-amine hydrochloride (310 mg), which was used directly in the next step.

MS m/z (ESI): 328.1 $[M+H]^+$.

Step 8: 3-(3-(2-(4-(2,3-Dichlorophenyl)piperazin-1-yl)ethyl)cyclobutyl)-1,1-dimethylurea

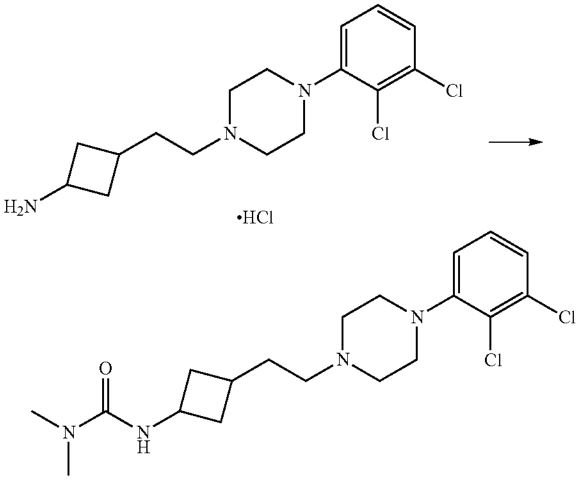

3-(2-(4-(2,3-Dichlorophenyl)piperazin-1-yl)ethyl)cyclobutan-1-amine hydrochloride (50 mg, 0.11 mmol), triethylamine (69 mg, 0.69 mmol) and dichloromethane (2 mL) were added to a 10 mL reaction flask successively, followed by the addition of dimethylcarbamoyl chloride (18.4 mg, 0.17 mmol) under stirring. The reaction solution was stirred at room temperature for 12 hours, and concentrated to dryness by rotary evaporation to remove the solvent and obtain the crude product. The crude product was purified by preparative HPLC to obtain 3-(3-(2-(4-(2,3-dichlorophenyl)piperazin-1-yl)ethyl)cyclobutyl)-1,1-dimethylurea (11 mg, yield: 24%).

$^1H$ NMR (400 MHz, $CDCl_3$) δ 7.23-7.10 (m, 2H), 7.08-6.91 (m, 1H), 4.61-3.93 (m, 2H), 3.56-3.02 (m, 4H), 3.03-2.64 (m, 8H), 2.65-2.31 (m, 3H), 2.31-1.21 (m, 7H).

MS m/z (ESI): 399.2$[M+H]^+$.

Example 2A

3-(Trans-3-(2-(4-(2,3-dichlorophenyl)piperazin-1-yl)ethyl)cyclobutyl)-1,1-dimethylurea

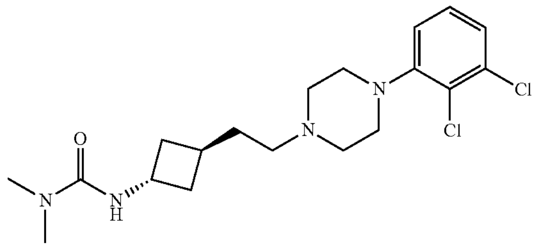

Step 1: Trans-3-(2-(4-(2,3-dichlorophenyl)piperazin-1-yl)ethyl)cyclobutan-1-amine (intermediate 2-1) and cis-3-(2-(4-(2,3-dichlorophenyl)piperazin-1-yl)ethyl)cyclobutan-1-amine (intermediate 2-2)

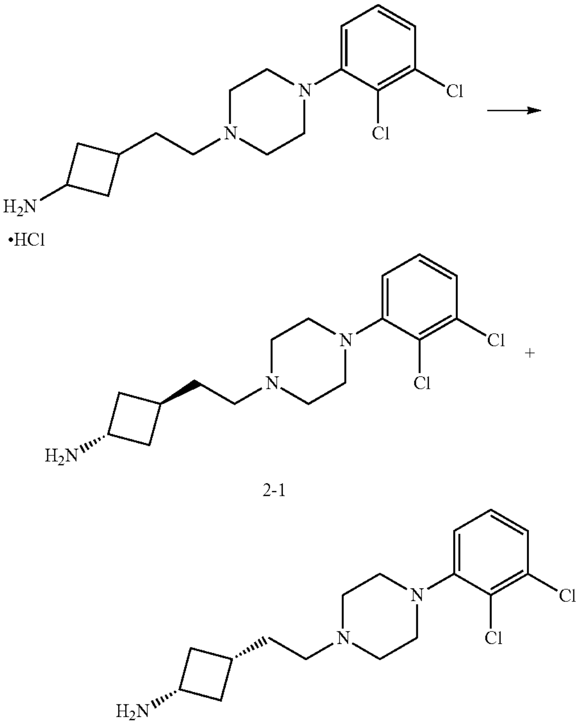

2-1

2-2

3-(2-(4-(2,3-Dichlorophenyl)piperazin-1-yl)ethyl)cyclobutan-1-amine hydrochloride was resolved to obtain trans-3-(2-(4-(2,3-dichlorophenyl)piperazin-1-yl)ethyl)cyclobutan-1-amine (2-1) and cis-3-(2-(4-(2,3-dichlorophenyl)piperazin-1-yl)ethyl)cyclobutan-1-amine (2-2).

Chiral Preparation Conditions:

| | |
|---|---|
| Instrument | SFC-200 (Thar, Waters) |
| Column type | AD 20*250 mm, 10 μm (Daicel) |
| Column pressure | 100 bar |
| Mobile phase | CO2/Methanol (0.2% Methanol Ammonia) = 70/30 |
| Flow rate | 130 g/min |
| Detection wavelength | UV 254 nm |
| Column temperature | 35° C. |

Intermediate 2-1: $T_R$=1.285 Min $^1$H NMR (400 MHz, Chloroform-d) δ 7.18-7.12 (m, 2H), 6.99-6.93 (m, 1H), 3.63-3.53 (m, 1H), 3.16-3.02 (m, 4H), 2.74-2.54 (m, 4H), 2.39-2.30 (m, 2H), 2.26-2.13 (m, 1H), 2.06-1.99 (m, 2H), 1.99-1.93 (m, 2H), 1.91-1.84 (m, 2H), 1.72-1.64 (m, 2H).

MS m/z (ESI): 328.1 $[M+H]^+$.

Intermediate 2-2: $T_R$=0.882 Min $^1$H NMR (400 MHz, Chloroform-d) δ 7.18-7.11 (m, 2H), 7.00-6.93 (m, 1H), 3.33-3.22 (m, 1H), 3.13-3.00 (m, 4H), 2.71-2.56 (m, 4H), 2.51-2.43 (m, 2H), 2.37-2.30 (m, 2H), 2.07-1.97 (m, 2H), 1.89-1.75 (m, 1H), 1.67-1.58 (m, 2H), 1.39-1.28 (m, 2H).

MS m/z (ESI): 328.1 $[M+H]^+$.

Step 2: 3-(Trans-3-(2-(4-(2,3-dichlorophenyl)piperazin-1-yl)ethyl)cyclobutyl)-1,1-dimethylurea

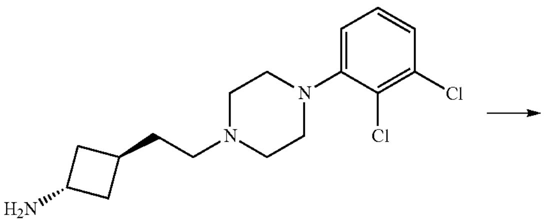

2-1

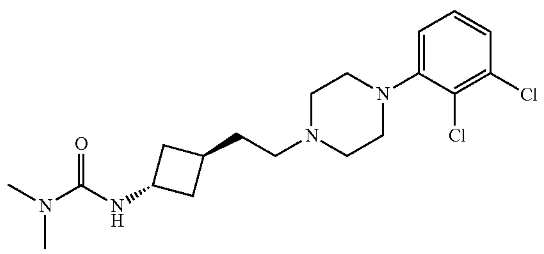 [SMILES: CN(C)C(=O)N[C@H]1C[C@H](CCN2CCN(c3cccc(Cl)c3Cl)CC2)C1]

In accordance with the reaction conditions of Step 8 of Example 2, the intermediate 2-1 was used as the starting material, accordingly, 3-(trans-3-(2-(4-(2,3-dichlorophenyl)piperazin-1-yl)ethyl)cyclobutyl)-1,1-dimethylurea was obtained.

$^1$H NMR (400 MHz, Chloroform-d) δ 7.23-7.07 (m, 2H), 7.07-6.91 (m, 1H), 4.49 (d, J=7.1 Hz, 1H), 4.44-4.28 (m, 1H), 3.53-3.03 (m, 5H), 2.90 (s, 6H), 2.82-2.61 (m, 3H), 2.51-2.35 (m, 2H), 2.27-2.10 (m, 3H), 2.08-1.95 (m, 2H), 1.88-1.72 (m, 2H).

MS m/z (ESI): 399.1$[M+H]^+$.

Example 2B 3-(Cis-3-(2-(4-(2,3-dichlorophenyl)piperazin-1-yl)ethyl)cyclobutyl)-1,1-dimethylurea

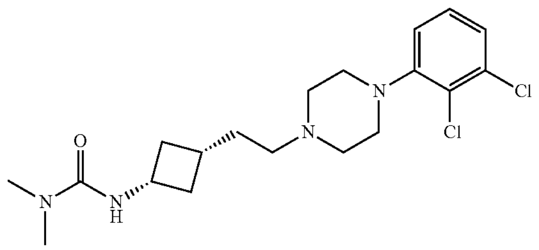

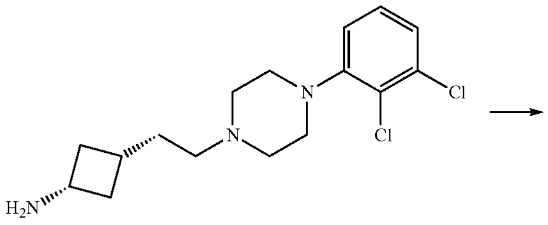

2-2

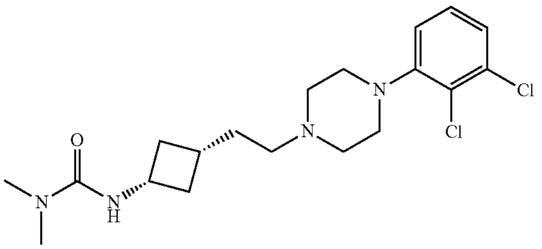 [SMILES: CN(C)C(=O)N[C@H]1C[C@@H](CCN2CCN(c3cccc(Cl)c3Cl)CC2)C1]

In accordance with the reaction conditions of Step 8 of Example 2, the intermediate 2-2 was used as the starting material, accordingly, 3-(cis-3-(2-(4-(2,3-dichlorophenyl)piperazin-1-yl)ethyl)cyclobutyl)-1,1-dimethylurea was obtained.

$^1$H NMR (400 MHz, Chloroform-d) δ 7.20-7.12 (m, 2H), 6.97 (dd, J=6.7, 2.8 Hz, 1H), 4.41 (d, J=7.5 Hz, 1H), 4.21-4.08 (m, 1H), 3.21-3.04 (m, 4H), 2.89 (s, 6H), 2.81-2.59 (m, 4H), 2.53 (dd, J=9.6, 7.0 Hz, 2H), 2.45-2.32 (m, 2H), 1.99-1.88 (m, 1H), 1.70-1.65 (m, 2H), 1.47-1.39 (m, 2H).

MS m/z (ESI): 399.1$[M+H]^+$.

Example 3

N-(3-(2-(4-(2,3-Dichlorophenyl)piperazin-1-yl)ethyl)cyclobutyl)propionamide

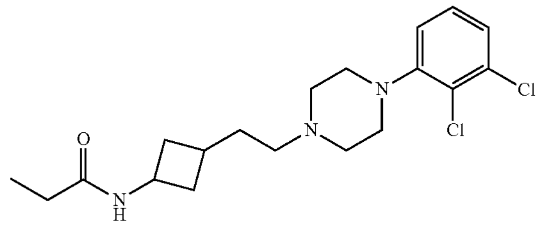 [SMILES: CCC(=O)NC1CC(CCN2CCN(c3cccc(Cl)c3Cl)CC2)C1]

Step 1: N-(3-(2-(4-(2,3-Dichlorophenyl)piperazin-1-yl)ethyl)cyclobutyl)propionamide

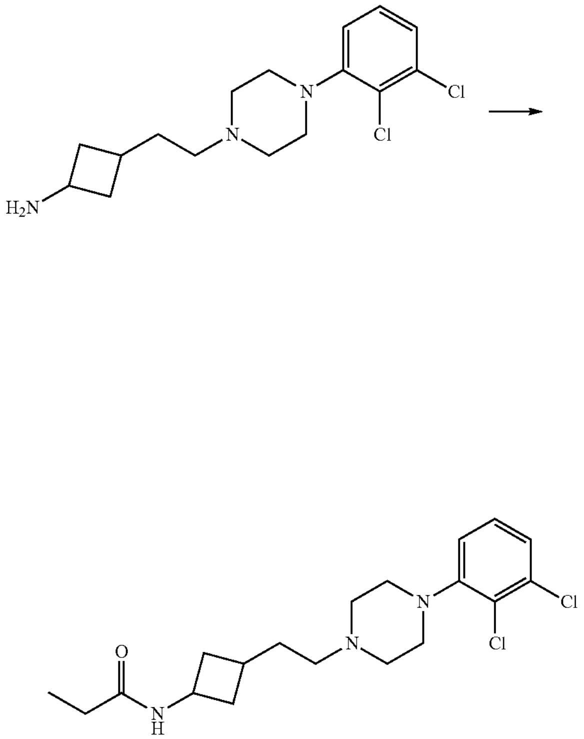

3-(2-(4-(2,3-Dichlorophenyl)piperazin-1-yl)ethyl)cyclobutan-1-amine hydrochloride (50 mg, 0.11 mmol), diisopropylethylamine (88 mg, 0.69 mmol) and dichloromethane (10 mL) were added to a 10 mL reaction flask successively, followed by the addition of propionyl chloride (12.7 mg, 0.14 mmol) under stirring. The reaction solution was stirred at room temperature for 12 hours, and washed with water. The organic phase was dried, and concentrated to dryness by rotary evaporation to remove the solvent and obtain the crude product. The crude product was purified by preparative HPLC to obtain N-(3-(2-(4-(2,3-dichlorophenyl)piperazin-1-yl)ethyl)cyclobutyl)propionamide (18 mg, yield: 41%).

MS m/z (ESI): 384.2[M+H]$^+$.

Example 4

1-Cyclopropyl-3-(3-(2-(4-(2,3-dichlorophenyl)piperazin-1-yl)ethyl)cyclobutyl)urea

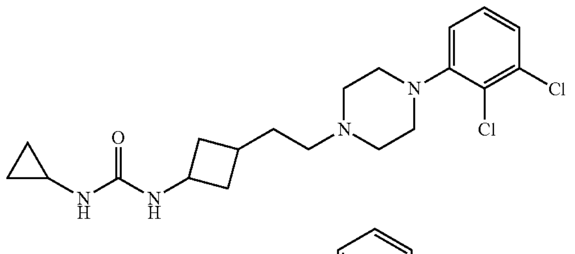

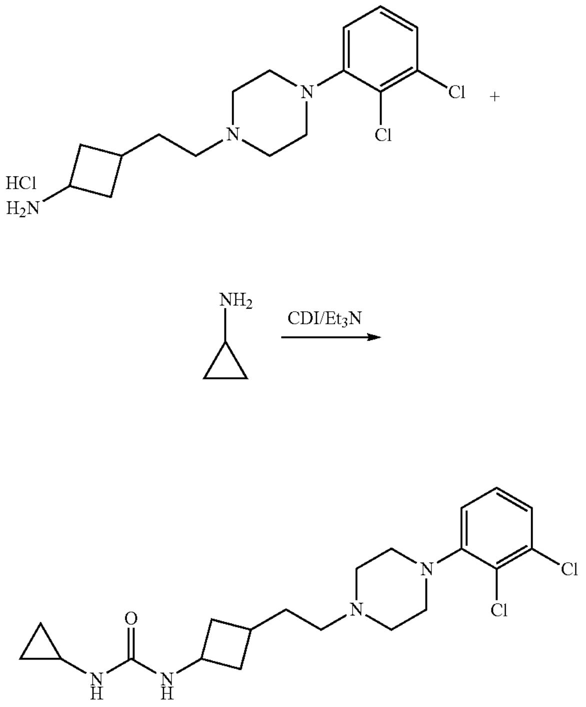

3-(2-(4-(2,3-Dichlorophenyl)piperazin-1-yl)ethyl)cyclobutan-1-amine hydrochloride (33 mg, 0.09 mmol), triethylamine (46 mg, 0.45 mmol) and N'N-carbonyldiimidazole (22 mg, 0.16 mmol) were dissolved in dichloromethane (2 mL). The reaction solution was stirred at room temperature for 2 hours, and the raw materials disappeared. Cyclopropylamine (10 mg, 0.18 mmol) was added, and the reaction solution was stirred at 35° C. for 48 hours. The reaction solution was concentrated to dryness by rotary evaporation, and the resulting crude product was purified by preparative HPLC to obtain 1-cyclopropyl-3-(3-(2-(4-(2,3-dichlorophenyl)piperazin-1-yl)ethyl)cyclobutyl)urea (12 mg, yield: 32.2%).

$^1$H NMR (400 MHz, $CDCl_3$) δ 7.20-7.12 (m, 2H), 6.97 (dd, J=7.0, 2.4 Hz, 1H), 5.08 (dd, J=28.8, 7.3 Hz, 1H), 4.64 (s, 1H), 4.43-4.09 (m, 1H), 3.14 (s, 4H), 2.73 (s, 4H), 2.56 (ddd, J=16.2, 7.4, 2.8 Hz, 2H), 2.43 (s, 3H), 2.05 (dddd, J=33.4, 24.1, 16.7, 8.5 Hz, 4H), 1.83-1.68 (m, 2H), 1.48 (dt, J=9.6, 6.0 Hz, 2H), 0.76 (q, J=6.3 Hz, 2H), 0.61-0.53 (m, 2H).

MS m/z (ESI): 411.2[M+H]$^+$.

Example 5

N-(3-(2-(4-(2,3-Dichlorophenyl)piperazin-1-yl)ethyl)cyclobutyl)-1H-indole-2-carboxamide

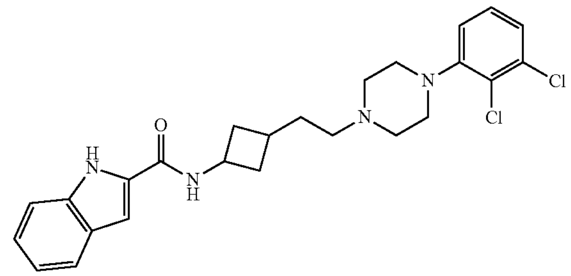 [SMILES: O=C(NC1CC(CCN2CCN(c3cccc(Cl)c3Cl)CC2)C1)c1cc2ccccc2[nH]1]

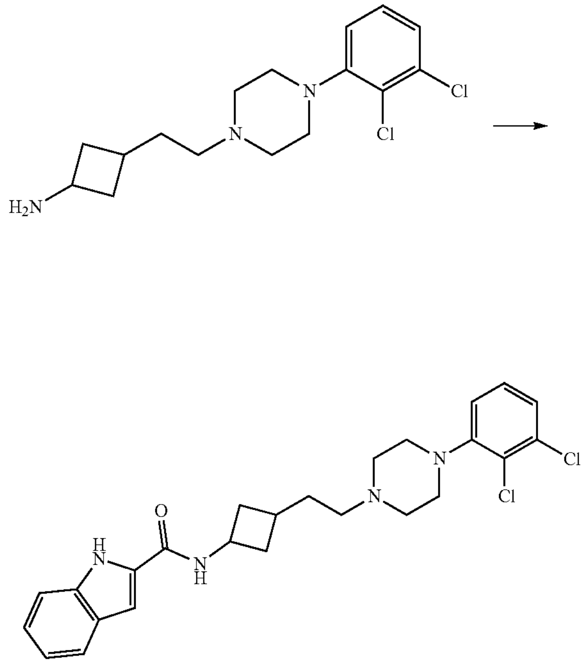

3-(2-(4-(2,3-Dichlorophenyl)piperazin-1-yl)ethyl)cyclobutan-1-amine (50 mg, 0.15 mmol) was dissolved in N,N-dimethylformamide (3 mL), followed by the addition of 1H-indole-2-carboxylic acid (30 mg, 0.18 mmol), HATU (86 mg, 0.23 mmol) and diisopropylethylamine (58 mg, 0.45 mmol). The reaction solution was stirred at room temperature overnight, and concentrated to dryness by rotary evaporation. The resulting crude product was purified by high performance liquid chromatography to obtain N-(3-(2-(4-(2,3-dichlorophenyl)piperazin-1-yl)ethyl)cyclobutyl)-1H-indole-2-carboxamide.

MS m/z (ESI): 471.2[M+H]$^+$.

Example 6

3-(3-(2-(4-(Benzo[b]thiophen-4-yl)piperazin-1-yl)ethyl)cyclobutyl)-1,1-dimethylurea

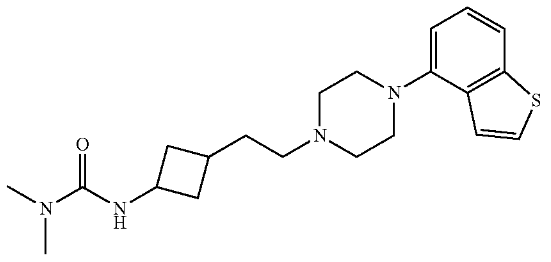 [SMILES: CN(C)C(=O)NC1CC(CCN2CCN(c3cccc4sccc34)CC2)C1]

Step 1: Tert-butyl (3-(2-(4-(benzo[b]thiophen-4-yl)piperazin-1-yl)ethyl)cyclobutyl)carbamate

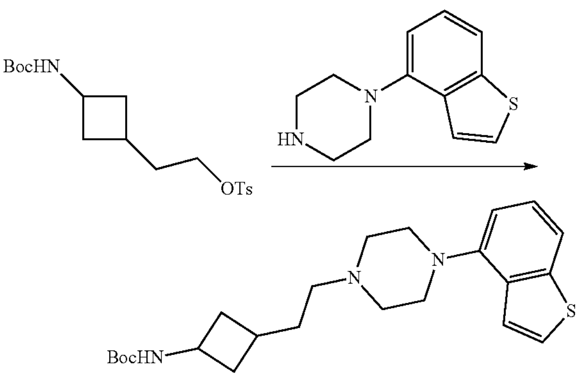

2-(3-((Tert-butoxycarbonyl)amino)cyclobutyl)ethyl 4-methylbenzenesulfonate (200 mg, 0.54 mmol), potassium carbonate (224 mg, 1.62 mmol) and acetonitrile (10 mL) were added to a 50 mL eggplant-shaped flask successively, followed by the slow addition of 1-(benzo[b]thiophen-4-yl)piperazine (118 mg, 0.54 mmol). The reaction solution was refluxed overnight. The reaction solution was cooled, followed by the addition of dichloromethane (20 mL), and washed with water (30 mL×3). The organic phase was dried and concentrated to dryness by rotary evaporation to obtain the crude product. The crude product was purified by column chromatography (dichloromethane/methanol: 50/1) to obtain tert-butyl (3-(2-(4-(benzo[b]thiophen-4-yl)piperazin-1-yl)ethyl)cyclobutyl)carbamate (120 mg, yield: 53%).

MS m/z (ESI): 416.2 [M+H]$^+$.

Step 2: 3-(2-(4-(Benzo[b]thiophen-4-yl)piperazin-1-yl)ethyl)cyclobutan-1-amine hydrochloride

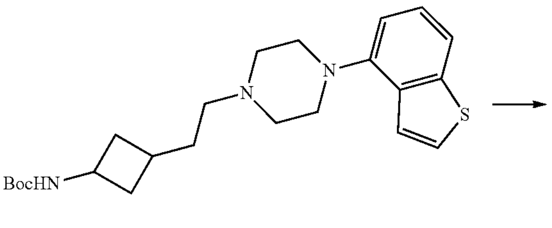

-continued

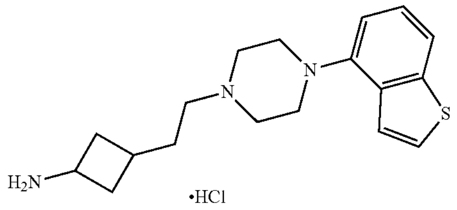

Tert-butyl (3-(2-(4-(benzo[b]thiophen-4-yl)piperazin-1-yl)ethyl)cyclobutyl)carbamate (120 mg, 0.29 mmol) and ethyl acetate (1 mL) were added to a 25 mL eggplant-shaped flask successively, followed by the addition of hydrochloric acid in ethyl acetate (6 mL, 4M) at 0° C. The reaction solution was stirred at room temperature for 1 hour, and concentrated to dryness by rotary evaporation to remove the solvent and obtain the crude hydrochloride (110 mg), which was used directly in the next step.

MS m/z (ESI): 316.1 $[M+H]^+$.

Step 3: 3-(3-(2-(4-(Benzo[b]thiophen-4-yl)piperazin-1-yl)ethyl)cyclobutyl)-1,1-dimethylurea

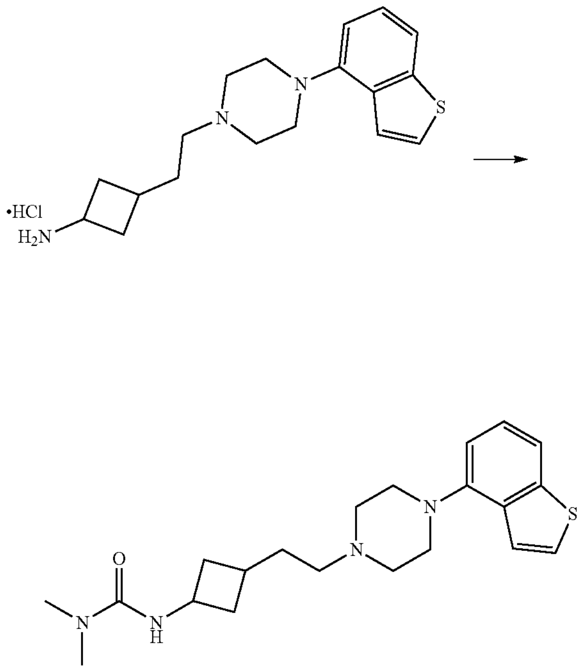

3-(2-(4-(Benzo[b]thiophen-4-yl)piperazin-1-yl)ethyl)cyclobutan-1-amine hydrochloride (50 mg, 0.12 mmol), triethylamine (71 mg, 0.70 mmol) and dichloromethane (2 mL) were added to a 10 mL reaction flask successively, followed by the addition of dimethylcarbamoyl chloride (19 mg, 0.18 mmol) under stirring. The reaction solution was stirred at room temperature for 12 hours, and concentrated to dryness by rotary evaporation to remove the solvent and obtain the crude product. The crude product was purified by preparative HPLC to obtain 3-(3-(2-(4-(benzo[b]thiophen-4-yl)piperazin-1-yl)ethyl)cyclobutyl)-1,1-dimethylurea (17 mg, yield: 37%).

MS m/z (ESI): 387.2 $[M+H]^+$.

Example 7

N-(3-(2-(4-(2,3-Dichlorophenyl)-1,4-diazepan-1-yl)ethyl)cyclobutyl)furan-2-carboxamide

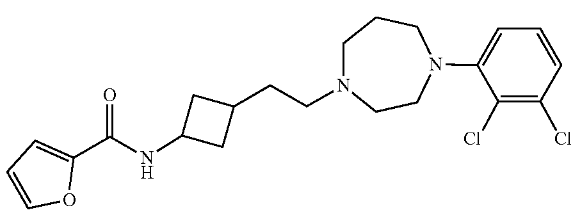 [SMILES: O=C(NC1CC(CCN2CCCN(c3cccc(Cl)c3Cl)CC2)C1)c1ccco1]

The process was the same as in Example 2.

MS m/z (ESI): 436.2$[M+H]^+$.

Example 8

N-(3-(2-(4-(2,3-Dichlorophenyl)piperazin-1-yl)ethyl)cyclobutyl)-5-methylfuran-2-carboxamide

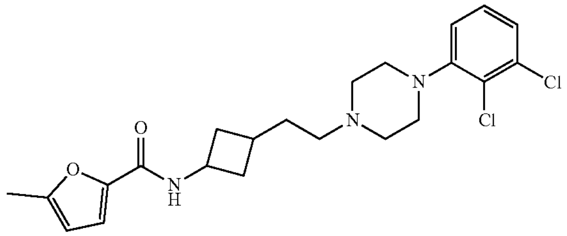 [SMILES: Cc1ccc(C(=O)NC2CC(CCN3CCN(c4cccc(Cl)c4Cl)CC3)C2)o1]

In accordance with Step 8 of Example 2, N-(3-(2-(4-(2,3-dichlorophenyl)piperazin-1-yl)ethyl)cyclobutyl)-5-methylfuran-2-carboxamide (23 mg, white solid, yield: 28.3%) was obtained.

$^1$H NMR (400 MHz, Chloroform-d) δ 7.21-7.12 (m, 2H), 7.01-6.96 (m, 2H), 6.39 (dd, J=34.1, 8.0 Hz, 1H), 6.11-6.06 (m, 1H), 4.52 (dq, J=84.5, 8.0 Hz, 1H), 3.23-3.05 (m, 4H), 2.76 (s, 4H), 2.59 (td, J=7.4, 6.8, 2.2 Hz, 1H), 2.48-2.46 (m, 1H), 2.35 (s, 3H), 2.24-2.13 (m, 2H), 2.04-1.97 (m, 1H), 1.84-1.75 (m, 2H), 1.62 (qd, J=9.1, 2.8 Hz, 2H).

MS m/z (ESI): 436.1 $[M+H]^+$.

Example 9

N-(3-(2-(4-(2,3-Dichlorophenyl)piperazin-1-yl)ethyl)cyclobutyl)-2-methoxyacetamide

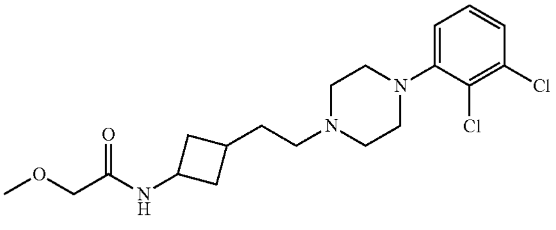 [SMILES: COCC(=O)NC1CC(CCN2CCN(c3cccc(Cl)c3Cl)CC2)C1]

In accordance with Step 8 of Example 2, N-(3-(2-(4-(2,3-dichlorophenyl)piperazin-1-yl)ethyl)cyclobutyl)-2-methoxyacetamide (29 mg, white solid, yield: 33%) was obtained.

$^1$H NMR (400 MHz, Chloroform-d) δ 7.19-7.12 (m, 2H), 6.97 (dd, J=7.0, 2.5 Hz, 1H), 6.63 (dd, J=42.2, 8.2 Hz, 1H), 4.42 (dq, J=87.5, 7.9 Hz, 1H), 3.86 (d, J=4.7 Hz, 2H), 3.42 (d, J=2.5 Hz, 3H), 3.22-3.06 (m, 4H), 2.81-2.61 (m, 4H), 2.58-2.52 (m, 1H), 2.45-2.32 (m, 2H), 2.21-2.03 (m, 2H), 2.02-1.91 (m, 1H), 1.79-1.73 (m, 1H), 1.70-1.67 (m, 1H), 1.57-1.49 (m, 1H).

MS m/z (ESI): 400.1 [M+H]$^+$.

Example 10

N-(3-(2-(4-(2,3-Dichlorophenyl)piperazin-1-yl)ethyl)cyclobutyl)nicotinamide

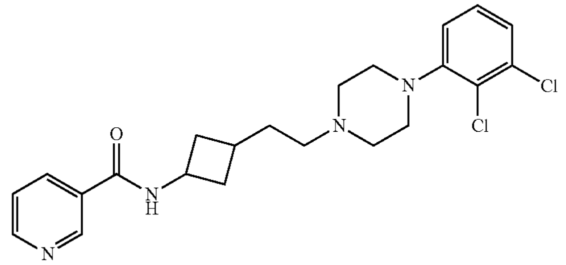 [SMILES: O=C(NC1CC(CCN2CCN(c3cccc(Cl)c3Cl)CC2)C1)c1cccnc1]

In accordance with Example 2, N-(3-(2-(4-(2,3-dichlorophenyl)piperazin-1-yl)ethyl)cyclobutyl)nicotinamide (25 mg, white solid, yield: 29%) was obtained.

The compound of Example 10 can also be obtained in accordance with the synthesis method of Example 5.

$^1$H NMR (400 MHz, Chloroform-d) δ 8.97 (d, J=2.2 Hz, 1H), 8.72 (dd, J=4.8, 1.8 Hz, 1H), 8.12 (dq, J=8.0, 2.0 Hz, 1H), 7.44-7.34 (m, 1H), 7.19-7.12 (m, 2H), 6.97 (dt, J=7.0, 2.7 Hz, 1H), 6.41 (dd, J=14.4, 7.5 Hz, 1H), 4.85-4.34 (m, 1H), 3.12 (t, J=5.0 Hz, 4H), 2.78-2.66 (m, 4H), 2.46-2.39 (m, 2H), 2.27-2.16 (m, 2H), 2.13-2.02 (m, 1H), 1.87-1.79 (m, 1H), 1.79-1.57 (m, 3H).

MS m/z (ESI): 433.1 [M+H]$^+$.

Example 11

N-(3-(2-(4-(2,3-Dichlorophenyl)piperazin-1-yl)ethyl)cyclobutyl)-2-hydroxy-2-methylpropanamide

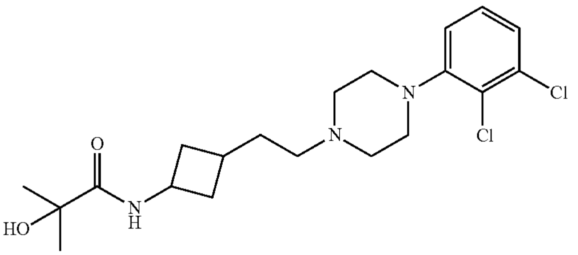 [SMILES: CC(C)(O)C(=O)NC1CC(CCN2CCN(c3cccc(Cl)c3Cl)CC2)C1]

In accordance with Example 2, N-(3-(2-(4-(2,3-dichlorophenyl)piperazin-1-yl)ethyl)cyclobutyl)-2-hydroxy-2-methylpropanamide (32 mg, white solid, yield: 30%) was obtained.

The compound of Example 11 can also be obtained in accordance with the synthesis method of Example 5.

MS m/z (ESI): 414.1 [M+H]$^+$.

Example 12

N-(3-(2-(4-(2,3-Dichlorophenyl)piperazin-1-yl)ethyl)cyclobutyl)-3-methoxyazetidine-1-carboxamide

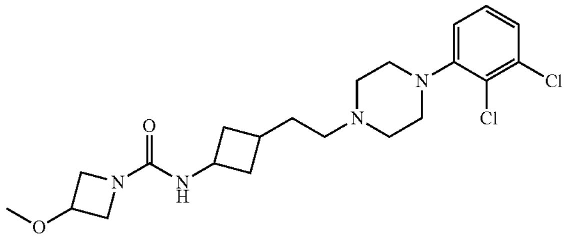 [SMILES: COC1CN(C(=O)NC2CC(CCN3CCN(c4cccc(Cl)c4Cl)CC3)C2)C1]

In accordance with Example 4, N-(3-(2-(4-(2,3-dichlorophenyl)piperazin-1-yl)ethyl)cyclobutyl)-3-methoxyazetidine-1-carboxamide (22 mg, white solid, yield: 23%) was obtained.

$^1$H NMR (400 MHz, Chloroform-d) δ 7.18-7.12 (m, 2H), 6.96 (dd, J=7.1, 2.6 Hz, 1H), 4.41-4.22 (m, 1H), 4.21-4.15 (m, 2H), 4.11-4.06 (m, 2H), 3.85-3.78 (m, 2H), 3.29 (s, 3H), 3.16-3.08 (m, 4H), 2.69 (s, 4H), 2.55-2.49 (m, 1H), 2.42-2.35 (m, 2H), 2.11 (ddd, J=11.5, 7.3, 2.9 Hz, 1H), 2.04-1.85 (m, 2H), 1.71 (dq, J=32.8, 7.8 Hz, 2H), 1.44 (td, J=9.2, 2.9 Hz, 1H).

MS m/z (ESI): 441.1 [M+H]$^+$.

Example 13

N-(3-(2-(4-(2,3-Dichlorophenyl)piperazin-1-yl)ethyl)cyclobutyl)-1-hydroxycyclopropane-1-carboxamide

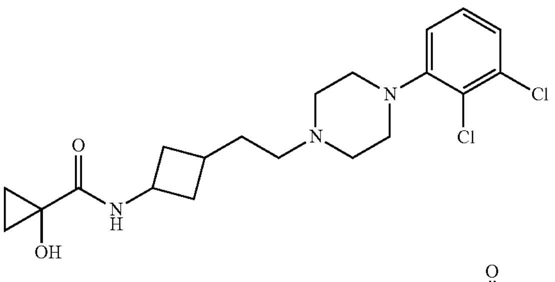

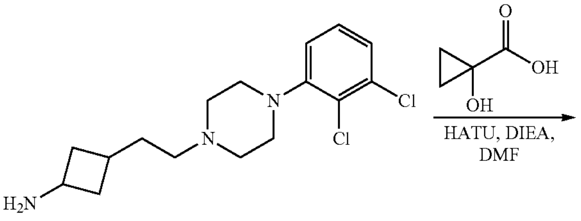

-continued

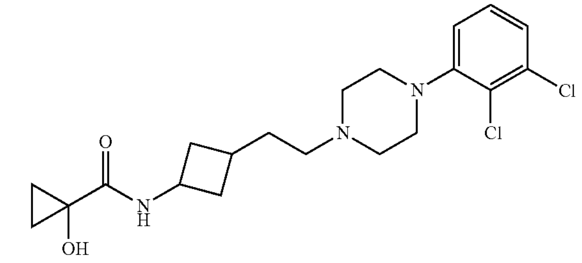

3-(2-(4-(2,3-Dichlorophenyl)piperazin-1-yl)ethyl)cyclobutan-1-amine (50 mg, 0.15 mmol) was dissolved in N,N-dimethylformamide (3 mL), followed by the addition of 1-hydroxycyclopropane-1-carboxylic acid (18 mg, 0.18 mmol), HATU (86 mg, 0.23 mmol) and diisopropylethylamine (58 mg, 0.45 mmol). The reaction solution was stirred at room temperature overnight, and concentrated to dryness by rotary evaporation. The resulting crude product was purified by high performance liquid chromatography to obtain N-(3-(2-(4-(2,3-dichlorophenyl)piperazin-1-yl)ethyl)cyclobutyl)-1-hydroxycyclopropane-1-carboxamide (13 mg, white solid, yield: 21%).

$^1$H NMR (400 MHz, Chloroform-d) δ 7.20-7.12 (m, 2H), 7.07 (dd, J=28.3, 8.0 Hz, 1H), 6.96 (dd, J=7.1, 2.5 Hz, 1H), 4.38 (dq, J=87.6, 7.9 Hz, 1H), 3.20-3.05 (m, 4H), 2.72 (s, 4H), 2.56 (dd, J=8.9, 2.9 Hz, 1H), 2.41 (dd, J=9.5, 6.3 Hz, 2H), 2.25 (d, J=8.4 Hz, 1H), 2.19-2.06 (m, 2H), 1.99 (dd, J=14.2, 6.4 Hz, 1H), 1.82-1.69 (m, 2H), 1.55 (dd, J=9.1, 2.9 Hz, 1H), 1.35-1.30 (m, 2H), 1.01 (q, J=4.6 Hz, 2H).

MS m/z (ESI): 412.1 $[M+H]^+$.

Example 13A

N-(Trans-3-(2-(4-(2,3-dichlorophenyl)piperazin-1-yl)ethyl)cyclobutyl)-1-hydroxycyclopropane-1-carboxamide

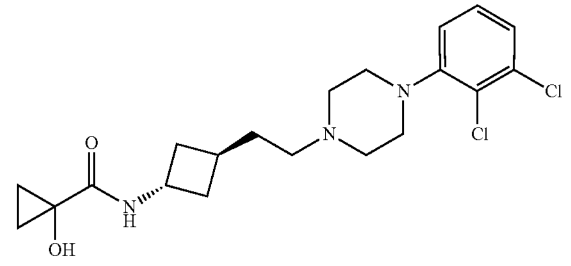

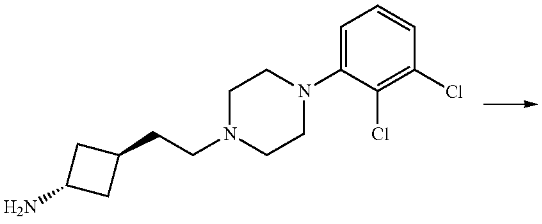

2-1

-continued

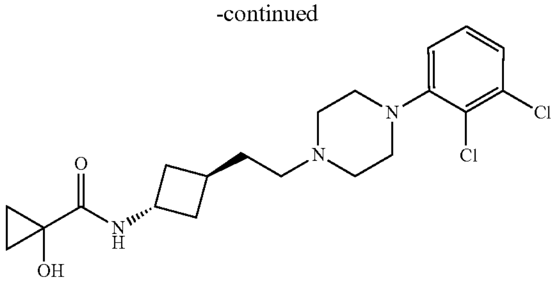

In accordance with the reaction conditions of Example 13, the intermediate 2-1 was used as the starting material, accordingly, N-(trans-3-(2-(4-(2,3-dichlorophenyl)piperazin-1-yl)ethyl)cyclobutyl)-1-hydroxycyclopropane-1-carboxamide was obtained.

$^1$H NMR (400 MHz, Chloroform-d) δ 7.20-7.13 (m, 2H), 7.07 (d, J=8.0 Hz, 1H), 6.97 (dd, J=7.0, 2.6 Hz, 1H), 4.56-4.44 (m, 1H), 3.22-3.07 (m, 4H), 2.86-2.66 (m, 4H), 2.50-2.41 (m, 2H), 2.32-2.24 (m, 1H), 2.20-2.05 (m, 5H), 1.84-1.76 (m, 2H), 1.38-1.32 (m, 2H), 1.06-1.00 (m, 2H).

MS m/z (ESI): 412.1 $[M+H]^+$.

Example 13B

N-(Cis-3-(2-(4-(2,3-dichlorophenyl)piperazin-1-yl)ethyl)cyclobutyl)-1-hydroxycyclopropane-1-carboxamide

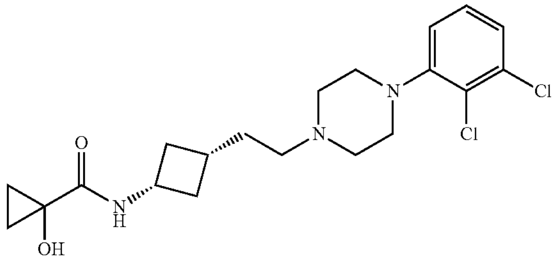 [SMILES: O=C(N[C@H]1C[C@@H](CCN2CCN(c3cccc(Cl)c3Cl)CC2)C1)C1(O)CC1]

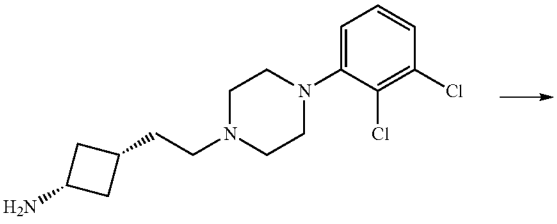

2-2

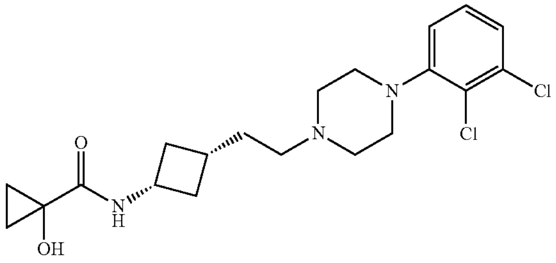

In accordance with the reaction conditions of Example 13, the intermediate 2-2 was used as the starting material, accordingly, N-(cis-3-(2-(4-(2,3-dichlorophenyl)piperazin-1-yl)ethyl)cyclobutyl)-1-hydroxycyclopropane-1-carboxamide (13B) was obtained.

$^1H$ NMR (400 MHz, Chloroform-d) δ 7.24-7.15 (m, 2H), 7.09 (d, J=7.8 Hz, 1H), 7.02-6.98 (m, 1H), 4.36-4.25 (m, 1H), 3.33 (s, 4H), 3.18-2.95 (m, 3H), 2.73-2.65 (m, 2H), 2.63-2.54 (m, 2H), 2.05-1.89 (m, 4H), 1.71-1.59 (m, 3H), 1.36-1.30 (m, 2H), 1.06-1.00 (m, 2H).

MS m/z (ESI): 412.1 $[M+H]^+$.

Example 14

N-(3-(2-(4-(2,3-Dichlorophenyl)piperazin-1-yl)ethyl)cyclobutyl)thiazole-2-carboxamide

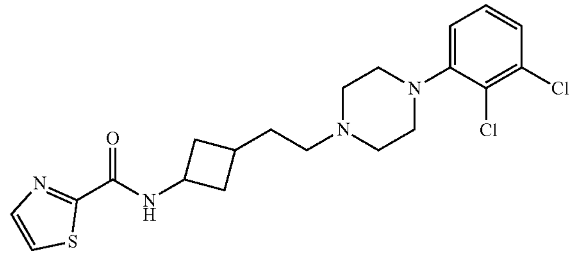

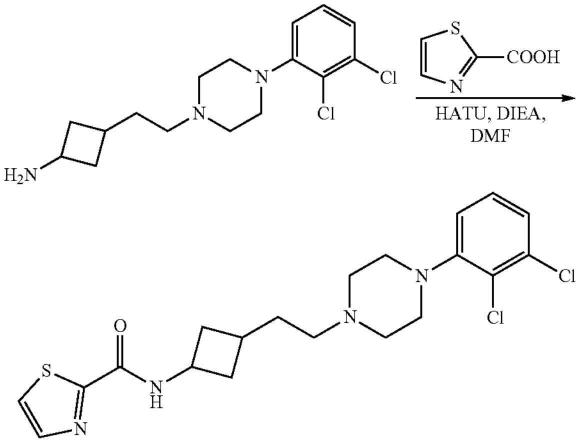

3-(2-(4-(2,3-Dichlorophenyl)piperazin-1-yl)ethyl)cyclobutan-1-amine (50 mg, 0.15 mmol) was dissolved in N,N-dimethylformamide (3 mL), followed by the addition of thiazole-2-carboxylic acid (23 mg, 0.18 mmol), HATU (86 mg, 0.23 mmol) and diisopropylethylamine (58 mg, 0.45 mmol). The reaction solution was stirred at room temperature overnight, and concentrated to dryness by rotary evaporation. The resulting crude product was purified by high performance liquid chromatography to obtain N-(3-(2-(4-(2,3-dichlorophenyl)piperazin-1-yl)ethyl)cyclobutyl)thiazole-2-carboxamide (21 mg, white solid, yield: 32%).

$^1H$ NMR (400 MHz, Chloroform-d) δ 7.86 (dd, J=3.1, 1.5 Hz, 1H), 7.57 (d, J=3.1 Hz, 1H), 7.40 (dd, J=42.4, 8.2 Hz, 1H), 7.20-7.12 (m, 2H), 7.01-6.93 (m, 1H), 4.73-4.28 (m, 1H), 3.18-3.03 (m, 4H), 2.78-2.54 (m, 6H), 2.44-2.35 (m, 2H), 2.24-2.19 (m, 1H), 2.10-1.98 (m, 1H), 1.81-1.75 (m, 1H), 1.71-1.65 (m, 2H).

MS m/z (ESI): 439.1 $[M+H]^+$.

Example 14A

N-(Trans-3-(2-(4-(2,3-dichlorophenyl)piperazin-1-yl)ethyl)cyclobutyl)thiazole-2-carboxamide

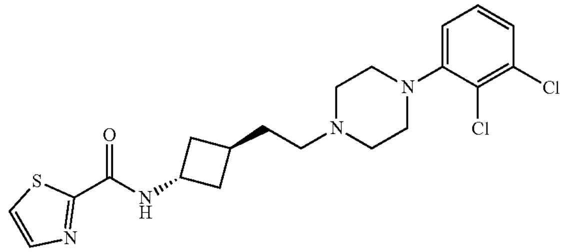

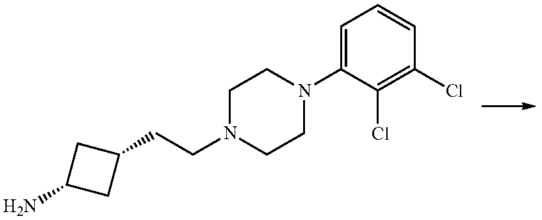

2-1

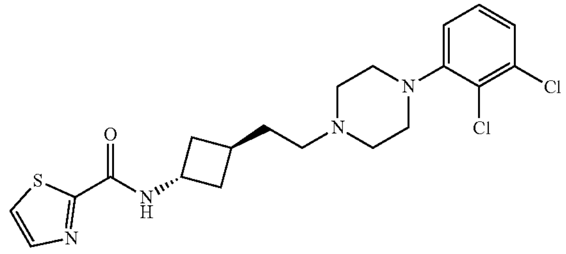

In accordance with the reaction conditions of Example 14, the intermediate 2-1 was used as the starting material, accordingly, N-(trans-3-(2-(4-(2,3-dichlorophenyl)piperazin-1-yl)ethyl)cyclobutyl)thiazole-2-carboxamide (21 mg, white solid, yield: 32%) was obtained.

$^1H$ NMR (400 MHz, Chloroform-d) δ 7.86 (d, J=3.1 Hz, 1H), 7.57 (d, J=3.1 Hz, 1H), 7.45 (d, J=8.0 Hz, 1H), 7.21-7.13 (m, 2H), 7.00-6.95 (m, 1H), 4.74-4.59 (m, 1H), 3.18-3.02 (m, 4H), 2.79-2.58 (m, 4H), 2.47-2.38 (m, 2H), 2.35-2.27 (m, 1H), 2.25-2.18 (m, 4H), 1.87-1.77 (m, 2H).

MS m/z (ESI): 439.1 $[M+H]^+$.

Example 15

N-(3-(2-(4-(2,3-Dichlorophenyl)piperazin-1-yl)ethyl)cyclobutyl)-3-hydroxy-3-methylbutanamide

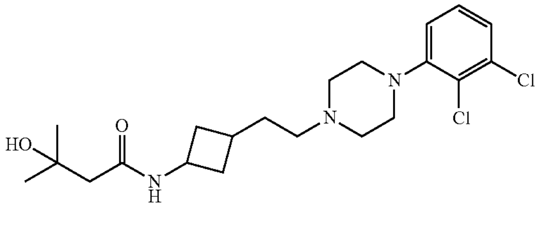 [SMILES: CC(C)(O)CC(=O)NC1CC(CCN2CCN(c3cccc(Cl)c3Cl)CC2)C1]

In accordance with Example 2, N-(3-(2-(4-(2,3-dichlorophenyl)piperazin-1-yl)ethyl)cyclobutyl)-3-hydroxy-3-methylbutanamide (21 mg, white solid, yield: 20%) was obtained.

The compound of Example 15 can also be obtained in accordance with the synthesis method of Example 5.

$^1$H NMR (400 MHz, Chloroform-d) δ 7.21-7.13 (m, 2H), 6.96 (dd, J=7.0, 2.7 Hz, 1H), 6.08 (dd, J=21.6, 7.5 Hz, 1H), 4.51-4.19 (m, 2H), 3.10 (d, J=6.2 Hz, 4H), 2.76-2.62 (m, 4H), 2.56 (ddd, J=8.9, 5.9, 2.7 Hz, 1H), 2.42-2.36 (m, 2H), 2.29 (d, J=6.4 Hz, 2H), 2.05-1.96 (m, 3H), 1.72 (dq, J=28.0, 7.6 Hz, 2H), 1.51 (td, J=9.1, 2.8 Hz, 1H), 1.27 (d, J=2.2 Hz, 6H).

MS m/z (ESI): 428.1 $[M+H]^+$.

Example 16

N-(3-(2-(4-(2,3-Dichlorophenyl)piperazin-1-yl)ethyl)cyclobutyl)-2-(5-methyloxazol-2-yl)acetamide

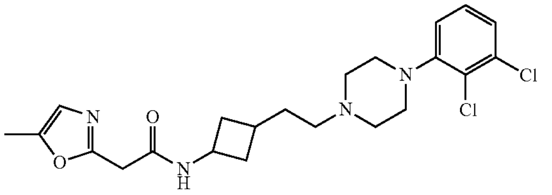 [SMILES: Cc1cnc(CC(=O)NC2CC(CCN3CCN(c4cccc(Cl)c4Cl)CC3)C2)o1]

In accordance with Example 2, N-(3-(2-(4-(2,3-dichlorophenyl)piperazin-1-yl)ethyl)cyclobutyl)-2-(5-methyloxazol-2-yl)acetamide (15 mg, white solid, yield: 16%) was obtained.

The compound of Example 16 can also be obtained in accordance with the synthesis method of Example 5.

MS m/z (ESI): 451.1 $[M+H]^+$.

Example 17

N-(3-(2-(4-(2,3-Dichlorophenyl)piperazin-1-yl)ethyl)cyclobutyl)-2-(3-methylisoxazol-5-yl)acetamide

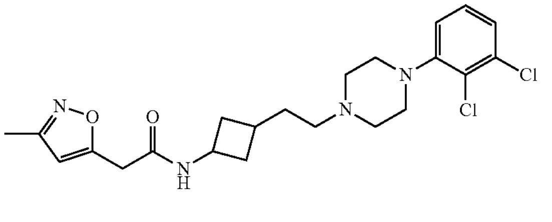 [SMILES: Cc1cc(CC(=O)NC2CC(CCN3CCN(c4cccc(Cl)c4Cl)CC3)C2)on1]

In accordance with Example 2, N-(3-(2-(4-(2,3-dichlorophenyl)piperazin-1-yl)ethyl)cyclobutyl)-2-(3-methylisoxazol-5-yl)acetamide (26 mg, white solid, yield: 28%) was obtained.

The compound of Example 17 can also be obtained in accordance with the synthesis method of Example 5.

MS m/z (ESI): 451.1 $[M+H]^+$.

Example 18

N-(3-(2-(4-(2,3-Dichlorophenyl)piperazin-1-yl)ethyl)cyclobutyl)cyclopropanesulfonamide

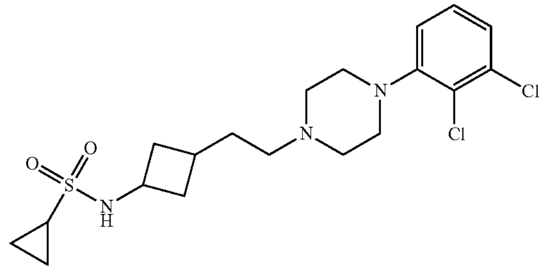

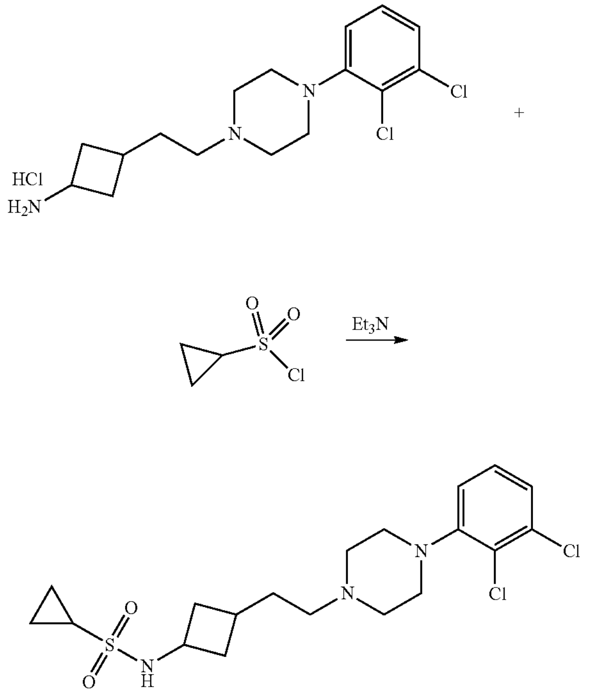

3-(2-(4-(2,3-Dichlorophenyl)piperazin-1-yl)ethyl)cyclobutan-1-amine hydrochloride (40 mg, 0.11 mmol), triethylamine (44 mg, 0.44 mmol) and cyclopropanesulfonyl chloride (31 mg, 0.22 mmol) were dissolved in dichloromethane (2 mL). The reaction solution was stirred at room temperature for 12 hours, and concentrated to dryness by rotary evaporation to remove the solvent. The resulting crude product was purified by preparative HPLC to obtain N-(3-(2-(4-(2,3-dichlorophenyl)piperazin-1-yl)ethyl)cyclobutyl)cyclopropanesulfonamide (15 mg, yield: 31.6%).

$^1$H NMR (400 MHz, $CDCl_3$) δ 7.20-7.10 (m, 2H), 7.00-6.92 (m, 1H), 4.75-4.60 (m, 1H), 4.14-3.73 (m, 1H), 3.09 (s, 4H), 2.67 (s, 4H), 2.62-2.49 (m, 2H), 2.42-2.29 (m, 3H), 2.25-1.89 (m, 5H), 1.79-1.54 (m, 4H), 1.16 (d, J=4.8 Hz, 2H), 0.99 (q, J=6.8 Hz, 2H).

MS m/z (ESI): 432.0 $[M+H]^+$.

Example 19

3-(3-(2-(4-(Benzo[b]thiophen-4-yl)piperazin-1-yl)ethyl)cyclobutyl)-1-ethyl-1-methylurea

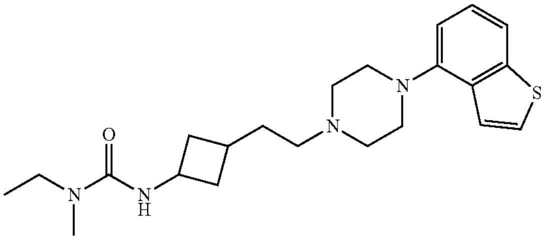 [SMILES: CCN(C)C(=O)NC1CC(CCN2CCN(c3cccc4sccc34)CC2)C1]

In accordance with Example 6, 1-(benzo[b]thiophen-4-yl)piperazine was used as the starting material, accordingly, 3-(3-(2-(4-(benzo[b]thiophen-4-yl)piperazin-1-yl)ethyl)cyclobutyl)-1-ethyl-1-methylurea was obtained.

$^1$H NMR (400 MHz, Chloroform-d) δ 7.55 (d, J=8.0 Hz, 1H), 7.40 (d, J=3.7 Hz, 2H), 7.31-7.26 (m, 1H), 6.90 (d, J=7.6 Hz, 1H), 4.54-4.09 (m, 2H), 3.41-3.15 (m, 6H), 2.85 (d, J=4.0 Hz, 3H), 2.82-2.63 (m, 4H), 2.59-2.51 (m, 1H), 2.48-2.35 (m, 2H), 2.28-2.07 (m, 1H), 2.07-1.87 (m, 2H), 1.85-1.62 (m, 2H), 1.53-1.40 (m, 1H), 1.22-1.02 (m, 3H).

MS m/z (ESI): 401.2 $[M+H]^+$.

Example 20

N-(3-(2-(4-(2,3-Dichlorophenyl)piperazin-1-yl)ethyl)cyclobutyl)oxazole-2-carboxamide

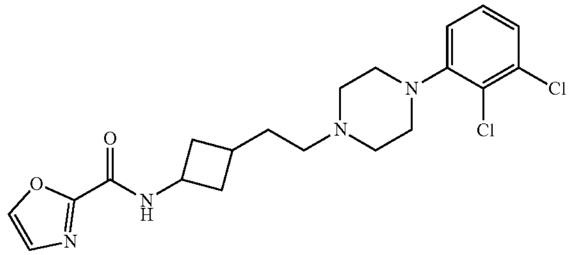 [SMILES: O=C(NC1CC(CCN2CCN(c3cccc(Cl)c3Cl)CC2)C1)c1ncco1]

In accordance with Step 1 of Example 3, N-(3-(2-(4-(2,3-dichlorophenyl)piperazin-1-yl)ethyl)cyclobutyl)oxazole-2-carboxamide (white solid, yield: 26%) was obtained.

The compound of Example 20 can also be obtained by the following method:

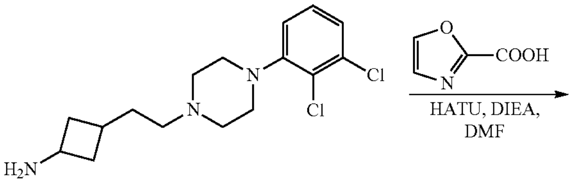

-continued

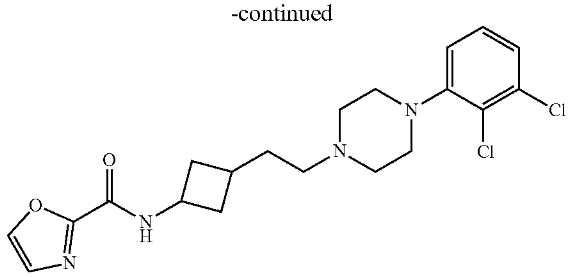

3-(2-(4-(2,3-Dichlorophenyl)piperazin-1-yl)ethyl)cyclobutan-1-amine (50 mg, 0.15 mmol) was dissolved in N,N-dimethylformamide (3 mL) at room temperature, followed by the addition of oxazole-2-carboxylic acid (20 mg, 0.18 mmol), HATU (86 mg, 0.23 mmol) and diisopropylethylamine (58 mg, 0.45 mmol). The reaction solution was stirred at room temperature overnight, and concentrated to dryness by rotary evaporation. The resulting crude product was purified by high performance liquid chromatography to obtain N-(3-(2-(4-(2,3-dichlorophenyl)piperazin-1-yl)ethyl)cyclobutyl)oxazole-2-carboxamide (13 mg, white solid, yield: 21%).

$^1$H NMR (400 MHz, Chloroform-d) δ 7.79 (d, J=1.9 Hz, 1H), 7.24-7.14 (m, 4H), 6.98 (m, 2.0 Hz, 1H), 4.68-4.59 (m, 0.3H), 4.48-4.38 (m, 0.7H), 3.26-3.15 (m, 4H), 2.98-2.81 (m, 4H), 2.64-2.56 (m, 2H), 2.22 (t, J=7.0 Hz, 2H), 2.07-1.99 (m, 1H), 1.89-1.80 (m, 2H), 1.75-1.67 (m, 2H).

MS m/z (ESI): 423.1M+H]$^+$.

Example 20A and Example 20B

N-(Trans-3-(2-(4-(2,3-dichlorophenyl)piperazin-1-yl)ethyl)cyclobutyl)oxazole-2-carboxamide (20A)

N-(Cis-3-(2-(4-(2,3-dichlorophenyl)piperazin-1-yl)ethyl)cyclobutyl)oxazole-2-carboxamide (20B)

20A

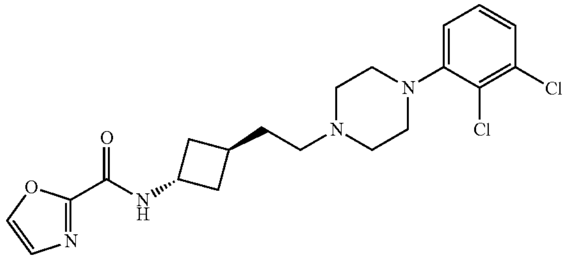

20B

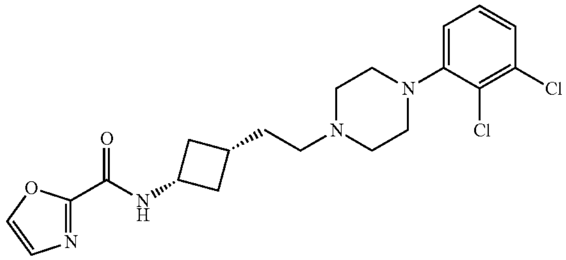

The compound of Example 20 was resolved to obtain N-(trans-3-(2-(4-(2,3-dichlorophenyl)piperazin-1-yl)ethyl)

cyclobutyl)oxazole-2-carboxamide (20A) and N-(cis-3-(2-(4-(2,3-dichlorophenyl)piperazin-1-yl)ethyl)cyclobutyl) oxazole-2-carboxamide (20B), the mass ratio of 20A to 20B was about 1:2.

Chiral Preparation Conditions:

| | |
|---|---|
| Instrument | SFC-80 (Thar, Waters |
| Column type | AD 20*250 mm, 10 um (Daicel) |
| Column pressure | 100 bar |
| Mobile phase | $CO_2$/EtOH(1% Methanol Ammonia) = 50/50 |
| Flow rate | 80 g/min |
| Detection wavelength | UV 214 nm |
| Column temperature | 35° C. |

Example 20A: $T_R$=2.473 Min $^1$H NMR (400 MHz, Chloroform-d) δ 7.79 (s, 1H), 7.24-7.20 (m, 2H), 7.17-7.11 (m, 2H), 6.97 (dd, J=6.4, 3.1 Hz, 1H), 4.69-4.58 (m, 1H), 3.16-3.02 (m, 4H), 2.76-2.58 (m, 4H), 2.41-2.36 (m, 2H), 2.36-2.28 (m, 1H), 2.24-2.17 (m, 4H), 1.82-1.73 (m, 2H).

MS m/z (ESI): 423.1M+H]$^+$.

Example 20B: $T_R$=1.782 Min $^1$H NMR (400 MHz, Chloroform-d) δ 7.79 (s, 1H), 7.22 (s, 1H), 7.19-7.10 (m, 3H), 6.97 (dd, J=7.0, 2.5 Hz, 1H), 4.49-4.37 (m, 1H), 3.28-3.03 (m, 4H), 2.84-2.67 (m, 4H), 2.67-2.54 (m, 2H), 2.53-2.35 (m, 2H), 2.15-2.02 (m, 1H), 1.75-1.63 (m, 4H).

MS m/z (ESI): 423.1M+H]$^+$.

Example 21

N-(3-(2-(4-(2,3-Dichlorophenyl)piperazin-1-yl) ethyl)cyclobutyl)-4-methylisoxazole-5-carboxamide

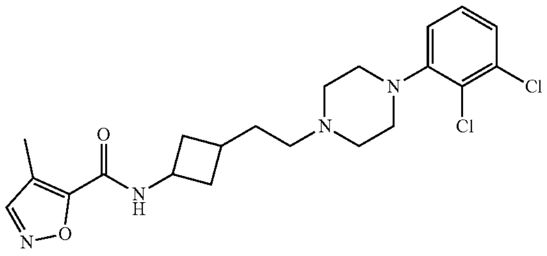 [SMILES: Cc1cnoc1C(=O)NC1CC(CCN2CCN(c3cccc(Cl)c3Cl)CC2)C1]

In accordance with Example 5, N-(3-(2-(4-(2,3-dichlorophenyl)piperazin-1-yl)ethyl)cyclobutyl)-4-methylisoxazole-5-carboxamide was obtained.

$^1$H NMR (400 MHz, Chloroform-d) δ 8.16 (s, 1H), 7.23-7.09 (m, 2H), 7.05-6.91 (m, 1H), 6.75-6.51 (m, 1H), 4.70-4.33 (m, 1H), 3.41-3.00 (m, 4H), 2.90-2.54 (m, 4H), 2.54-2.40 (m, 2H), 2.34 (s, 3H), 2.26-2.02 (m, 3H), 1.91-1.58 (m, 4H).

MS m/z (ESI): 437.1[M+H]$^+$.

Example 21A

N-(Trans-3-(2-(4-(2,3-dichlorophenyl)piperazin-1-yl)ethyl)cyclobutyl)-4-methylisoxazole-5-carboxamide

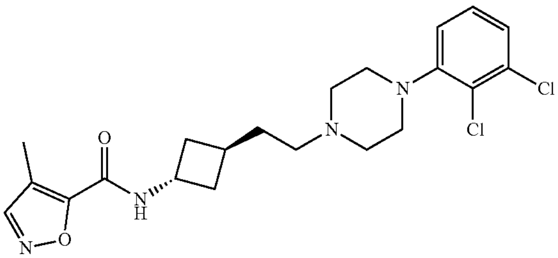

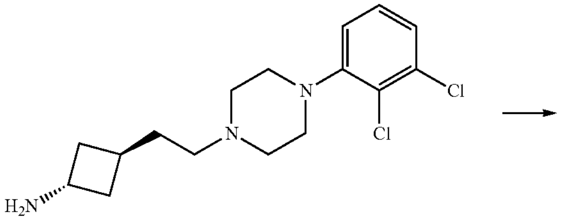

2-1

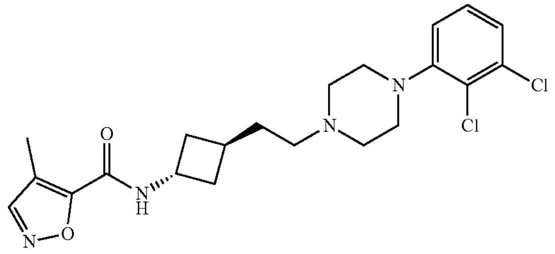

In accordance with the reaction conditions of Example 5, the intermediate 2-1 was used as the starting material, accordingly, N-(trans-3-(2-(4-(2,3-dichlorophenyl)piperazin-1-yl)ethyl)cyclobutyl)-4-methylisoxazol e-5-carboxamide (21A) (21 mg, white solid, yield: 25%) was obtained.

$^1$H NMR (400 MHz, Chloroform-d) δ 8.17 (s, 1H), 7.22-7.09 (m, 2H), 7.02-6.90 (m, 1H), 6.71 (d, J=7.5 Hz, 1H), 4.69-4.54 (m, 1H), 3.30-3.00 (m, 4H), 2.86-2.58 (m, 4H), 2.53-2.39 (m, 2H), 2.34 (s, 3H), 2.33-2.27 (m, 1H), 2.26-2.12 (m, 4H), 1.91-1.72 (m, 2H).

MS m/z (ESI): 437.1[M+H]$^+$.

Example 21B

N-(Cis-3-(2-(4-(2,3-dichlorophenyl)piperazin-1-yl) ethyl)cyclobutyl)-4-methylisoxazole-5-carboxamide

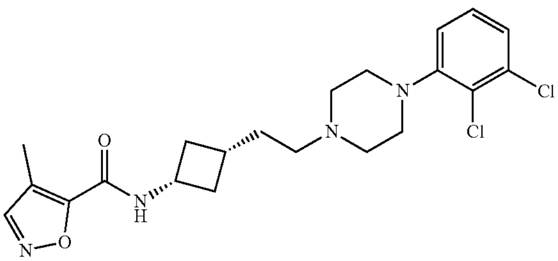

-continued

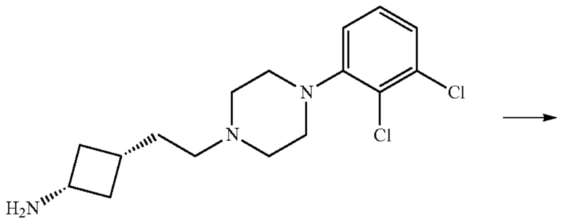

2-2

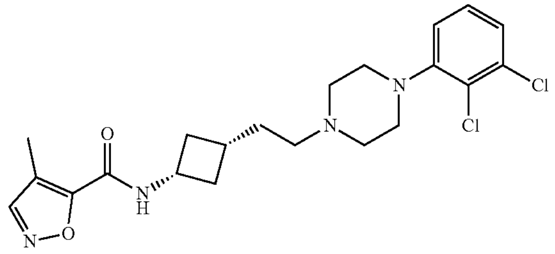

In accordance with the reaction conditions of Example 5, the intermediate 2-2 was used as the starting material, accordingly, N-(cis-3-(2-(4-(2,3-dichlorophenyl)piperazin-1-yl)ethyl)cyclobutyl)-4-methylisoxazole-5-carboxamide (21B) was obtained.

MS m/z (ESI): 437.1[M+H]$^+$.

Example 22

N-(3-(2-(4-(2,3-Dichlorophenyl)piperazin-1-yl)ethyl)cyclobutyl)-3-methylisoxazole-5-carboxamide

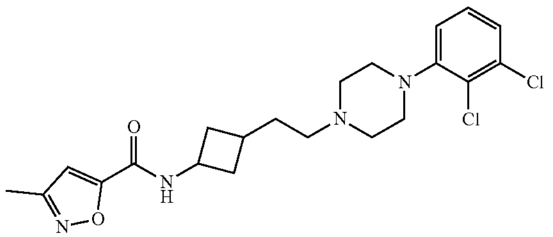 [SMILES: Cc1cc(C(=O)NC2CC(CCN3CCN(c4cccc(Cl)c4Cl)CC3)C2)on1]

In accordance with Example 5, N-(3-(2-(4-(2,3-dichlorophenyl)piperazin-1-yl)ethyl)cyclobutyl)-3-methylisoxazole-5-carboxamide (21 mg, white solid, yield: 32%) was obtained.

$^1$H NMR (400 MHz, Chloroform-d) δ 7.21-7.11 (m, 2H), 7.02-6.93 (m, 1H), 6.77-6.57 (m, 2H), 4.69-4.33 (m, 1H), 3.30-3.01 (m, 4H), 2.89-2.56 (m, 5H), 2.49-2.38 (m, 2H), 2.36 (s, 3H), 2.27-2.15 (m, 1H), 2.10-1.99 (m, 1H), 1.87-1.57 (m, 4H).

MS m/z (ESI): 437.0 [M+H]$^+$.

Example 23

N-(3-(2-(4-(2,3-Dichlorophenyl)piperazin-1-yl)ethyl)cyclobutyl)isoxazole-5-carboxamide

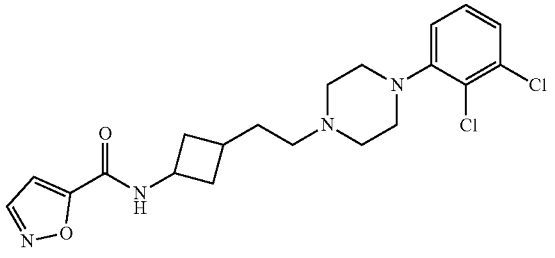 [SMILES: O=C(NC1CC(CCN2CCN(c3cccc(Cl)c3Cl)CC2)C1)c1ccno1]

In accordance with Example 5, N-(3-(2-(4-(2,3-dichlorophenyl)piperazin-1-yl)ethyl)cyclobutyl)isoxazole-5-carboxamide (14 mg, white solid, yield: 22%) was obtained.

$^1$H NMR (400 MHz, Chloroform-d) δ 8.46 (d, J=1.6 Hz, 1H), 7.21-7.11 (m, 2H), 7.06-6.87 (m, 2H), 6.84-6.77 (m, 1H), 4.70-4.34 (m, 1H), 3.24-3.01 (m, 4H), 2.76-2.57 (m, 5H), 2.46-2.35 (m, 2H), 2.34-2.14 (m, 2H), 2.11-1.99 (m, 1H), 1.83-1.59 (m, 3H).

MS m/z (ESI): 423.0 [M+H]$^+$.

Example 23A

N-(Trans-3-(2-(4-(2,3-dichlorophenyl)piperazin-1-yl)ethyl)cyclobutyl)isoxazole-5-carboxamide

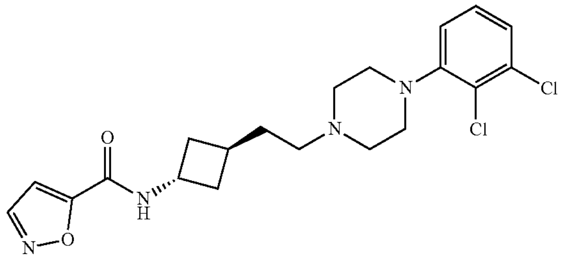

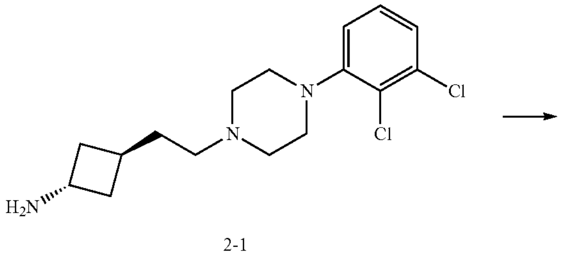

2-1

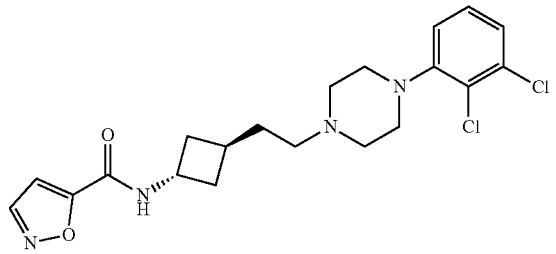

In accordance with the reaction conditions of Example 5, the intermediate 2-1 was used as the starting material, accordingly, N-(trans-3-(2-(4-(2,3-dichlorophenyl)piperazin-1-yl)ethyl)cyclobutyl)isoxazole-5-carboxamide (23A) (white solid) was obtained.

$^1$H NMR (400 MHz, Chloroform-d) δ 8.34 (d, J=1.8 Hz, 1H), 7.22-7.11 (m, 2H), 6.98 (dd, J=6.7, 2.9 Hz, 1H), 6.91 (d, J=1.9 Hz, 1H), 6.78 (d, J=7.6 Hz, 1H), 4.70-4.57 (m, 1H), 3.28-3.02 (m, 4H), 2.86-2.56 (m, 4H), 2.50-2.39 (m, 2H), 2.39-2.30 (m, 1H), 2.28-2.14 (m, 4H), 1.88-1.76 (m, 2H).

MS m/z (ESI): 423.2 [M+H]$^+$.

Example 24

N-(3-(2-(4-(2,3-Dichlorophenyl)piperazin-1-yl)ethyl)cyclobutyl)-2-methyloxazole-5-carboxamide

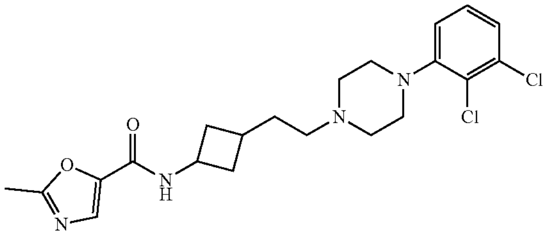 [SMILES: Cc1ncc(C(=O)NC2CC(CCN3CCN(c4cccc(Cl)c4Cl)CC3)C2)o1]

In accordance with Example 5, N-(3-(2-(4-(2,3-dichlorophenyl)piperazin-1-yl)ethyl)cyclobutyl)-2-methyloxazole-5-carboxamide was obtained.

$^1$H NMR (400 MHz, $CDCl_3$) δ 7.55 (s, 1H), 7.16 (dd, J=7.2, 4.3 Hz, 2H), 6.96 (dd, J=6.6, 2.8 Hz, 1H), 6.28 (d, J=7.7 Hz, 1H), 4.47-4.32 (m, 1H), 3.09 (s, 4H), 2.68-2.58 (m, 7H), 2.41-2.33 (m, 2H), 2.18 (td, J=20.3, 12.2 Hz, 2H), 2.02 (dd, J=15.7, 8.3 Hz, 1H), 1.78 (dd, J=15.3, 7.6 Hz, 1H), 1.71-1.55 (m, 3H).

MS m/z (ESI): 437.1 [M+H]$^+$.

Example 25

N-(3-(2-(4-(2,3-Dichlorophenyl)piperazin-1-yl)ethyl)cyclobutyl)isoxazole-3-carboxamide

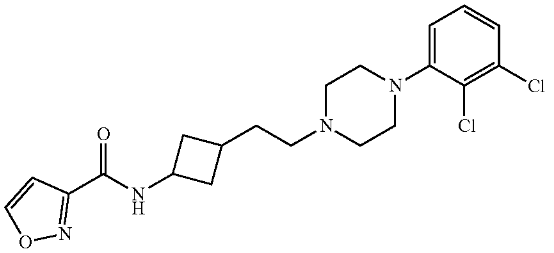 [SMILES: O=C(NC1CC(CCN2CCN(c3cccc(Cl)c3Cl)CC2)C1)c1ccon1]

In accordance with Example 5, N-(3-(2-(4-(2,3-dichlorophenyl)piperazin-1-yl)ethyl)cyclobutyl)isoxazole-3-carboxamide was obtained.

$^1$H NMR (400 MHz, $CDCl_3$) δ 8.33 (d, J=1.7 Hz, 1H), 7.19-7.14 (m, 2H), 7.02-6.93 (m, 1H), 6.91 (d, J=1.6 Hz, 1H), 4.48-4.64 (m, 1H), 3.29-3.11 (m, 4H), 2.79-2.60 (m, 4H), 2.45-2.39 (m, 2H), 2.26-2.22 (m, 2H), 2.05-2.01 (m, 1H), 1.76-1.60 (m, 4H).

MS m/z (ESI): 423.1 [M+H]$^+$.

Example 25A

N-(Trans-3-(2-(4-(2,3-dichlorophenyl)piperazin-1-yl)ethyl)cyclobutyl)isoxazole-3-carboxamide

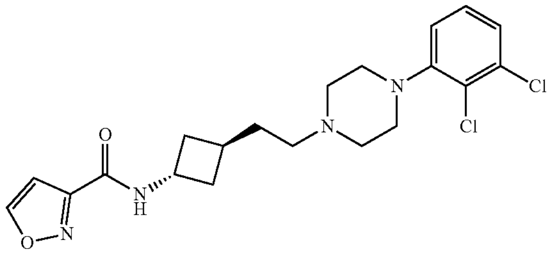 [SMILES: O=C(N[C@H]1C[C@H](CCN2CCN(c3cccc(Cl)c3Cl)CC2)C1)c1ccon1]

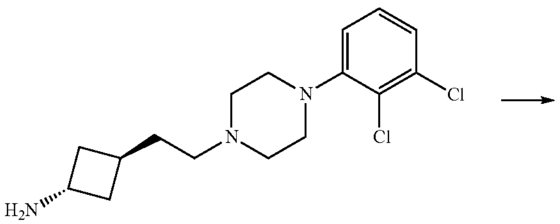

2-1

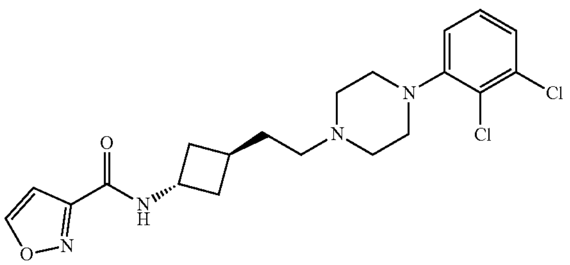

In accordance with the reaction conditions of Example 5, the intermediate 2-1 was used as the starting material, accordingly, N-(trans-3-(2-(4-(2,3-dichlorophenyl)piperazin-1-yl)ethyl)cyclobutyl)isoxazole-3-carboxamide was obtained.

$^1$H NMR (400 MHz, $CDCl_3$) δ 8.46 (d, J=1.4 Hz, 1H), 7.22-7.17 (m, 2H), 7.00 (d, J=6.8 Hz, 2H), 6.81 (d, J=1.4 Hz, 1H), 4.64 (dd, J=15.1, 7.5 Hz, 1H), 3.29 (s, 4H), 2.79-2.77 (m, 4H), 2.36 (s, 2H), 2.24 (d, J=7.0 Hz, 2H), 2.01 (s, 1H), 1.60 (s, 4H).

MS m/z (ESI): 423.1 [M+H]$^+$.

Example 26

N-(3-(2-(4-(2,3-Dichlorophenyl)piperazin-1-yl)ethyl)cyclobutyl)-2-methyloxazole-4-carboxamide

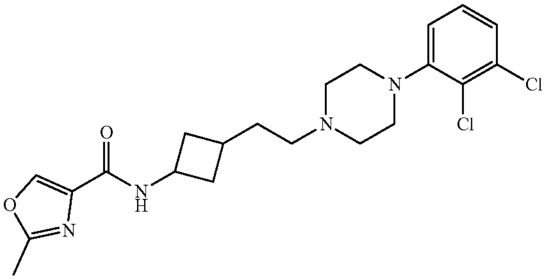 [SMILES: Cc1nc(C(=O)NC2CC(CCN3CCN(c4cccc(Cl)c4Cl)CC3)C2)co1]

In accordance with Example 5, N-(3-(2-(4-(2,3-dichlorophenyl)piperazin-1-yl)ethyl)cyclobutyl)-2-methyloxazole-4-carboxamide (white solid) was obtained.

$^1$H NMR (400 MHz, Chloroform-d) δ 8.06 (d, J=1.6 Hz, 1H), 7.17-7.13 (m, 2H), 7.05-6.90 (m, 2H), 4.66-4.36 (m, 1H), 3.19-3.05 (m, 4H), 2.74-2.63 (m, 3H), 2.64-2.53 (m, 2H), 2.50-2.46 (m, 3H), 2.42-2.34 (m, 2H), 2.21-2.13 (m, 1H), 2.08-1.94 (m, 1H), 1.68-1.60 (m, 4H).

MS m/z (ESI): 437.1M+H]$^+$.

Example 26A

N-(Trans-3-(2-(4-(2,3-dichlorophenyl)piperazin-1-yl)ethyl)cyclobutyl)-2-methyloxazole-4-carboxamide

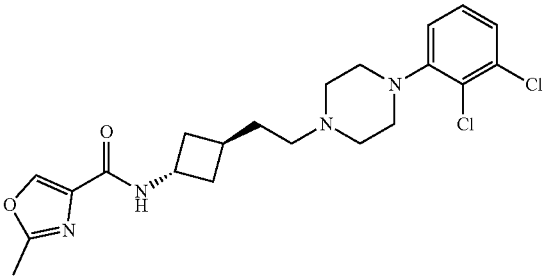 [SMILES: Cc1nc(C(=O)N[C@H]2C[C@H](CCN3CCN(c4cccc(Cl)c4Cl)CC3)C2)co1]

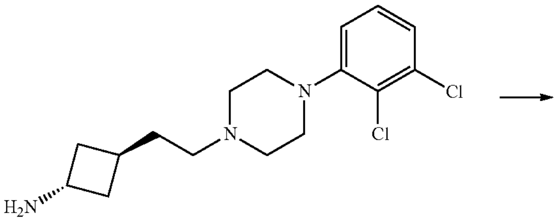

1-1

-continued

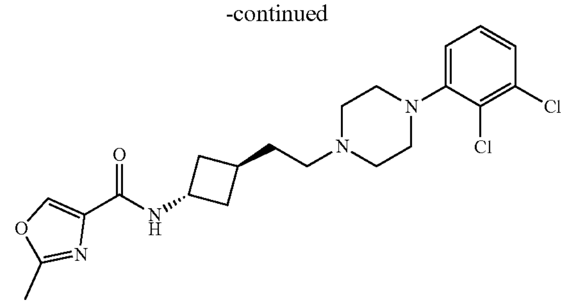

In accordance with the reaction conditions of Example 5, the intermediate 2-1 was used as the starting material, accordingly, N-(trans-3-(2-(4-(2,3-dichlorophenyl)piperazin-1-yl)ethyl)cyclobutyl)-2-methyloxazole-4-carboxamide was obtained.

$^1$H NMR (400 MHz, Chloroform-d) δ 8.06 (s, 1H), 7.20-7.11 (m, 2H), 7.05-6.92 (m, 2H), 4.67-4.54 (m, 1H), 3.19-3.06 (m, 4H), 2.76-2.63 (m, 4H), 2.48 (s, 3H), 2.44-2.41 (m, 2H), 2.21-2.11 (m, 5H), 1.84-1.75 (m, 2H).

MS m/z (ESI): 437.1M+H]$^+$.

Example 27

N-(3-(2-(4-(2,3-Dichlorophenyl)piperazin-1-yl)ethyl)cyclobutyl)quinoline-5-carboxamide

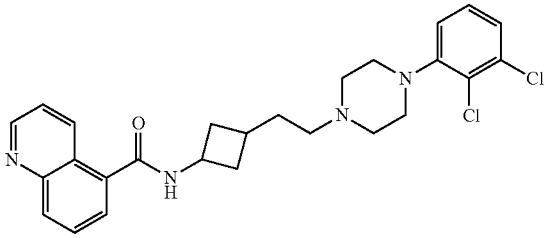 [SMILES: O=C(NC1CC(CCN2CCN(c3cccc(Cl)c3Cl)CC2)C1)c1cccc2ncccc12]

In accordance with Step 1 of Example 5, N-(3-(2-(4-(2,3-dichlorophenyl)piperazin-1-yl)ethyl)cyclobutyl)quinoline-5-carboxamide (35 mg, white solid) was obtained.

$^1$H NMR (400 MHz, Chloroform-d) δ 8.96 (dd, J=4.2, 1.7 Hz, 1H), 8.76 (d, J=8.7 Hz, 1H), 8.25-8.16 (m, 1H), 7.75-7.67 (m, 2H), 7.51-7.45 (m, 1H), 7.16 (dd, J=7.0, 2.0 Hz, 2H), 7.03-6.95 (m, 1H), 6.29-6.15 (m, 1H), 4.84-4.52 (m, 1H), 3.23-3.05 (m, 4H), 2.80-2.67 (m, 4H), 2.52-2.41 (m, 2H), 2.35-2.04 (m, 3H), 1.70-1.57 (m, 4H).

MS m/z (ESI): 483.1M+H]$^+$.

Example 27A

N-(Trans-3-(2-(4-(2,3-dichlorophenyl)piperazin-1-yl)ethyl)cyclobutyl)quinoline-5-carboxamide

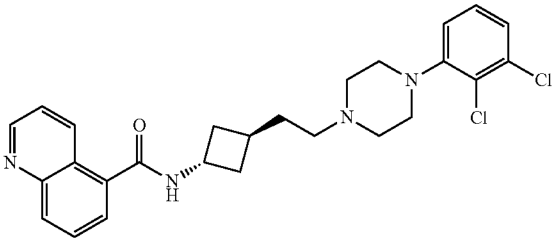

-continued

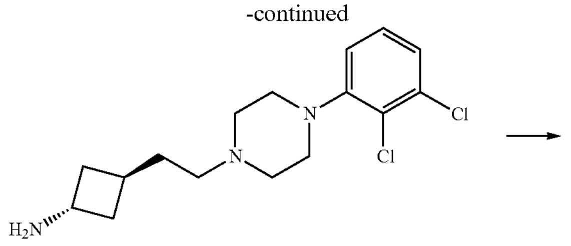

1-1

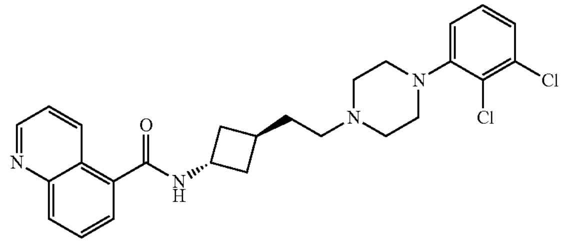

In accordance with the reaction conditions of Example 5, the intermediate 2-1 was used as the starting material, accordingly, N-(trans-3-(2-(4-(2,3-dichlorophenyl)piperazin-1-yl)ethyl)cyclobutyl)quinoline-5-carboxamide was obtained.

$^1$H NMR (400 MHz, Chloroform-d) δ 8.96 (dd, J=4.3, 1.7 Hz, 1H), 8.76 (d, J=8.6 Hz, 1H), 8.25-8.14 (m, 1H), 7.69 (d, J=5.0 Hz, 2H), 7.47 (dd, J=8.6, 4.2 Hz, 1H), 7.19-7.14 (m, 2H), 6.98 (dd, J=7.2, 2.4 Hz, 1H), 6.29 (d, J=7.5 Hz, 1H), 4.84-4.71 (m, 1H), 3.22-3.14 (m, 4H), 2.94-2.88 (m, 1H), 2.86-2.74 (m, 4H), 2.56-2.50 (m, 2H), 2.32-2.26 (m, 2H), 2.25-2.18 (m, 2H), 1.93-1.84 (m, 2H).

MS m/z (ESI): 483.1M+H]$^+$.

Example 28

1-Cyclopropyl-3-(3-(2-(4-(2,3-dichlorophenyl)piperazin-1-yl)ethyl)cyclobutyl)-1-methylurea

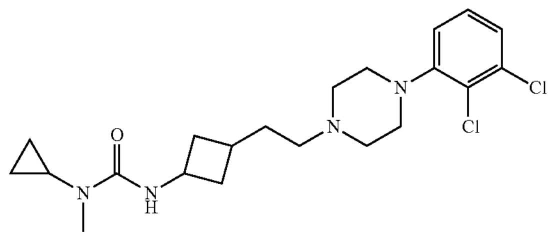 [SMILES: CN(C(=O)NC1CC(CCN2CCN(c3cccc(Cl)c3Cl)CC2)C1)C1CC1]

In accordance with Step 1 of Example 1, 1-cyclopropyl-3-(3-(2-(4-(2,3-dichlorophenyl)piperazin-1-yl)ethyl)cyclobutyl)-1-methyl urea (43 mg, white solid, yield: 33%) was obtained.

$^1$H NMR (400 MHz, Chloroform-d) δ 7.22-7.11 (m, 2H), 7.03-6.92 (m, 1H), 5.32 (dd, J=36.5, 7.6 Hz, 1H), 4.45-4.10 (m, 1H), 3.25-3.02 (m, 4H), 2.88 (d, J=1.7 Hz, 3H), 2.82-2.57 (m, 4H), 2.57-2.51 (m, 1H), 2.47-2.32 (m, 3H), 2.24-2.10 (m, 1H), 2.08-1.90 (m, 1H), 2.06-1.75 (m, 2H), 1.50-1.39 (m, 1H), 0.88-0.78 (m, 2H), 0.75-0.67 (m, 2H).

MS m/z (ESI): 425.1 [M+H]$^+$.

Example 29

1-Cyano-N-(3-(2-(4-(2,3-dichlorophenyl)piperazin-1-yl)ethyl)cyclobutyl)cyclopropane-1-carboxamide

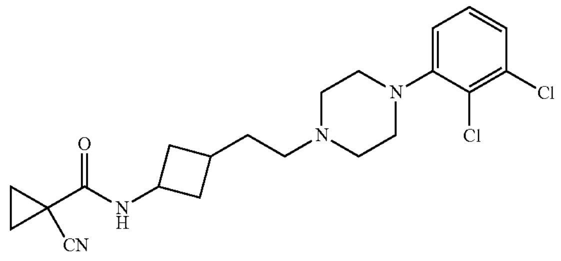 [SMILES: N#CC1(C(=O)NC2CC(CCN3CCN(c4cccc(Cl)c4Cl)CC3)C2)CC1]

In accordance with Step 1 of Example 5, 1-cyano-N-(3-(2-(4-(2,3-dichlorophenyl)piperazin-1-yl)ethyl)cyclobutyl) cyclopropane-1-carboxamide (31 mg, white solid) was obtained.

$^1$H NMR (400 MHz, Chloroform-d) δ 7.19-7.12 (m, 2H), 7.00-6.94 (m, 1H), 6.56-6.36 (m, 1H), 4.54-4.17 (m, 1H), 3.21-3.02 (m, 4H), 2.79-2.60 (m, 4H), 2.57-2.53 (m, 1H), 2.43-2.36 (m, 2H), 2.18-2.12 (m, 1H), 2.06-1.95 (m, 1H), 1.68-1.65 (m, 3H), 1.63-1.56 (m, 3H), 1.51-1.45 (m, 2H).

MS m/z (ESI): 421.1M+H]$^+$.

Example 30

(R)—N-(3-(2-(4-(2,3-Dichlorophenyl)-3-methylpiperazin-1-yl)ethyl)cyclobutyl)-2-hydroxy-2-methylpropanamide

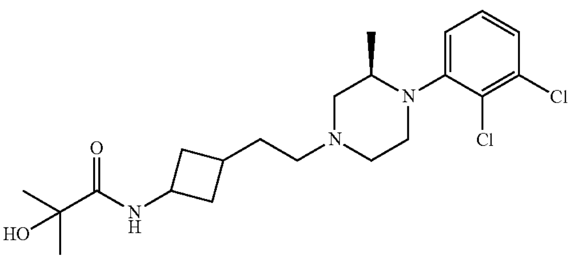 [SMILES: C[C@@H]1CN(CCC2CC(NC(=O)C(C)(C)O)C2)CCN1c1cccc(Cl)c1Cl]

Step 1: Tert-butyl (R)-4-(2,3-dichlorophenyl)-3-methylpiperazine-1-carboxylate

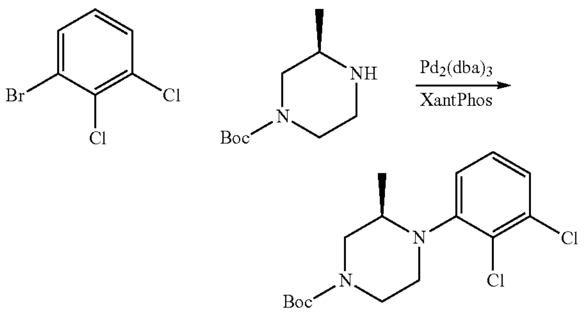

In accordance with Step 1 of Example 2, 1-bromo-2,3-dichlorobenzene and tert-butyl (R)-3-methylpiperazine-1- carboxylate were used as the starting materials, accordingly, tert-butyl (R)-4-(2,3-dichlorophenyl)-3-methylpiperazine-1-carboxylate (600 mg, yellow solid, yield: 32.6%) was obtained.

$^1$H NMR (400 MHz, Chloroform-d) δ 7.26-7.21 (m, 1H), 7.21-7.11 (m, 1H), 7.11-6.94 (m, 1H), 3.99-3.00 (m, 7H), 1.49 (s, 9H), 0.91 (d, J=6.3 Hz, 3H).

MS m/z (ESI): 345.1 $[M+H]^+$.

Step 2: (R)-1-(2,3-Dichlorophenyl)-2-methylpiperazine

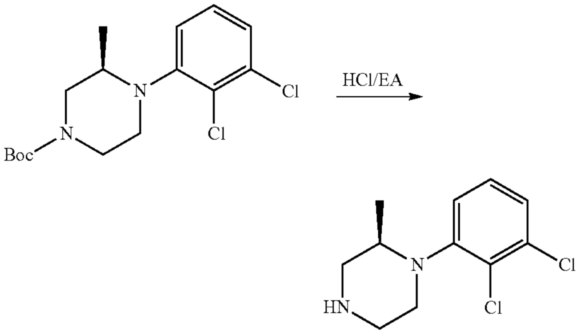

In accordance with Step 2 of Example 2, tert-butyl (R)-4-(2,3-dichlorophenyl)-3-methylpiperazine-1-carboxylate was used as the starting material, accordingly, (R)-1-(2,3-dichlorophenyl)-2-methylpiperazine (420 mg, yellow solid, yield: 98.8%) was obtained.

$^1$H NMR (400 MHz, Methanol-d4) δ 7.36-7.29 (m, 1H), 7.27-7.16 (m, 2H), 3.60-3.44 (m, 1H), 3.42-3.27 (m, 2H), 3.21-3.13 (m, 2H), 3.02-2.81 (m, 2H), 0.88 (d, J=6.3 Hz, 3H).

MS m/z (ESI): 245.1 $[M+H]^+$.

Step 3: (R)-3-(2-(4-(2,3-Dichlorophenyl)-3-methylpiperazin-1-yl)ethyl)cyclobutan-1-amine

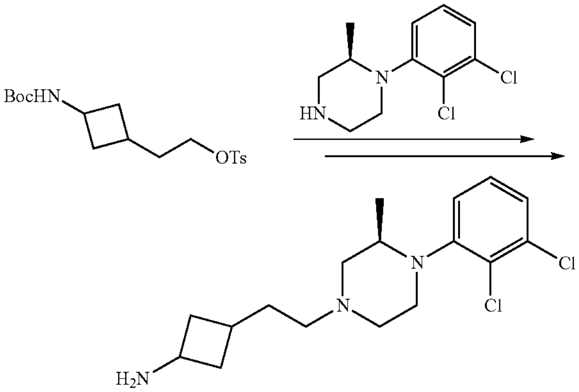

In accordance with Steps 6 and 7 of Example 2, (R)-3-(2-(4-(2,3-dichlorophenyl)-3-methylpiperazin-1-yl)ethyl)cyclobutan-1-amine (280 mg) was obtained.

MS m/z (ESI): 342.1 $[M+H]^+$.

Step 4: (R)—N-(3-(2-(4-(2,3-Dichlorophenyl)-3-methylpiperazin-1-yl)ethyl)cyclobutyl)-2-hydroxy-2-methylpropanamide

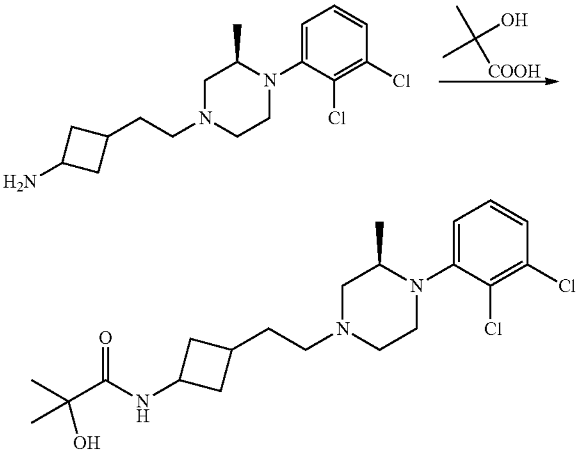

In accordance with Example 5, (R)—N-(3-(2-(4-(2,3-dichlorophenyl)-3-methylpiperazin-1-yl)ethyl)cyclobutyl)-2-hydroxy-2-methylpropanamide (18 mg) was obtained.

$^1$H NMR (400 MHz, Chloroform-d) δ 7.25-7.20 (m, 1H), 7.16 (t, J=7.9 Hz, 1H), 7.10-7.04 (m, 1H), 6.91-6.75 (m, 1H), 4.49-4.14 (m, 1H), 3.47-3.34 (m, 1H), 3.21-3.13 (m, 1H), 2.91-2.82 (m, 1H), 2.83-2.68 (m, 2H), 2.59-2.48 (m, 2H), 2.38-2.31 (m, 2H), 2.24-2.12 (m, 2H), 2.11-1.93 (m, 2H), 1.82-1.73 (m, 1H), 1.70-1.65 (m, 1H), 1.56-1.46 (m, 2H), 1.44 (d, J=2.4 Hz, 6H), 0.90 (d, J=6.2 Hz, 3H).

MS m/z (ESI): 428.1 $[M+H]^+$.

Biological Assay and Evaluation

The present invention is further described below in combination with the following test examples, which are not intended to limit the scope of the present invention.

I. Radioligand-Receptor Binding Assay

Test Example 1. Determination of the Binding Ability of the Compounds of the Present Invention to Dopamine D3 Receptor 1. Experimental Objective:

The objective of this test example is to determine the affinity of the compounds for dopamine D3 receptor.

2.1 Experimental Instruments:

Vortex mixer (IKA; MS3 basic)
Electric heating constant temperature incubator (Shanghai Yiheng Scientific Instruments Co., Ltd; DHP-9032)
Microplate shaker (VWR; 12620-928)
TopCount (PerkinElmer; NTX)
Universal Harvester (PerkinElmer; UNIFILTER-96).

2.2 Experimental Reagents and Consumables:

$[^3H]$-methylspiperone (PerkinElmer; NET856250UC)
Human Dopamine D3 Receptor membrane (PerkinElmer; ES-173-M400UA)
GR 103691 (Sigma; 162408-66-4)
ULTIMA GOLD (Perkin Elmer; 77-16061)
96 round deep well plate 1.1 mL (Perkin Elmer; P-DW-11-C)
UNIFILTER-96 GF/B filter plate (PerkinElmer; 6005174)
Polyethyleneimine
branched (Sigma; 408727)
Centrifuge tubes (BD, 352096; 352070)
Loading slot (JET BIOFIL; LTT001050)

Tray (JET BIOFIL; LTT001050)

Pipette tips (Axygen; T-300-R-S, T-200-Y-R-S, T-1000-B-R-S)

Magnesium chloride (Sigma, 7786-30-3)

Tris-base (Sigma, 77-86-1)

3. Experimental Method:

0.5 to 5 μL of the test compounds (0.005 nM to 100 nM, 10 concentrations in total) and 100 μL of buffer were added to a 96-well assay plate. 0.5 μL of cell membrane and 300 μL of buffer were added to each well. [$^3$H]-methylspiperone was added to the buffer, and the plate was incubated at 27° C. for 30 min. The UNIFILTER-96 GF/B filter plate pre-incubated with 0.5% PEI for 1 h was washed twice with the buffer (1 mL/well). The cell membrane suspension was added to the UNIFILTER-96 GF/B filter plate, washed 4 times, and incubated at 55° C. for 10 min. 40 μL of ULTIMA GOLD was added to each well, and liquid scintillation counting was carried out.

4. Experimental Data Processing Method:

The CPM (Counts per minute) values were determined by TopCount. The percent inhibition rate of [$^3$H]-methylspiperone binding was calculated from the values of the High control (DMSO control) experimental group and Low control (100 nM positive compound) experimental group {% inhibition rate=$(CPM_{sample}-CPM_{low\ control})/(CPM_{high\ control}-CPM_{low\ control})\times 100$}. The 10 concentrations of the compound were from 100 nM to 0.005 nM after 3-fold dilution of the reaction system. The percent inhibition rate and ten-point concentration data were fitted to the parametric nonlinear logistic equation by using GraphPad prism to calculate the $IC_{50}$ values of the compound.

5. Experimental Results:

The binding activity of the compounds of the present invention to D3 was determined by the above assay, and the resulting $IC_{50}$ values are shown in Table 1.

TABLE 1

$IC_{50}$ of the binding activity of the compounds of the present invention to D3

| Example No. | D3 Binding $IC_{50}$ (nM) |
|---|---|
| Cariprazine | 0.89 |
| 7 | 0.79 |
| 11A | 0.95 |
| 13A | 0.75 |
| 13B | 4.37 |
| 14A | 0.44 |
| 18 | 0.62 |
| 19 | 1.13 |
| 20A | 0.37 |
| 20B | 2.54 |
| 21A | 1.36 |
| 22A | 0.34 |
| 23A | 0.31 |
| 24A | 0.33 |
| 25A | 0.30 |
| 26A | 0.42 |
| 27A | 0.40 |
| 28 | 1.99 |
| 30 | 2.78 |

6. Experimental Conclusion:

The compounds of the present invention have good affinity for dopamine receptor D3.

Test Example 2. Determination of the Binding Ability of the Compounds of the Present Invention to 5-HT2A Receptor 1. Experimental Objective:

The objective of this test example is to determine the affinity of the compounds for 5-HT2A receptor.

2.1 Experimental Instruments:

Vortex mixer (IKA; MS3 basic)

Electric heating constant temperature incubator (Shanghai Yiheng Scientific Instruments Co., Ltd; DHP-9032)

Microplate shaker (VWR; 12620-928)

TopCount (PerkinElmer; NTX)

Universal Harvester (PerkinElmer; UNIFILTER-96).

2.2 Experimental Reagents and Consumables:

[$^3$H]-Ketanserin (PerkinElmer NET791)

Human Dopamine 5-HT2A Receptor membrane (PerkinElmer)

GR 103691 (Sigma; 162408-66-4)

ULTIMA GOLD (Perkin Elmer; 77-16061)

96 round deep well plate 1.1 mL (Perkin Elmer; P-DW-11-C)

UNIFILTER-96 GF/B filter plate (PerkinElmer; 6005174)

Polyethyleneimine, branched (Sigma; 408727)

Centrifuge tubes (BD, 352096; 352070)

Loading slot (JET BIOFIL; LTT001050)

Tray (JET BIOFIL; LTT001050)

Pipette tips (Axygen; T-300-R-S, T-200-Y-R-S, T-1000-B-R-S)

Magnesium chloride (Sigma, 7786-30-3)

Tris-base (Sigma, 77-86-1)

3. Experimental Method:

0.5 to 5 μL of the test compounds (0.005 nM to 100 nM, 10 concentrations in total) and 100 μL of buffer were added to a 96-well assay plate. 0.5 μL of cell membrane and 300 μL of buffer were added to each well. [$^3$H]-Ketanserin was added to the buffer, and the plate was incubated at 27° C. for 30 min. The UNIFILTER-96 GF/B filter plate pre-incubated with 0.5% PEI for 1 h was washed twice with the buffer (1 mL/well). The cell membrane suspension was added to the UNIFILTER-96 GF/B filter plate, washed 4 times, and incubated at 55° C. for 10 min. 40 μL of ULTIMA GOLD was added to each well, and liquid scintillation counting was carried out.

4. Experimental Data Processing Method:

The CPM (Counts per minute) values were determined by TopCount. The percent inhibition rate of [$^3$H]-Ketanserin binding was calculated from the values of the High control (DMSO control) experimental group and Low control (100 nM positive compound) experimental group {% inhibition rate=$(CPM_{sample}-CPM_{low\ control})/(CPM_{high\ control}-CPM_{low\ control})\times 100$}. The 10 concentrations of the compound were from 100 nM to 0.005 nM after 3-fold dilution of the reaction system. The percent inhibition rate and ten-point concentration data were fitted to the parametric nonlinear logistic equation by using GraphPad prism to calculate the $IC_{50}$ values of the compound.

5. Experimental Results:

The binding activity of the compounds of the present invention to 5-HT2A was determined by the above assay, and the resulting $IC_{50}$ values are shown in Table 2.

TABLE 2

| IC$_{50}$ of the binding ability of the compounds of the present invention to 5-HT2A | |
|---|---|
| Example No. | 5HT-2A Binding IC$_{50}$ (nM) |
| Cariprazine | 191.28 |
| 7 | 6.35 |
| 11A | 41.5 |
| 13A | 5.77 |
| 13B | 48.45 |
| 14A | 0.79 |
| 18 | 43.97 |
| 19 | 6.39 |
| 20A | 4.19 |
| 20B | 8.73 |
| 21A | 1.81 |
| 22A | 1.35 |
| 23A | 0.98 |
| 24A | 1.80 |
| 25A | 1.92 |
| 26A | 1.37 |
| 27A | 1.89 |
| 28 | 19.08 |
| 30 | 9.63 |

6. Experimental Conclusion:

The above data show that the compounds of the present invention have good affinity for 5-$HT_{2A}$.

II. Cell Function Assay

Test Example 1. Determination of the Effect of the Compounds of the Present Invention on cAMP Content in Cells Stably Expressing D3 Receptors 1. Experimental Objective:

To determine the activation effect of the compounds on D3 receptor.

2.1 Experimental Instruments:

384-well assay plate (Perkin Elmer; 6007680)

96-well conical btm PP Plt nature RNASE/Dnase-free plate (ThermoFisher; 249944)

Pipette (Axygen)

EnVision (Perkin Elmer).

2.2 Experimental Reagents:

Fetal Bovine Serum (Gibco, 10999141)

Ham's F-12K (Kaighn's) Medium (Hyclone; SH30526.01)

Penicillin-Streptomycin, Liquid (Gibco; 15140122)

G418 (invitrogen; 0131-027)

Forskolin (Selleck, S2449)

BSA stabilizer (Perkin Elmer; CR84-100)

cAMP kit (Cisbio; 62AM4PEC)

IBMX (Sigma; 15879)

HEPES (Gibco; 15630080).

3. Experimental Method:

1. Preparation of the buffer: 1*HBSS+20 mM HEPES+0.1% BSA+500 μM IBMX.

Complete medium: Ham's F12K+10% fetal bovine serum+1*penicillin-streptomycin+400 g/mL G418.

2. CHO-D3 cells were cultured in the complete medium at 37° C., 5% C02. After TrypLE digestion, the cells were resuspended in the experimental buffer, and seeded into a 384-well cell culture plate at a seeding density of 8000 cells per well.

3. The experimental buffer (1*HBSS, 0.1% BSA, 20 mM HEPES and 500 μM IBMX) was prepared. The compound was diluted with the buffer. 2.5 μL of the compound solution was added to each well, and the plate was incubated at 37° C. for 10 minutes. The forskolin was diluted to 8 μM (8*) with the experimental buffer. 2.5 μL of the diluted 8*forskolin was added, and the plate was incubated at 37° C. for 30 minutes. cAMP-d2 and Anti-cAMP-$Eu^{3+}$ were thawed, and diluted by 20-fold with the lysis buffer. 10 μL of cAMP-d2 was added to the experimental well, followed by the addition of 10 μL of Anti-cAMP-$Eu^{3+}$. The reaction plate was centrifuged at 200 g for 30 s at room temperature, and left to stand at 25° C. for 1 h. Data was collected using Envision.

4. Experimental Data Processing Method:

1) Z' factor=1−3*(SDMax+SDMin)/(MeanMax−MeanMin);

2) CVMax=(SDMax/MeanMax)*100%;

3) CVMin=(SDMin/MeanMin)*100%;

4) S/B=Singal/Background;

5) EC$_{50}$ of the compound was calculated using the GraphPad nonlinear fitting equation:

$$Y=\text{Bottom}+(\text{Top}-\text{Bottom})/(1+10\hat{}((\text{Log EC}_{50}-X)*\text{HillSlope}))$$

X: log value of compound concentration; Y: Activation %

5. Experimental Results:

TABLE 3

| EC$_{50}$ values of the compounds on cAMP content in cells stably expressing D3 receptors | |
|---|---|
| Example No. | EC$_{50}$ (nM) |
| Cariprazine | 1.7 |
| 8 | 3.5 |
| 9 | 2.2 |
| 10 | 1.2 |
| 11A | 0.4 |
| 12 | 2.4 |
| 13 | 2.9 |
| 13A | 0.6 |
| 14 | 2.8 |
| 14A | 1.0 |
| 17 | 1.2 |
| 19 | 0.9 |
| 20 | 1.7 |
| 20A | 0.6 |
| 20B | 0.7 |
| 21 | 3.4 |
| 21A | 1.1 |
| 22 | 1.2 |
| 22A | 0.9 |
| 23 | 1.7 |
| 23A | 0.7 |
| 24 | 0.7 |
| 24A | 1.7 |
| 25 | 3.1 |
| 25A | 1.1 |
| 26 | 3.9 |
| 26A | 1.4 |
| 27 | 1.0 |
| 27A | 1.6 |
| 28 | 1.0 |
| 29 | 3.3 |
| 30 | 0.4 |

6. Experimental Conclusion:

It can be seen from the data in the table that the compounds of the Examples of the present invention show good agonistic activity in the cAMP content effect assay in cells stably expressing D3 receptors.

Test Example 2. Determination of the Effect of the Compounds of the Present Invention on Calcium Ion Mobility in Cells Stably Expressing 5-HT2A Receptors 1. Experimental Objective:

To determine the inhibitory effect of the compounds on 5-$HT_{2A}$ receptor.

2. Experimental Instruments and Reagents:

2.1 Experimental Instruments:

384-well assay plate (Corning; 3712)
Pipette (Axygen)
FLIPR (Molecular Devices)

2.2 Experimental Reagents:

DMEM (Invitrogen; 11965)
Fetal bovine serum (Biowest; S1810-500)
Dialysis serum (S-FBS-AU-065; Serana)
Penicillin-Streptomycin (Biowest; L0022-100)
Hygromycin B (CABIOCHEM, 400052)
Matrigel (BD; 354230)
DMSO (Sigma; D2650)
HBSS (Invitrogen; 14065)
HEPES (Invitrogen; 15630080)
Probenecid (Sigma; P8761)
BSA (renview; FA016)
TrypLE (ThermoFisher; 12604021).

3. Experimental Method:

1) Preparation of the buffer: 1×HBSS, 20 mM HEPES, 2.5 mM probenecid (probenecid was 400 mM stock in 1 M NaOH), 0.1% BSA. Probenecid and BSA were added fresh on the day of the experiment. Experimental buffers include dye buffer and compound dilution buffer.

2) Cell culture medium: Ham's F-12K+10% fetal bovine serum+600 g/ml hygromycin B+1*penicillin-streptomycin. Seeding medium: Ham's F-12K+10% dialysis serum. Assay buffer: 1×HBSS+20 mM HEPES. Cell line: Flp-In-CHO-5$HT_{2A}$ stable pool.

3) The cells were cultured in the complete medium at 37° C., 5% $CO_2$ to 70%-90% confluency. The cells were digested with TrypLE trypsin, seeded to the 384-well assay plate at a density of $1\times10^4$ cells/well, and incubated for 16 to 24 hours (at least overnight).

4) 20× Component A was thawed to room temperature, diluted to 2× working concentration (containing 5 mM Probenecid) with the assay buffer, and placed at room temperature for later use.

5) The cell culture plate was taken out and left to stand at room temperature for 10 min. FBS was diluted to a concentration of 0.03% with Apricot and the assay buffer, and 20 μL of the solution was finally remained in the 3764 culture plate. 20 μL of 2× Component A (containing 5 mM Probenecid) was added to each experimental well, centrifuged at 200 g and RT for 3 to 5 sec, and incubated at 37° C. for 2 hr.

6) The medium was discarded, and 20 μL of the dye was added. The plate was incubated at 37° C. in the dark for 60 min, and the calcium signal was determined.

7) The antagonist was prepared before the experiment: the working solution of the test compound (6×) was formulated with DMSO. The cell culture plate was taken out and left to stand at room temperature for 10 min. 6× test compound was added to the 384-well assay plate (10 μL/well), which was then incubated at room temperature in the dark for 35 min. The assay plate was transferred to the FLIPR. 10 μL of diluted 5HT was added to each experimental well, followed by the addition of agonist compound at 6× concentration (5 μL/well). The values were determined by the FLIPR and saved. The total assay volume was 30 μL, including 20 μL/well of the dye buffer, 5 μL/well of the test compound at 5× concentration and 5 μL/well of the agonist compound at 6× concentration.

4. Experimental Data Processing Method:

The calcium signal values were determined by FLIPR. The calculated output for each sampling time point in the experiment was the ratio of the 340/510 nm wavelength signals to 380/510 nm wavelength signals. The maximum minus minimum calculation was derived from the ratio signal curve. The percent inhibition rate and ten-point concentration data were fitted to the parametric nonlinear logistic equation by using GraphPad prism to calculate the $IC_{50}$ values of the compound.

5. Experimental Results:

TABLE 4

$IC_{50}$ values of the compounds on calcium ion mobility in cells stably expressing 5-HT2A receptors

| Example No. | $IC_{50}$ (nM) |
|---|---|
| Cariprazine | 551.0 |
| 8 | 8.08 |
| 9 | 16.68 |
| 10 | 48.01 |
| 11A | 38.98 |
| 12 | 22.08 |
| 13 | 13.05 |
| 13A | 3.07 |
| 13B | 38.95 |
| 14 | 6.44 |
| 14A | 2.74 |
| 17 | 8.90 |
| 20 | 5.20 |
| 20A | 2.21 |
| 20B | 11.60 |
| 21 | 10.86 |
| 21A | 11.73 |
| 22 | 13.35 |
| 22A | 4.37 |
| 23 | 8.06 |
| 23A | 3.14 |
| 24 | 5.78 |
| 24A | 4.28 |
| 25 | 8.92 |
| 25A | 20.79 |
| 26 | 6.40 |
| 26A | 6.44 |
| 27 | 7.37 |
| 27A | 7.67 |
| 28 | 11.59 |
| 29 | 33.54 |

6. Experimental Conclusion:

It can be seen from the data in the table that the compounds of the Examples of the present invention show good inhibitory activity in the calcium ion mobility assay in cells stably expressing 5-HT2A receptors.

III. Pharmacokinetic Assay in Balb/c Mice

1. Study Objective:

Balb/c mice were used as test animals. The pharmacokinetic behavior in mouse body (plasma and brain tissue) of the compounds of Examples of the present invention orally administrated at a dose of 5 mg/kg was studied.

2. Experimental Protocol:

2.1 Test Compounds:

Compounds of the Examples of the present invention, prepared by the applicant.

2.2 Test Animals:

Male Balb/c mice (12 mice per group), purchased from Shanghai Jiesijie Laboratory Animal Co., LTD, with Certificate No.: SCXK (Shanghai) 2013-0006 N0.311620400001794.

2.3 Formulation of the Preparation:

The test compound was dissolved in 0.5% CMC-Na (1% Tween80) by sonication to formulate a clear solution or homogeneous suspension.

2.4 Administration:

After an overnight fast, male Balb/c mice (12 mice per group) were administered p.o. with the test compound at an administration dose of 5 mg/kg and an administration volume of 10 mL/kg.

2.5 Sample Collection:

0.2 mL of blood was taken from the heart of the mouse before administration and at 1, 2, 4, 8 and 24 hours after administration, and the mice were sacrificed with $CO_2$. The samples were stored in EDTA-$K_2$ tubes, and centrifuged for 6 minutes at 4° C., 6000 rpm to separate the plasma. The plasma samples were stored at −80° C. Whole brain tissue was taken out, weighed, placed in a 2 mL centrifuge tube, and stored at −80° C.

2.6 Sample Process:

1) 160 μL of acetonitrile was added to 40 μL of the plasma sample for precipitation, and then the mixture was centrifuged for 5 to 20 minutes at 3500×g.

2) 90 μL of acetonitrile containing internal standard (100 ng/mL) was added to 30 L of the plasma and brain homogenate sample for precipitation, and then the mixture was centrifuged for 8 minutes at 13000 rpm.

3) 70 μL of water was added to 70 μL of the treated supernatant and mixed by vortex for 10 minutes. 20 μL of the supernatant was taken to analyze the concentration of the test compound by LC/MS/MS. LC/MS/MS analytical instrument: AB Sciex API 4000 Qtrap.

2.7 Liquid Chromatography Analysis:

Liquid chromatography condition: Shimadzu LC-20AD pump

Chromatographic column: Agilent ZORBAX XDB-C18 (50×2.1 mm, 3.5 m); Mobile phase: Eluent A was 0.1% formic acid in water, and Eluent B was acetonitrile Flow rate: 0.4 mL/min Elution time: 0-4.0 minutes, the eluent is as follows:

| Time/minute | Eluent A | Eluent B |
|---|---|---|
| 0.01 | 90% | 10% |
| 0.5 | 90% | 10% |
| 0.8 | 5% | 95% |
| 2.4 | 5% | 95% |
| 2.5 | 90% | 10% |
| 4.0 | Stop | |

3. Experimental Results and Analysis:

The main parameters of pharmacokinetics were calculated by WinNonlin 6.1. The results of pharmacokinetic test in mice are shown in the following Table 5:

TABLE 5

Experimental results of pharmacokinetic assay in mice

| | Pharmacokinetic test (5 mg/kg) | | | | | |
|---|---|---|---|---|---|---|
| Example No. | Peak time $t_{max}$ (ng/mL) | Plasma concentration $C_{max}$ (ng/ml) | Area under curve $AUC_{0-t}$ (ng/mL × h) | Area under curve AUC0-∞ (ng/mL × h) | Half life $t_{1/2}$ (h) | Average residence time MRT (h) |
| 7 Plasma | 1.0 | 49.7 | 239.5 | 297.3 | 3.25 | 5.1 |
| 7 Brain | 1.0 | 161.9 | 1535.5 | 1653.4 | NA | NA |
| 13 Plasma | 0.5 | 864.7 | 2326.5 | 2462.4 | 1.9 | 2.8 |
| 13 Brain | 1.0 | 464.0 | 1972.6 | NA | NA | NA |
| 13A Plasma | 0.5 | 745.0 | 1423 | 1444.0 | 1.3 | 1.8 |
| 13A Brain | 1.0 | 321.0 | 1081 | NA | NA | NA |
| 13B Plasma | 0.5 | 961.0 | 2250 | 2325.0 | 1.6 | 2.3 |
| 13B Brain | 1.0 | 361.0 | 900 | NA | NA | NA |
| 14 Plasma | 0.5 | 254.0 | 503.0 | 540.9 | 2.1 | 2.8 |
| 14 Brain | 1.0 | 569.3 | 2077.8 | NA | NA | NA |
| 14A Plasma | 1.0 | 102.0 | 395 | 501.0 | 3.7 | 5.3 |
| 14A Brain | 1.0 | 179.0 | 1346 | NA | NA | NA |
| 19 Plasma | 0.5 | 368.7 | 1475.7 | 2001.3 | 3.4 | 5.7 |
| 19 Brain | 1.0 | 338.7 | 2187.7 | 2305.1 | NA | NA |
| 20 Plasma | 0.5 | 391.0 | 1038.9 | 1227.3 | 2.8 | 3.9 |
| 20 Brain | 1.0 | 1196.0 | 4830.1 | 4881.3 | NA | NA |
| 20A Plasma | 0.5 | 673.0 | 1844.0 | 1970.0 | 1.9 | 3.1 |
| 20A Brain | 1.0 | 1763.0 | 8130.0 | NA | NA | NA |
| 20B Plasma | 0.5 | 715.0 | 1624.0 | 1711.0 | 1.8 | 2.4 |
| 20B Brain | 1.0 | 1871.0 | 5204.0 | NA | NA | NA |
| 25A Plasma | 0.5 | 362 | 3049 | 12935 | 5.6 | 6.2 |
| 25A Brain | 1.0 | 1535 | 11878 | NA | NA | NA |
| 27A Plasma | 0.5 | 349.0 | 456 | 471.0 | 1.7 | 1.8 |
| 27A Brain | 1.0 | 372.0 | 1236 | NA | NA | NA |

4. Experimental Conclusion:

It can be seen from the experimental results of pharmacokinetic assay in mice in the table that the compounds of the Examples of the present invention showed good pharmacokinetic properties, both the exposure AUC and maximum plasma concentration $C_{max}$ were good.

IV. Stability Assay in Liver Microsome In Vitro

1. Experimental Objective:

To evaluate the metabolic stability of the compounds of the present invention in liver microsome in vitro.

2. Experimental Instruments:

2.1 Instruments

| Instrument | Brand | Model |
|---|---|---|
| Vortex mixer | IKA | Vortex |
| Thermostatic mixer | SpecificAction | Incubation-micro mixer |
| Centrifuge | Eppendorf | Centrifuge 5804R |
| Liquid chromatograph | Shimadzu | LC-30 AD |
| Mass spectrometer | AB Sciex | API5500 |

2.2 Reagents:

| Reagent | Brand | Article number |
|---|---|---|
| 7-Hydroxycoumarin | J&K Scientific | 153384 |
| DMSO | Sigma | 34869 |
| PBS | Gibco | 10010-023 |
| Human liver microsome | BD | H0610 |
| SD rat liver microsome | Corning | 452501 |
| CD-1 mouse liver microsome | BD | M1000 |
| Dog liver microsome | BD | D1000 |
| NADPH | Bide | BD11658 |
| UDPGA | Sigma | U6751 |
| Avermectin | J&K Scientific | 622045 |

3. Experimental Processes:

3.1. Formulation of the Working Solution of the Compound

Formulation of the working solution of the compound: 2 μL of the stock solution of the compound was added to 998 μL of phosphate buffer, and the final concentration was 20 μM.

Formulation of the working solution of the control compound (7-hydroxycoumarin): The formulation was consistent with that of the compound.

3.2. Formulation of the Working Solution of Liver Microsome 78.1 μL of 20 mg/mL microsome was diluted to 2.5 mL with 100 mM phosphate buffer and mixed well, and the final concentration was 0.625 mg/mL.

3.3. Formulation of NADPH and UDPGA 33.3 mg of NADPH and 25.8 mg of UDPGA were weighed respectively, followed by the addition of 2 mL of 100 mM phosphate buffer. The final concentrations were 20 mM.

3.4. Formulation of the Channel-Forming Reagent (Alamethicin)

1 mg of Alamethicin was weighed, to which 200 μL of DMSO was added to obtain a 5 mg/mL solution. 10 μL of this solution was added to 990 μL of phosphate buffer (pH 7.4), and the final concentration was 50 μg/mL.

3.5. Formulation of the Reaction Stop Solution

Stop solution: Cold acetonitrile containing 100 ng/mL labetalol hydrochloride and 400 ng/mL tolbutamide as internal standards, stored in a refrigerator at 2 to 8° C.

3.6. Incubation Procedure

400 μL of the formulated liver microsome, 25 μL of the working solution of the compound (10 μM) and 25 μL of Alamethicin (50 μg/mL) were added to a 96-well plate successively, which was then pre-incubated at 37° C. for 10 min. 50 μL of the formulated NADPH/UDPGA was added to initiate the reaction, and the plate was incubated at 37° C. The total volume of the reaction system was 500 μL. The final contents of the components are as follows:

| Component | Content |
|---|---|
| Liver microsome | 0.5 mg/mL |
| Compound | 1 μM |
| NADPH | 2 mM |
| UDPGA | 2 mM |
| Alamethicin | 2.5 μg/mL |

50 μL of the sample was taken out at time points of 0 min, 5 min, 10 min, 20 min, 30 min and 60 min respectively, followed by the addition of 200 μL of the cold stop solution containing the internal standards to stop the reaction in the samples. The resulting sample was centrifuged at 4000 g for 10 min, and the supernatant was collected for LC-MS/MS analysis.

4. Experimental Results:

TABLE 6

Stability in liver microsome in vitro

| Species | No. | Half life ($t_{1/2}$) min | Intrinsic clearance rate ($CL_{int}$) (μL/min/mg protein) | Remaining (%, 120 min) |
|---|---|---|---|---|
| Human | Cariprazine | 77.2 | 18 | 34.4 |
| | Example 6 | 76.3 | 45.4 | 61.2 |
| | Example 13 | 93.3 | 37.2 | 63.0 |
| | Example 13A | 138.8 | 10 | 53.3 |
| | Example 15 | 189.4 | 18.3 | 79.5 |
| | Example 20A | 105.9 | 13.1 | 42.8 |
| | Example 25A | 90.1 | 15.4 | 38.8 |
| Rat | Cariprazine | 52.7 | 26.3 | 19.1 |
| | Example 20A | 60 | 23.1 | 25.4 |
| | Example 25A | 60.5 | 22.9 | 27.0 |
| Dog | Cariprazine | 50.1 | 27.7 | 21.4 |
| | Example 20A | 70.6 | 19.6 | 29.2 |
| | Example 25A | 69.5 | 19.9 | 30.2 |

Note:

| Type of clearance rate | Intrinsic clearance rate (μL/min/mg protein) Human | Rat | Dog |
|---|---|---|---|
| Slow | <8.6 | <13.2 | <5.3 |
| Rapid | >47.0 | >71.9 | >28.9 |

5. Experimental Conclusion:

The above data show that the compounds of the Examples of the present invention are moderately metabolized in human, rat and dog liver microsome in vitro.

V. Pharmacodynamic Model of Active Escape Experiment in Rats

1. Experimental Objective:

To evaluate the anti-schizophrenic effect of the compounds using the pharmacodynamic model of the active escape experiment in rats.

2. Experimental Instruments and Reagents:

2.1 Instruments:

| No. | Instrument name | Instrument model | Source | Manufacturer |
|---|---|---|---|---|
| 1 | Active and passive shuttle device | MED-APA-DIR | Imported | Med Associates, Inc. |

-continued

| No. | Instrument name | Instrument model | Source | Manufacturer |
|---|---|---|---|---|
| 2 | Thermostatic magnetic stirrer | 85-2 | Domestic | Shanghai Sile Instrument Co., Ltd. |
| 3 | Vortex mixer | H-101 | Domestic | Shanghai Kanghe Photoelectric Instrument Co., Ltd. |
| 4 | Ultrasonic cleaner | KQ3200DE | Domestic | Kunshan Ultrasonic Instruments Co., Ltd |

2.2 Reagents:

| No. | Name | Purity | Batch number | Storage condition | Manufacturer |
|---|---|---|---|---|---|
| 1 | CMC-Na | 100% | SLBV9664 | RT | Sigma |
| 2 | Tween 80 | 100% | BCBV8843 | RT | Sigma |

2.3 Test Compounds:

Compounds of the Examples of the present invention, prepared by the applicant.

3. Test Animals:

| Species | Strain | Age | Gender | Supplier |
|---|---|---|---|---|
| Rats | F344 | 6-8 weeks | Male | Beijing Vital River Laboratory Animal Technology Co., Ltd. |

4. Formulation of the Vehicle and Compounds:

4.1 Vehicle (0.5% CMC-Na+1% Tween80)

A certain mass (such as 1.0 g) of CMC-Na was weighed into a glass bottle, a certain volume (such as 200 mL) of purified water was added, and the resulting mixture was stirred to disperse evenly. 1% (v/v) Tween 80 was added according to the solution volume, and the resulting mixture was stirred overnight to obtain a homogeneous clear solution, which was stored at 2 to 8° C. for later use.

4.2 Formulation of the Compounds:

A prescription amount of the compound was weighed, followed by the addition of a prescription volume of 0.5% CMC-Na+1% Tween 80 solution. The compound solution was formulated before the administration, stored at 2 to 8° C., and used within 4 days.

The actual sample amount needs to be calculated during the formulation and administration of the compound solution. The calculation equation is as follows: the actual sample amount of the compound=theoretical weighing sample amount*purity/salt coefficient.

5. Experimental Operation:

After arriving at the experimental facility, the animals were acclimatized for one week before starting the experiment.

5.1 Establishment of the Pharmacodynamic Model:

5.1.1 The animal was put into the shuttle box and adapted for 5 seconds, followed by subjecting to 10 seconds of sound and light stimulation;

5.1.2 If the animal avoided to the other side during the 10 seconds of sound and light stimulation, then no electric shock would be given, this would be recorded as avoids, and the single training ended;

5.1.3 If the animal failed to move to the other side after the 10 seconds of sound and light stimulation, then an electric shock would be given, the current intensity was 0.6 mA, the duration was 10 seconds, if the animal avoided to the other side during the 10 seconds of electric shock, then the electric shock would stop, this would be recorded as escapes, and the single training ended;

5.1.4 If the animal failed to avoid during the 10 seconds of electric shock, then the electric shock would stop, this would be recorded as escape failures, and the single training ended;

5.1.5 Each animal was trained 30 times a day for a total of 6 days, and returned to the cage after the training.

5.2 Baseline Test and Grouping

The day before the compound screening test, a baseline test was performed. The test process was the same as 5.1.1 to 5.1.3, and the number of the baseline test was 20. The animals whose number of avoids reached 16 (80%) were grouped according to the number of avoids, 10 animals per group. The first group was administered with the vehicle orally, and the other groups were administered with the corresponding test compounds according to the experimental design.

5.3 Compound Screening Test

The compound was administered orally (5 mL/kg) one hour before the test; The test process was the same as 5.1.1 to 5.1.4, and the number of the test was 20.

6. Data Process:

The following data was collected by the software for data analysis:

Number of avoids of the animal;

Number of escape failures of the animal;

Escape latency of the animal;

All measurement data were expressed as mean±standard error (Mean±SEM), and analyzed by Graphpad 6 statistical software. The difference was considered to be significant when $p<0.05$.

7. Experimental Results:

TABLE 7

| Example No. | CAR value | Dose (mg/kg) |
|---|---|---|
| Vehicle | 91-98% | — |
| 20 | 30% | 1 |
| 20A | 18.5% | 1 |
| 25A | 18% | 1 |

8. Experimental Conclusion:

It can be seen from the above data that the compounds of the Examples of the present invention show good effects in the pharmacodynamic model of the active escape experiment in rats, indicating that they have anti-schizophrenia effect.

What is claimed is:

1. A compound of formula (IX-A), a stereoisomer thereof or a pharmaceutically acceptable salt thereof, (IX-A)

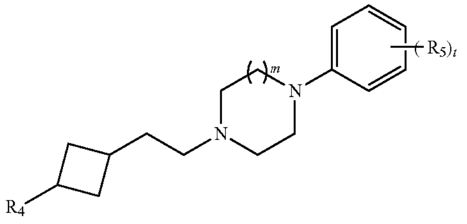

wherein:

$R_4$ is selected from the group consisting of 5 to 6 membered N-containing heterocyclyl,

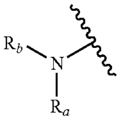 , 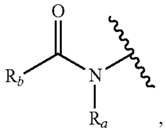 , 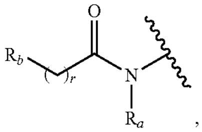 ,

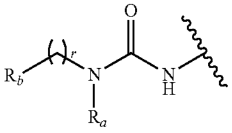 and 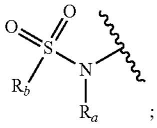 ;

$R_a$ is selected from the group consisting of hydrogen, deuterium, halogen, amino, nitro, hydroxy, cyano, $C_{1-6}$ alkyl, $C_{1-6}$ deuterated alkyl, $C_{1-6}$ haloalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl;

$R_b$ is selected from the group consisting of hydrogen, deuterium, halogen, amino, nitro, hydroxy, cyano, $C_{1-6}$ alkyl, $C_{1-6}$ deuterated alkyl, $C_{1-6}$ haloalkyl, $C_{1-6}$ alkoxy, $C_{1-6}$ hydroxyalkyl, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl, wherein the amino, $C_{1-6}$ alkyl, $C_{1-6}$ deuterated alkyl, $C_{1-6}$ haloalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl are each optionally further substituted by one or more substituents selected from the group consisting of deuterium, halogen, amino, nitro, hydroxy, cyano, $C_{1-6}$ alkyl, $C_{1-6}$ deuterated alkyl, $C_{1-6}$ haloalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl;

$R_5$ is selected from the group consisting of hydrogen, deuterium, $C_{1-6}$ alkyl, $C_{1-6}$ deuterated alkyl, $C_{1-6}$ haloalkyl, $C_{1-6}$ alkoxy, $C_{1-6}$ haloalkoxy, halogen, amino, nitro, hydroxy, cyano, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl;

or, any adjacent two $R_5$ are bonded to form a 5 to 6 membered heterocyclyl or 5 to 6 membered heteroaryl;

r is 0, 1 or 2;

m is 0 or 1; and t is 0, 1, 2 or 3;

when

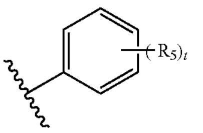 is 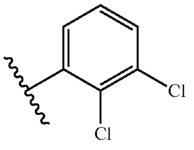

and m is 1, then $R_4$ is not

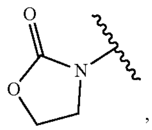 , 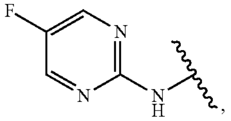 ,

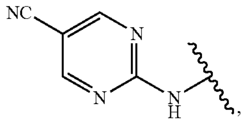 , 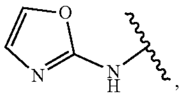 ,

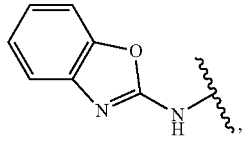 ,

—$NHC(O)C_2H_5$, —$NHC(O)N(CH_3)_2$, —$NHC(O)NHCH_3$, —$NHC(O)N(C_2H_5)CH_3$, —$NHC(O)NHC_2H_5$,

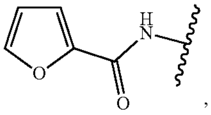 , 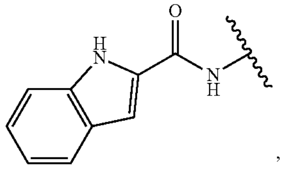 ,

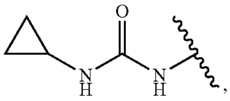 , 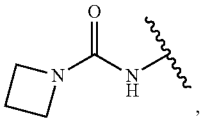 ,

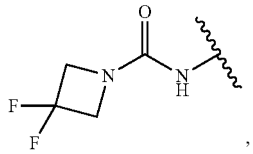 , 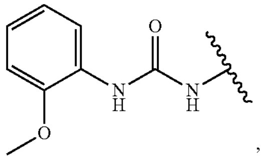 ,

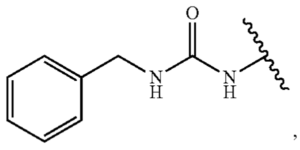 , 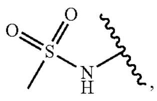 ,

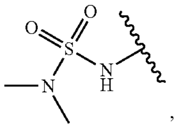 , 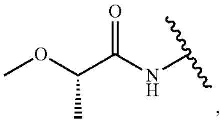 ,

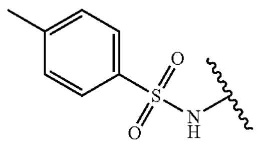 or 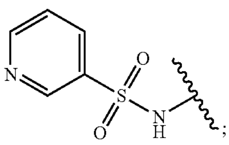 ;

when m is 2, then $R_4$ is not —$NHC(O)N(CH_3)_2$.

2. The compound, the stereoisomer thereof or the pharmaceutically acceptable salt thereof according to claim 1, wherein the compound is further as shown in formula (X) or formula (X-A):

(X)

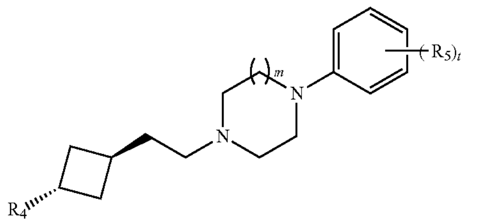

(X-A)

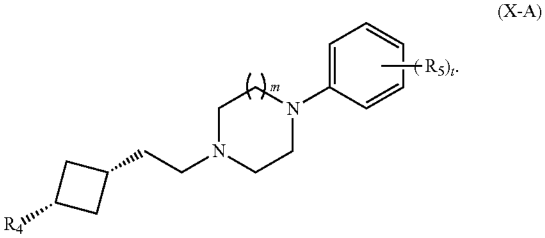

3. The compound, the stereoisomer thereof or the pharmaceutically acceptable salt thereof according to claim 1, wherein $R_4$ is selected from the group consisting of 5 to 6 membered N-containing heterocyclyl,

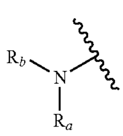,
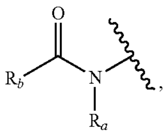,
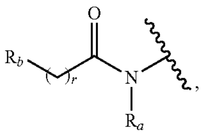,

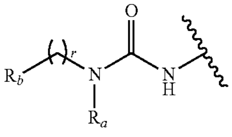
and
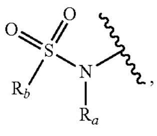, $R_a$ is selected from the group consisting of hydrogen, cyano, halogen, $C_{1-3}$ alkyl, $C_{1-3}$ haloalkyl, $C_{1-3}$ alkoxy and $C_{3-6}$ cycloalkyl;

$R_b$ is selected from the group consisting of amino, $C_{1-3}$ alkyl, $C_{1-3}$ alkoxy, $C_{1-3}$ hydroxyalkyl, $C_{3-6}$ cycloalkyl, 3 to 6 membered heterocyclyl, $C_{6-10}$ aryl and 5 to 10 membered heteroaryl, optionally further substituted by one or more substituents selected from the group consisting of halogen, hydroxy, cyano, $C_{1-3}$ alkyl and $C_{1-3}$ alkoxy; and r is 0, 1 or 2.

4. The compound, the stereoisomer thereof or the pharmaceutically acceptable salt thereof according to claim 1, wherein the compound is further as shown in formula (XI):

(XI)

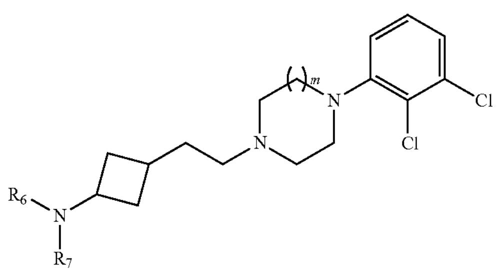

wherein:

$R_6$ is selected from the group consisting of hydrogen, deuterium, $C_{1-6}$ alkyl, $C_{1-6}$ deuterated alkyl, $C_{1-6}$ haloalkyl, $C_{1-5}$ alkoxy, $C_{1-6}$ haloalkoxy, halogen, amino, nitro, hydroxy, cyano, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl;

$R_7$ is selected from the group consisting of hydrogen, deuterium, halogen, amino, nitro, hydroxy, cyano, $C_{1-6}$ alkyl, $C_{1-6}$ deuterated alkyl, $C_{1-6}$ haloalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl, 5 to 12 membered heteroaryl, $R_{ee}$, $—C(O)(CH_2)_{n2}R_{ee}$, $—(CH_2)_{n2}C(O)NR_{ee}R_{ff}$, $—C(O)NR_{ee}R_{ff}$, $—(CH_2)_{n2}C(O)NR_{ee}C(O)R_{ff}$, $—(CH_2)_{n2}S(O)_{n2}R_{ee}$, $—(CH_2)_{n2}NR_{ee}S(O)_{n2}R_{ff}$; $—(CH_2)_{n2}S(O)_{m2}NR_{ee}R_{ff}$, $—(CH_2)_{n1}S(O)_{m2}NR_{ee}R_{ff}$, $—(CH_2)_{n2}OR_{ee}$, $—C(O)NR_{ee}(CH_2)_{n2}R_{ff}$, $—C(O)(CH_2)_{n2}OR_{ee}$, $—(CH_2)_{n2}SR_{ee}$, $—(CH_2)_{n2}C(O)OR_{ee}$, $—P(O)R_{ee}R_{ff}$; $—(CH_2)_{n2}NR_{ee}C(O)R_{ff}$ and $—(CH_2)_{n2}NR_{ee}S(O)_{m2}R_{ff}$, wherein the $C_{1-6}$ alkyl, $C_{1-6}$ deuterated alkyl, $C_{1-6}$ haloalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl are each optionally further substituted by one or more substituents selected from the group consisting of deuterium, halogen, amino, nitro, hydroxy, cyano, $C_{1-6}$ alkyl, $C_{1-6}$ deuterated alkyl, $C_{1-6}$ haloalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl;

$R_{ee}$ and $R_{ff}$ are each independently selected from the group consisting of hydrogen, amino, $C_{1-6}$ alkyl, $C_{1-6}$ haloalkyl, $C_{1-6}$ alkoxy, $C_{3-8}$ cycloalkyl, 3 to 8 membered heterocyclyl, $C_{6-14}$ aryl and 5 to 14 membered heteroaryl, wherein the amino, $C_{1-6}$ alkyl, $C_{1-6}$ haloalkyl, $C_{1-6}$ alkoxy, $C_{3-8}$ cycloalkyl, 3 to 8 membered heterocyclyl, $C_{6-14}$ aryl and 5 to 14 membered heteroaryl are each optionally further substituted by one or more substituents selected from the group consisting of halogen, hydroxy, cyano, oxo, $C_{1-6}$ alkyl, $C_{1-6}$ haloalkyl and $C_{1-6}$ alkoxy;

n2 is selected from the group consisting of 0, 1 and 2;

m2 is selected from the group consisting of 0, 1 and 2; and m is selected from the group consisting of 0, 1 and 2.

5. The compound, the stereoisomer thereof or the pharmaceutically acceptable salt thereof according to claim 4, wherein $R_{ee}$ and $R_{ff}$ are each independently selected from the group consisting of hydrogen and the following substituents:

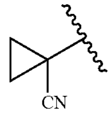, 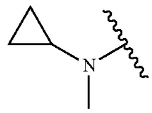, 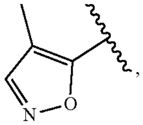,

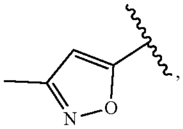, 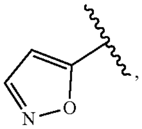, 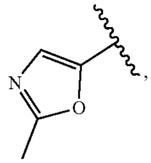,

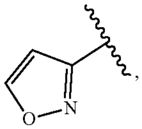, 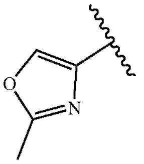 and

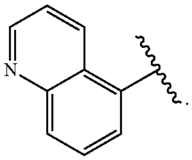.

6. The compound, the stereoisomer thereof or the pharmaceutically acceptable salt thereof according to claim 4, wherein, $R_6$ is selected from the group consisting of hydrogen, deuterium, halogen, amino, nitro, hydroxy, cyano, $C_{1-3}$ alkyl, $C_{1-3}$ deuterated alkyl, $C_{1-3}$ haloalkyl, $C_{1-3}$ alkoxy, $C_{1-3}$ haloalkoxy, $C_{2-3}$ alkenyl and $C_{2-3}$ alkynyl;

$R_7$ is selected from the group consisting of $R_{ee}$, —C(O)$(CH_2)_{n2}R_{ee}$, —C(O)$NR_{ee}R_{ff}$, —C(O)$NR_{ff}(CH_2)_{n2}R_{ee}$, —$S(O)_{m2}R_{ee}$ and —$S(O)_{m2}NR_{ee}R_{ff}$;

$R_{ee}$ is selected from the group consisting of hydrogen, amino, $C_{1-6}$ alkyl, $C_{1-6}$ haloalkyl, $C_{1-6}$ alkoxy, $C_{3-8}$ cycloalkyl, 3 to 8 membered heterocyclyl, $C_{6-14}$ aryl and 5 to 14 membered heteroaryl, wherein the amino, $C_{1-6}$ alkyl, $C_{1-6}$ haloalkyl, $C_{1-6}$ alkoxy, $C_{3-8}$ cycloalkyl, 3 to 8 membered heterocyclyl, $C_{6-14}$ aryl and 5 to 14 membered heteroaryl are each optionally further substituted by one or more substituents selected from the group consisting of halogen, hydroxy, cyano, oxo, $C_{1-6}$ alkyl, $C_{1-6}$ haloalkyl and $C_{1-6}$ alkoxy;

$R_{ff}$ is selected from the group consisting of hydrogen, deuterium, halogen, amino, nitro, hydroxy, cyano, $C_{1-6}$ alkyl, $C_{1-6}$ deuterated alkyl, $C_{1-6}$ haloalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl;

n2 is selected from the group consisting of 0, 1 and 2; and m2 is selected from the group consisting of 0, 1 and 2.

7. The compound, the stereoisomer thereof or the pharmaceutically acceptable salt thereof according to claim 4, wherein the compound is further as shown in formula (XI-A) or formula (XI-B):

(XI-A)

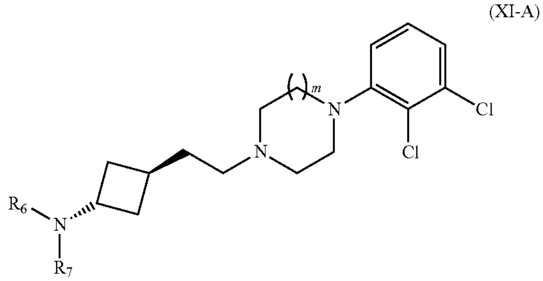

(XI-B)

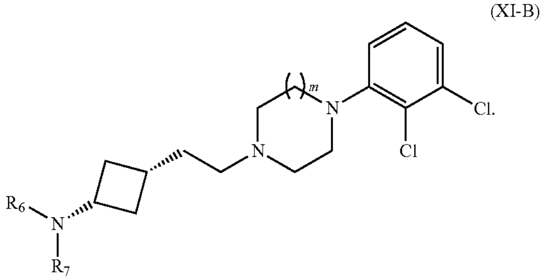.

8. The compound, the stereoisomer thereof or the pharmaceutically acceptable salt thereof according to claim 4, wherein

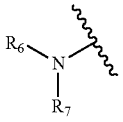

is selected from the group consisting of 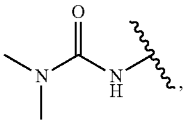, 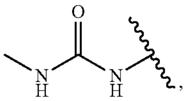,

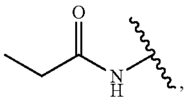, 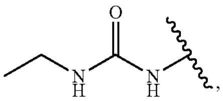,

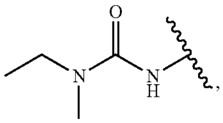, 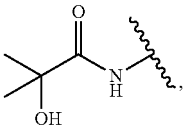,

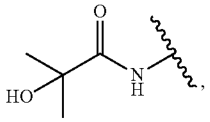, 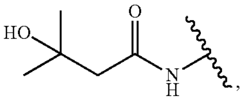,

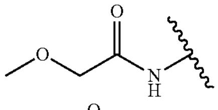, 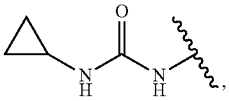,

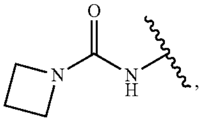, 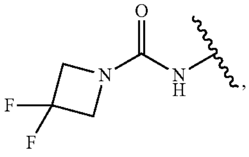,

-continued
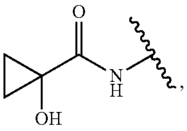,
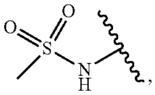,
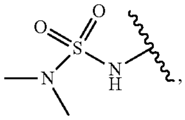,
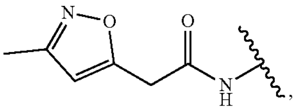,
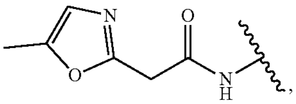,
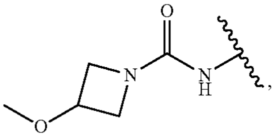,
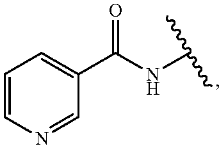,
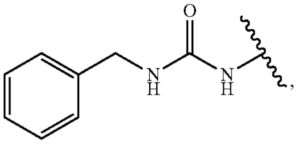,
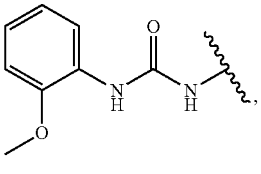,
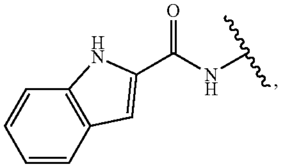,
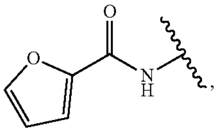,
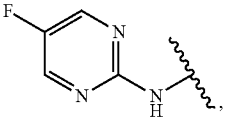,
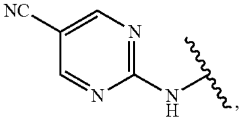,
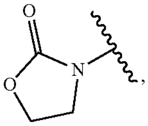,
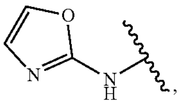,
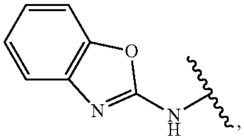,
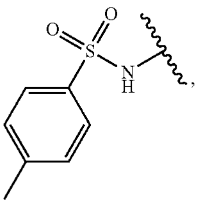,
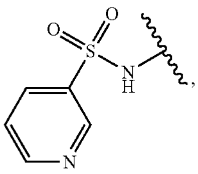,
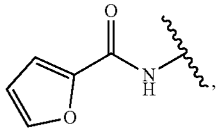,
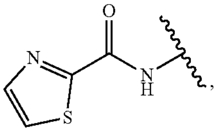,
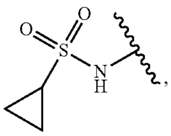,
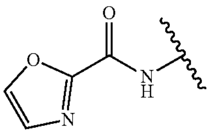, and
-continued
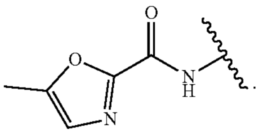.
9. The compound, the stereoisomer thereof or the pharmaceutically acceptable salt thereof according to claim 4, wherein
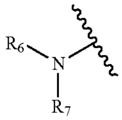
is selected from the group consisting of
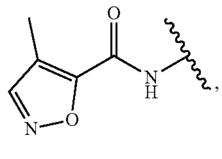,
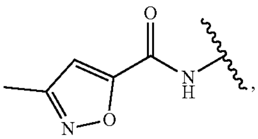,
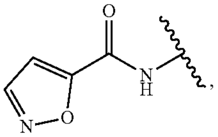,
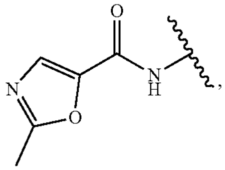,
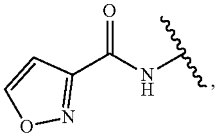,
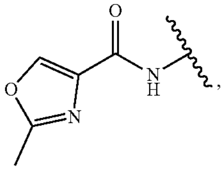,
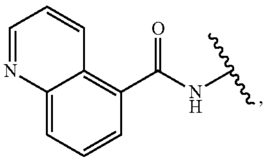,
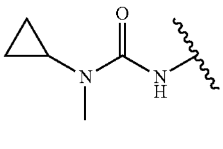 and
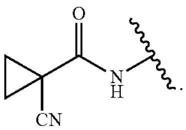.
10. The compound, the stereoisomer thereof or the pharmaceutically acceptable salt thereof according to claim 4, wherein the compound is as shown in formula (XII):

(XII)

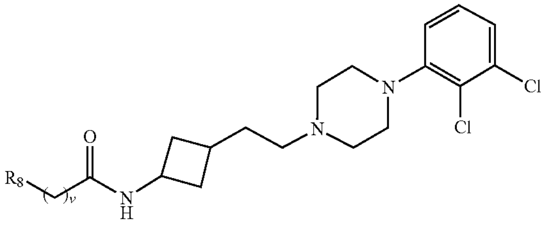

wherein:

$R_8$ is selected from the group consisting of hydrogen, deuterium, halogen, amino, nitro, hydroxy, cyano, $C_{1-6}$ alkyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl, wherein the amino, $C_{1-6}$ alkyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl are each optionally further substituted by one or more substituents selected from the group consisting of deuterium, halogen, amino, nitro, hydroxy, cyano, $C_{1-6}$ alkyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{2-6}$ alkenyl, $C_{2-6}$ alkynyl, $C_{3-8}$ cycloalkyl, 3 to 8 membered heterocyclyl, $C_{6-12}$ aryl and 5 to 12 membered heteroaryl; and v is 0 or 1;

when v is 0, then $R_8$ is not $—C_2H_5$, $—N(CH_3)_2$, $—NHCH_3$, $—NC_2H_5CH_3$, $—NHC_2H_5$

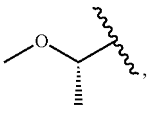,
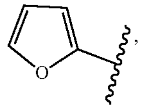,
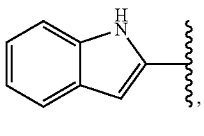,
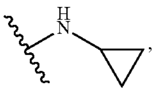,
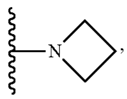,
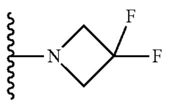 and
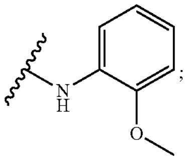;

when v is 1, then $R_8$ is not phenyl.

11. The compound, the stereoisomer thereof or the pharmaceutically acceptable salt thereof according to claim 10, wherein the compound of formula (XII) is as shown in formula (XII-A) or formula (XII-B):

(XII-A)

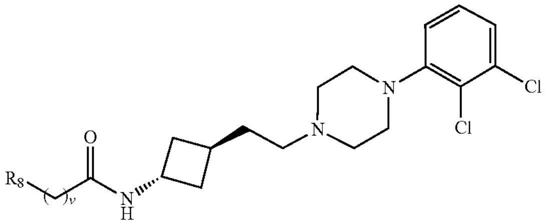 or (XII-B)

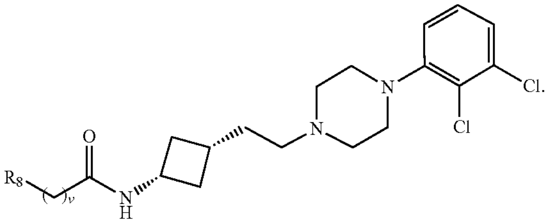

12. The compound, the stereoisomer thereof or the pharmaceutically acceptable salt thereof according to claim 1, wherein, $R_4$ is

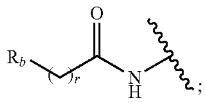;

$R_b$ is selected from the group consisting of $C_{3-6}$ cycloalkyl and 5 to 10 membered heteroaryl containing 1 to 2 nitrogen, oxygen, sulfur atoms, optionally further substituted by one or more substituents selected from the group consisting of deuterium, halogen, amino, hydroxy, $C_{1-3}$ alkyl, $C_{1-3}$ haloalkyl, $C_{1-3}$ alkoxy and $C_{1-3}$ haloalkoxy;

$R_5$ is selected from the group consisting of hydrogen, halogen and $C_{1-3}$ alkyl;

m is 1;

t is 1, 2 or 3; and when r is 0 and $R_b$ is

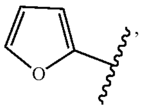 [SMILES: *c1ccco1], then $R_b$ is substituted by at least one substituent; or when r is 0 and $R_b$ is

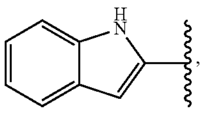 [SMILES: *c1cc2ccccc2[nH]1], then $R_b$ is substituted by at least one substituent.

13. The compound, the stereoisomer thereof or the pharmaceutically acceptable salt thereof according to claim 12, wherein $R_b$ is selected from the group consisting of $C_{3-6}$ cycloalkyl, 5 to 6 membered heteroaryl containing nitrogen or oxygen and 9 to 10 membered fused heteroaryl containing nitrogen, optionally further substituted by one or more substituents selected from the group consisting of deuterium, halogen, $C_{1-3}$ alkyl, $C_{1-3}$ haloalkyl, $C_{1-3}$ alkoxy and $C_{1-3}$ haloalkoxy.

14. The compound, the stereoisomer thereof or the pharmaceutically acceptable salt thereof according to claim 1, wherein the specific structure of the compound is as follows:

7

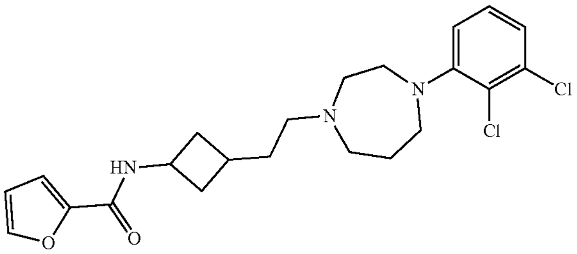

7A

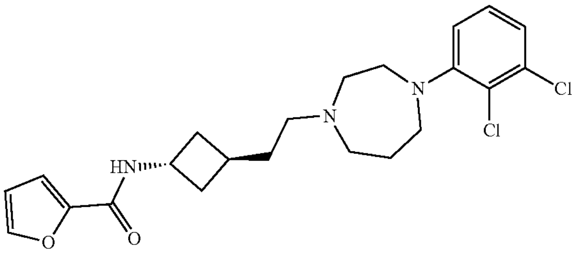

7B

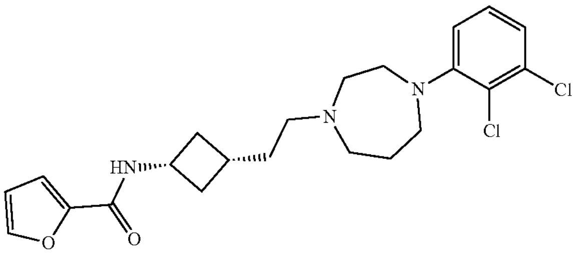

8

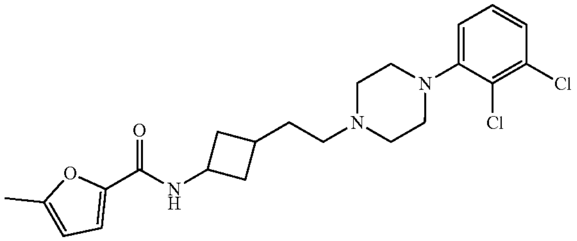

8A

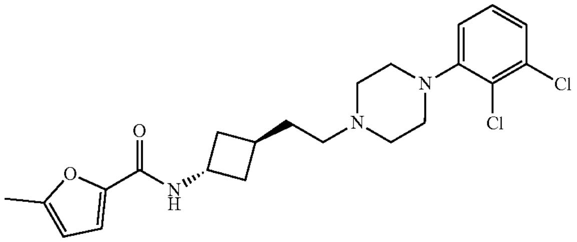

-continued

8B

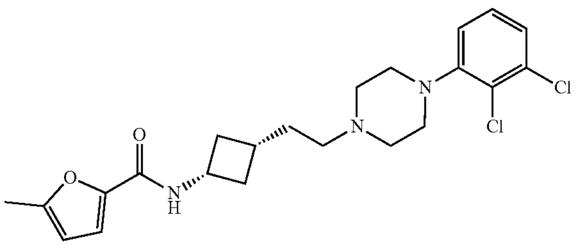

9

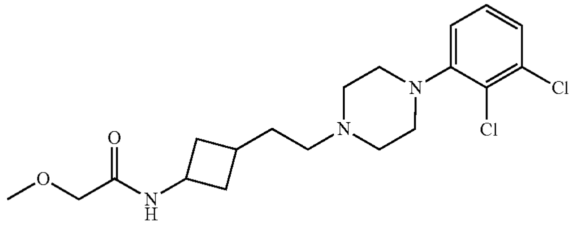

9A

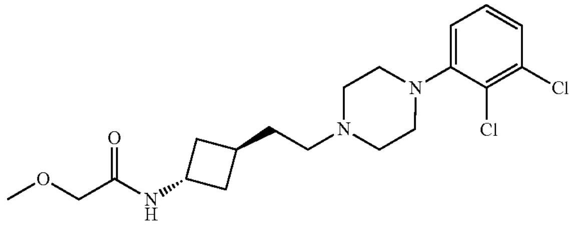

9B

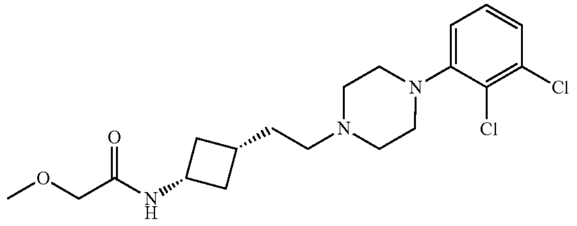

10

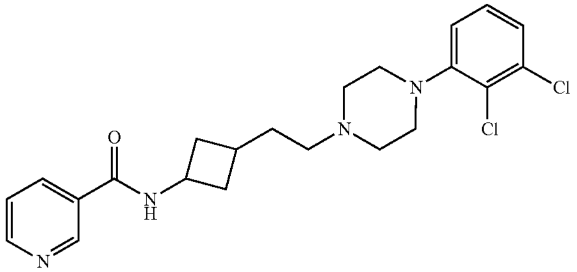

10A

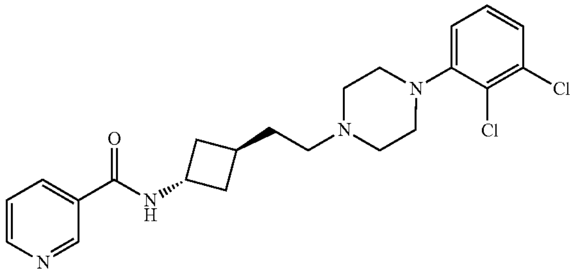

-continued
10B
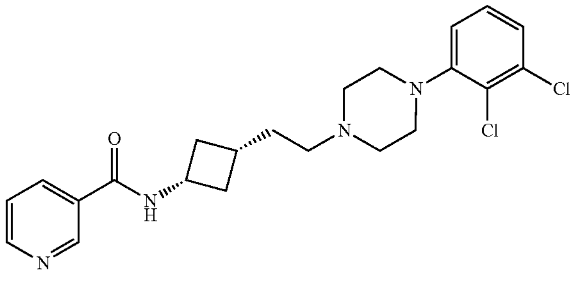
11
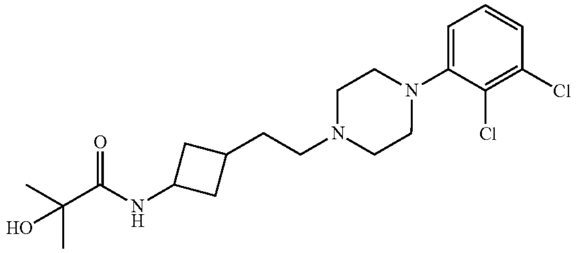
11A
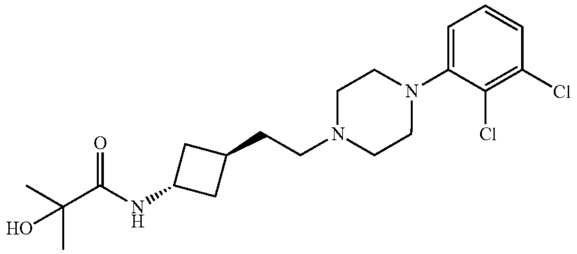
11B
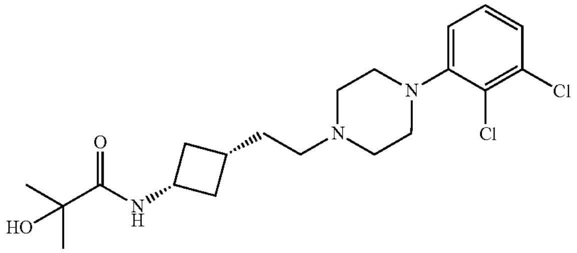
12
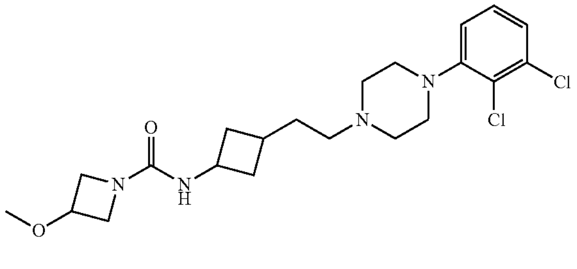
-continued
12A
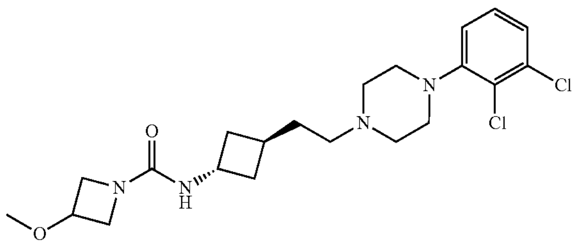
12B
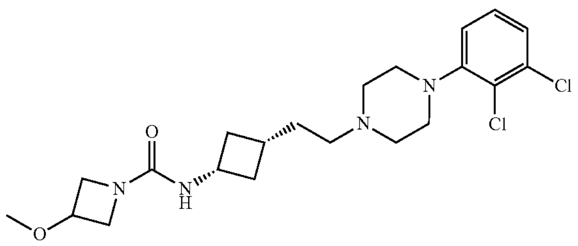
13
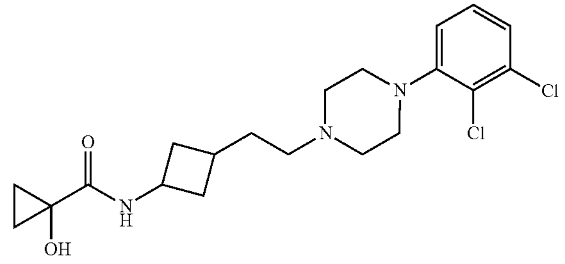
13A
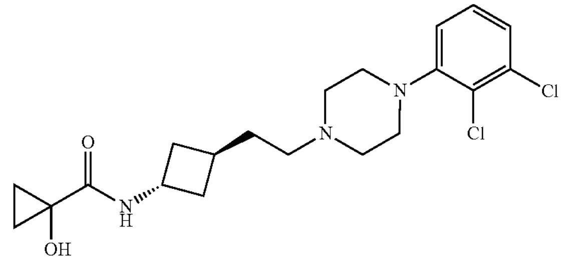
13B
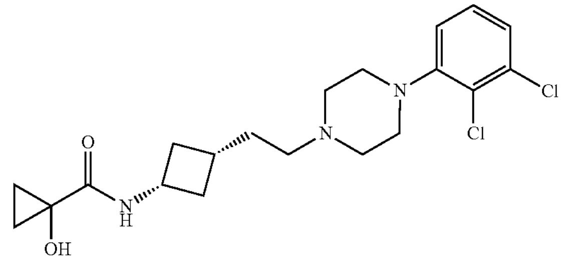

14
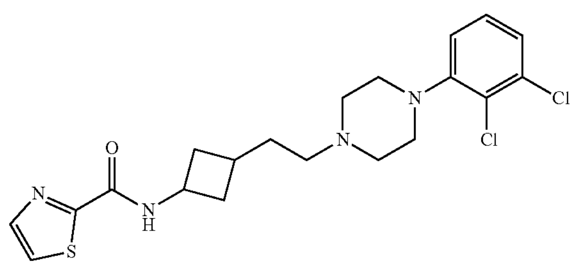
14A
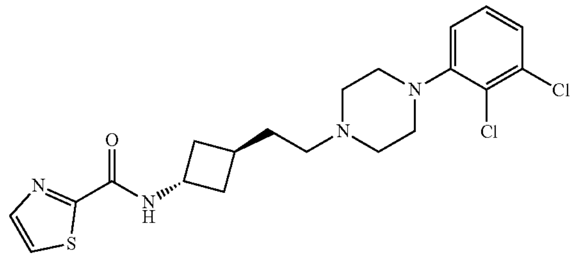
14B
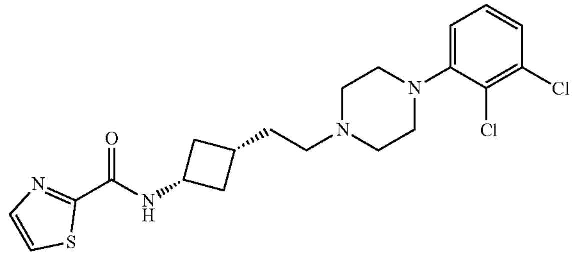
15
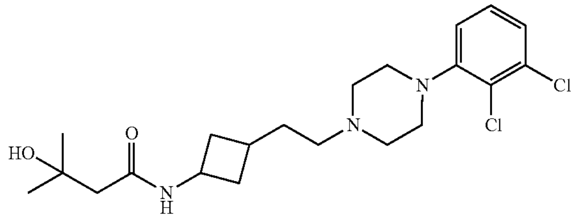
15A
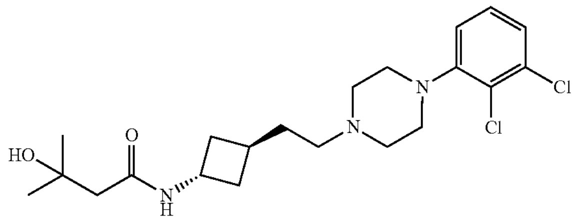
15B
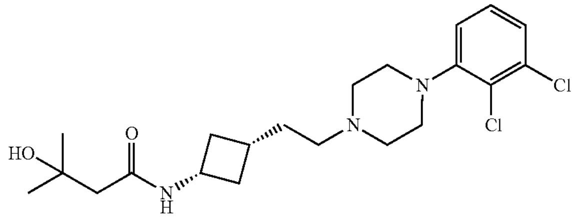
16
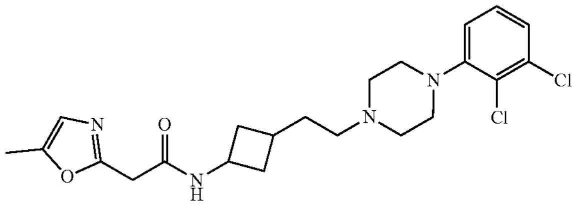
16A
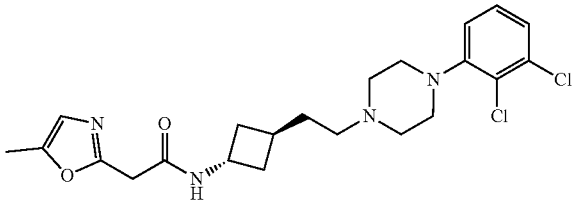
16B
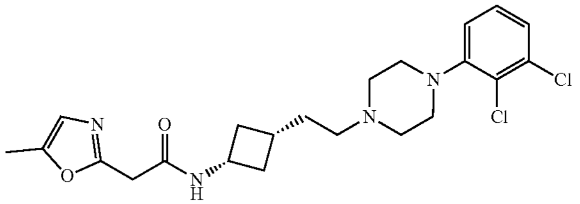
17
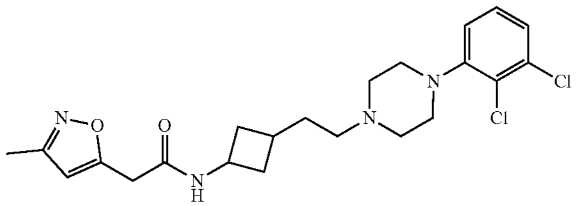
17A
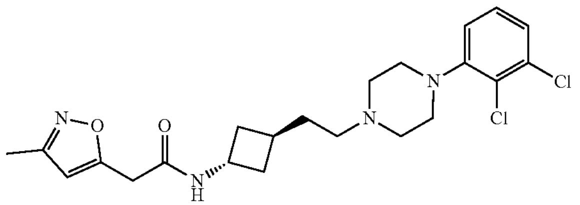
17B
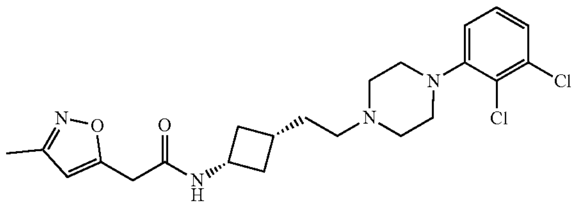

-continued
18
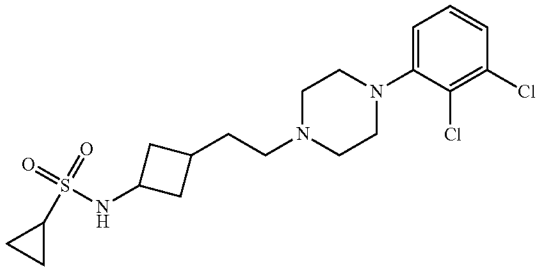
18A
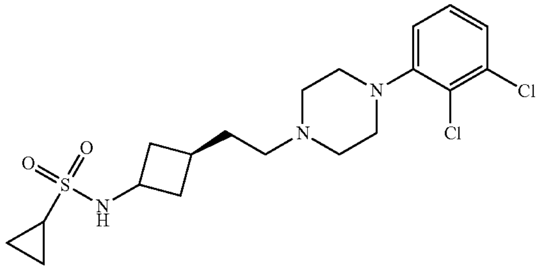
18B
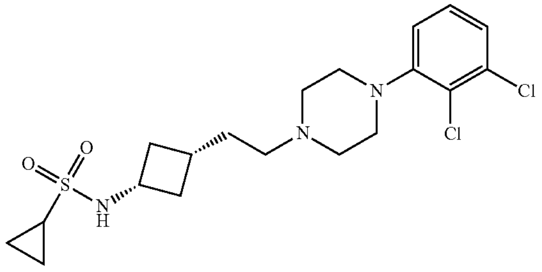
19
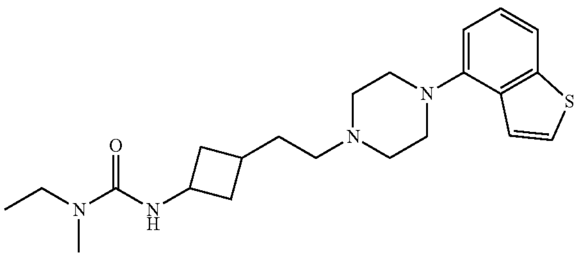
19A
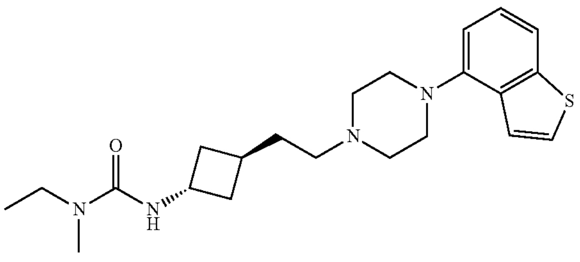
-continued
19B
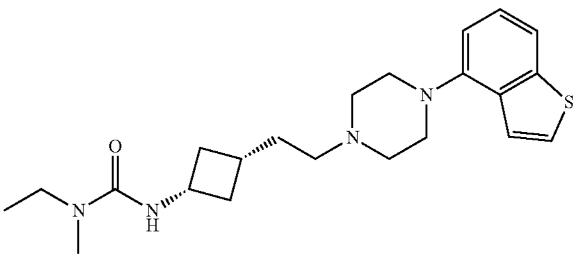
20
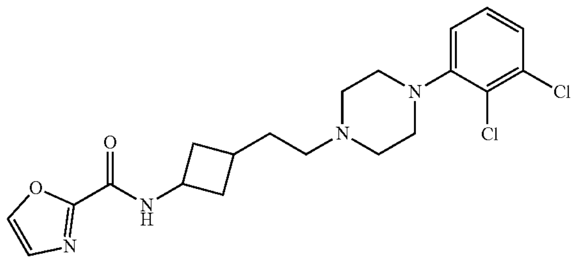
20A
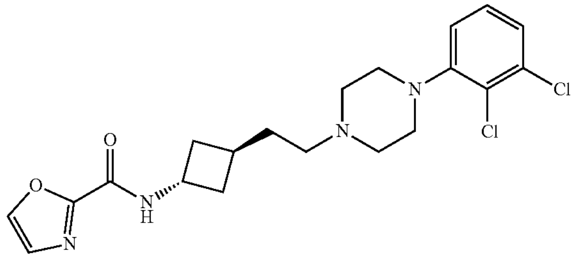
20B
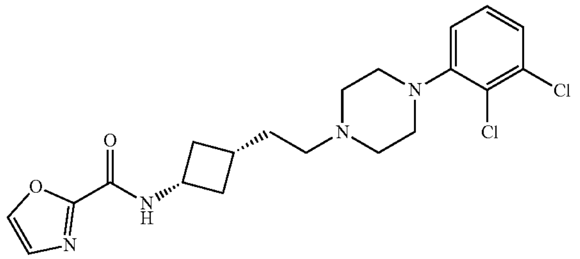
21
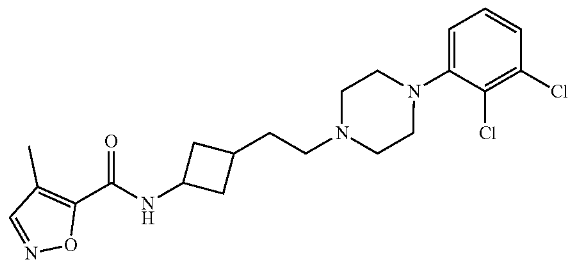

-continued
21A
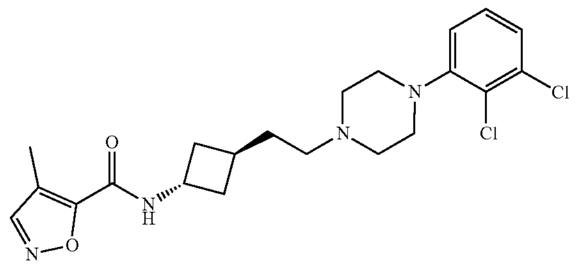
21B
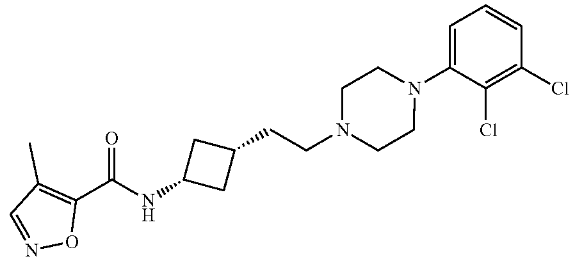
22
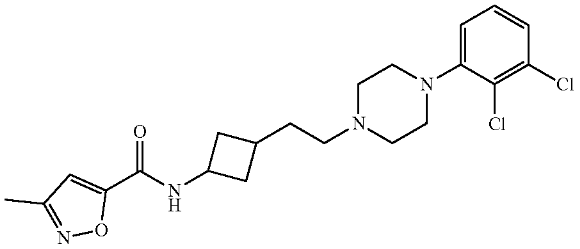
22A
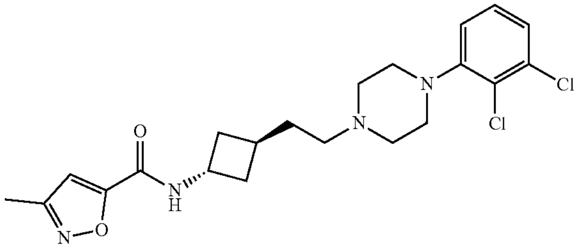
22B
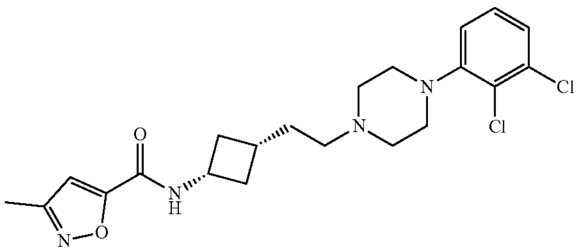
-continued
23
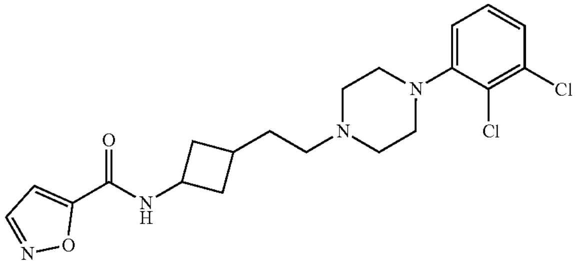
23A
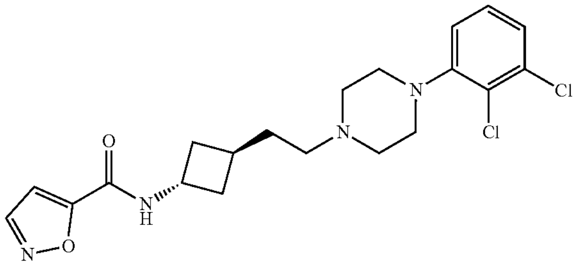
23B
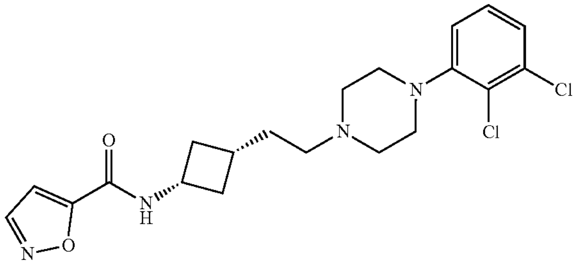
24
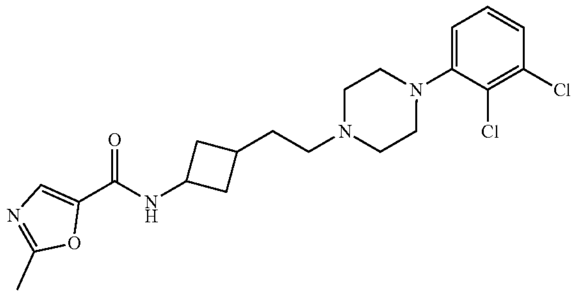
24A
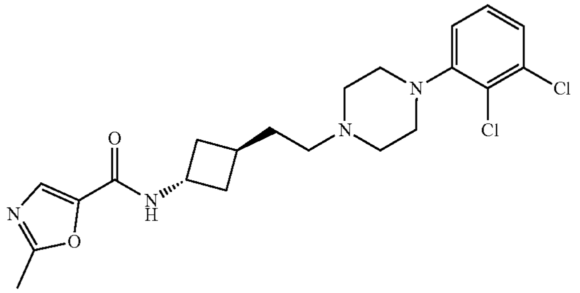

-continued
24B
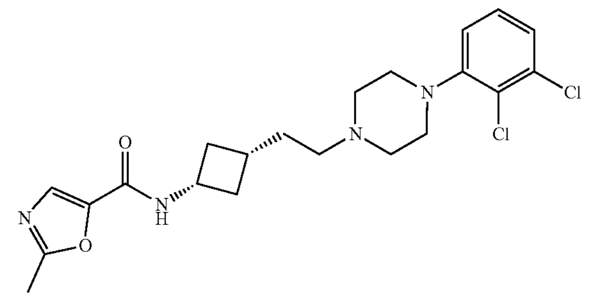
25
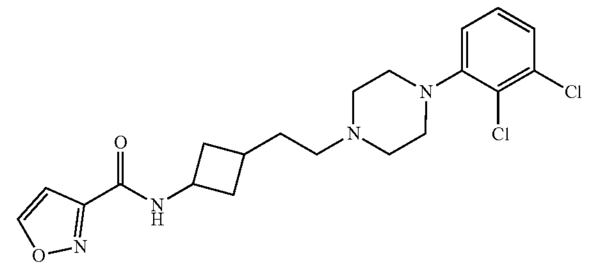
25A
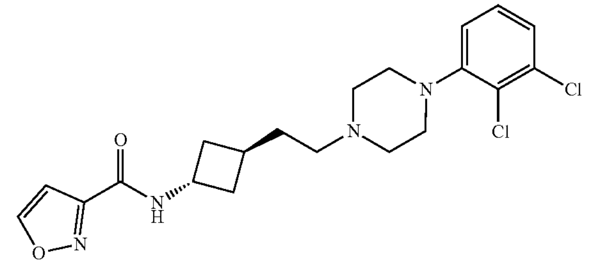
25B
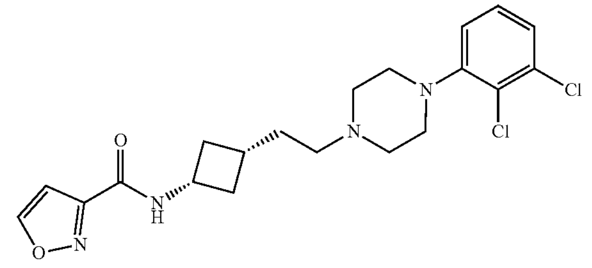
26
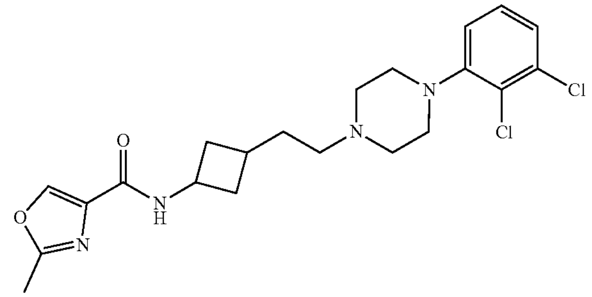
-continued
26A
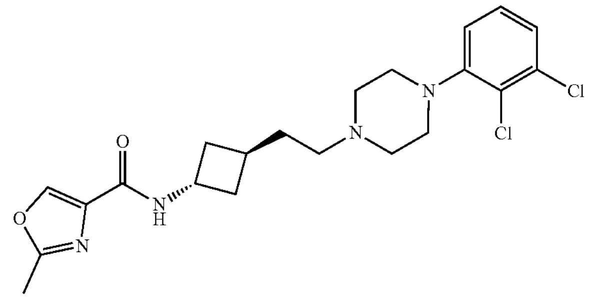
26B
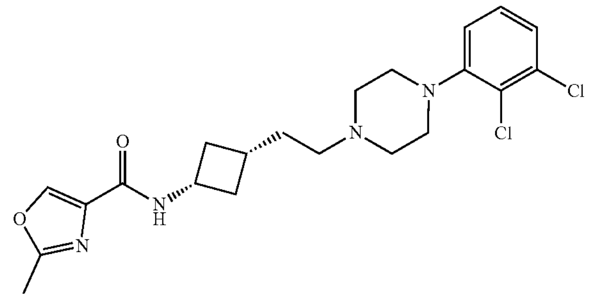
27
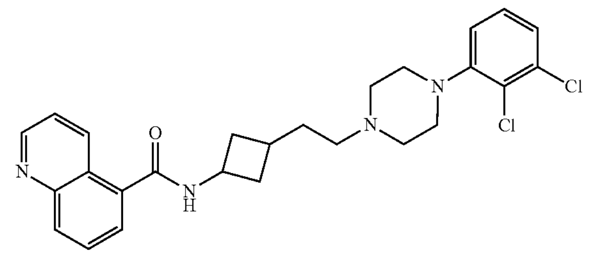
27A
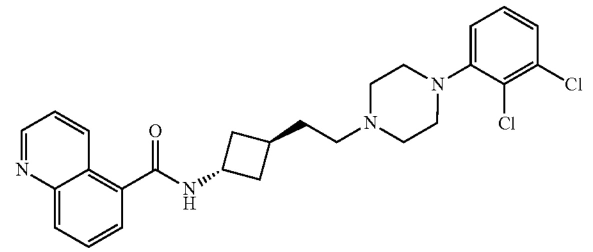
27B
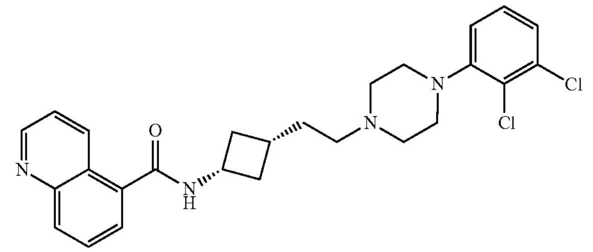

-continued
28
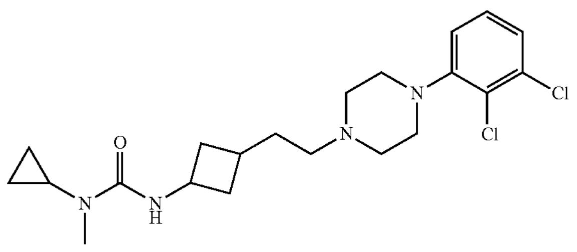
28A
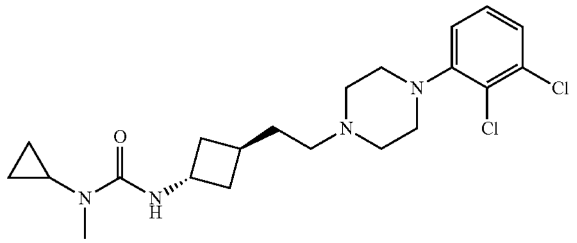
28B
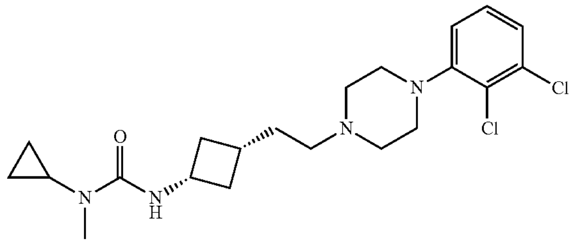
29
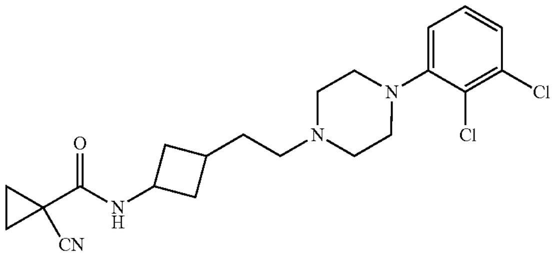
29A
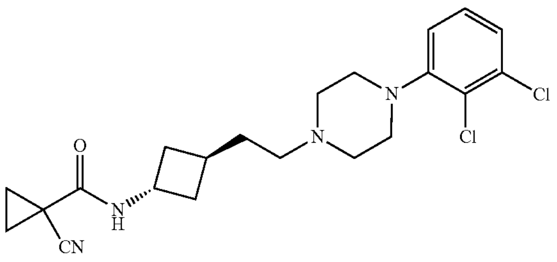
-continued
29B
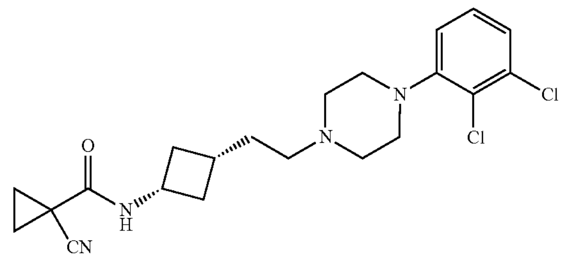
30
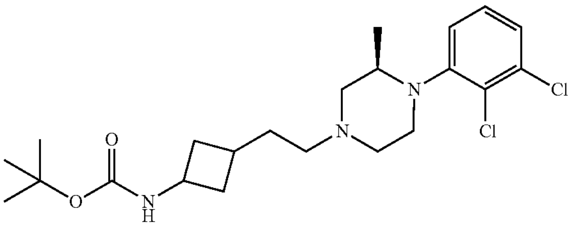
30A
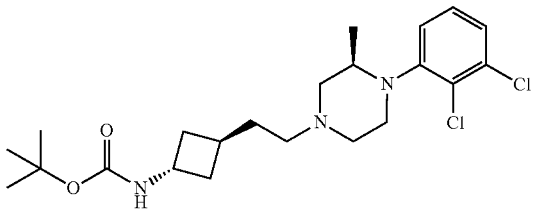
or
30B
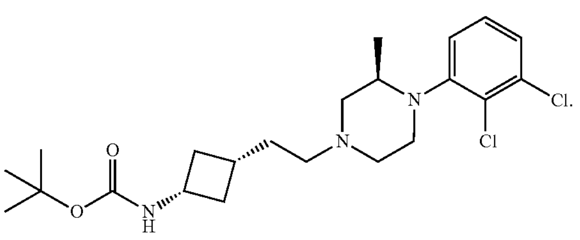
15. A method for preparing the compound of formula (XII), the stereoisomer thereof or the pharmaceutically acceptable salt thereof according to claim 10, comprising the following step of,

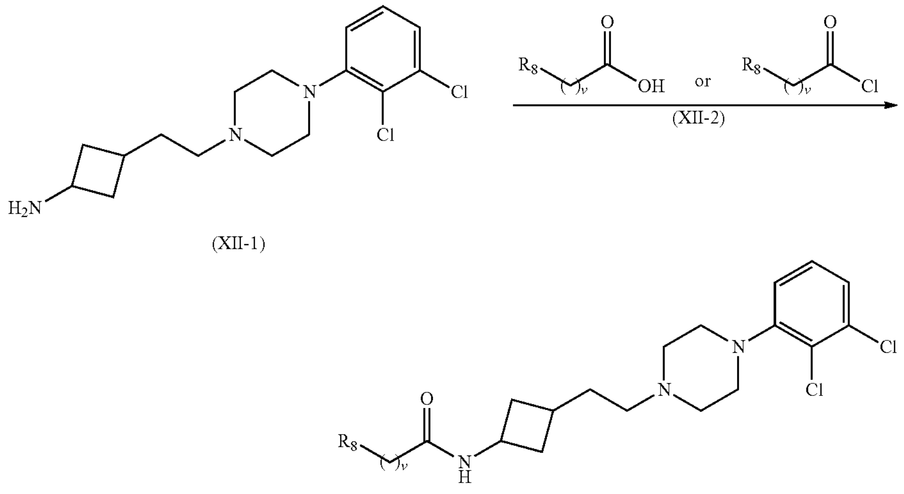

(XII-1)
(XII)

reacting a compound of formula (XII-1) with an acyl chloride or carboxylic acid of formula (XII-2) to obtain the compound of formula (XII), the stereoisomer thereof or the pharmaceutically acceptable salt thereof.

16. A compound of formula (XII-1), a stereoisomer thereof or a pharmaceutically acceptable salt thereof, (XII-1)

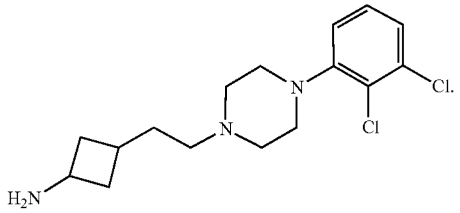

17. A method for preparing the compound of formula (XII-1), the stereoisomer thereof or the pharmaceutically acceptable salt thereof according to claim 16, comprising the following step of,

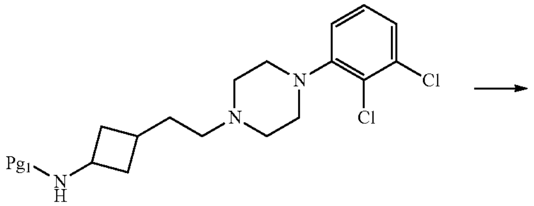
(XII-3)

-continued

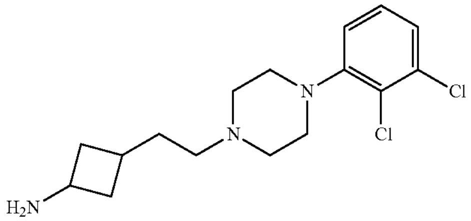
(XII-1)

deprotecting a compound of formula (XII-3) to obtain the compound of formula (XII-1), the stereoisomer thereof or the pharmaceutically acceptable salt thereof;

wherein:

$Pg_1$ is an amino protecting group, selected from the group consisting of allyloxycarbonyl, trifluoroacetyl 2,4-dimethoxybenzyl, nitrobenzenesulfonyl, trityl, fluorenemethoxycarbonyl, p-toluenesulfonyl, formate, acetyl, benzyloxycarbonyl, tert-butoxycarbonyl, benzyl and p-methoxyphenyl;

optionally, reacting a compound of formula (XII-4) with a compound of formula (XII-5) to obtain the compound of formula (XII-3), the stereoisomer thereof or the pharmaceutically acceptable salt thereof;

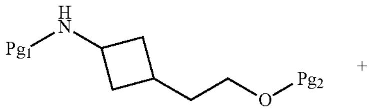
(XII-4)

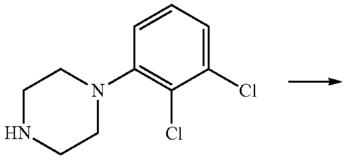
(XII-5)

-continued

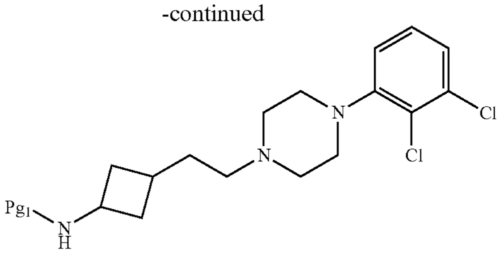

(XII-3)

$Pg_2$ is a hydroxy protecting group, selected from the group consisting of methyl, tert-butyl, triphenyl, methylthiomethyl ether, 2-methoxyethoxymethyl ether, methoxymethyl ether, p-methoxybenzyl ether, pivaloyl, benzyl ether group, methoxymethyl, trimethylsilyl, tetrahydrofuranyl, tert-butyldisilyl, acetyl, benzoyl and p-toluenesulfonyl.

18. A pharmaceutical composition, comprising a therapeutically effective dose of the compound, the stereoisomer thereof or the pharmaceutically acceptable salt thereof according to claim 1, and one or more pharmaceutically acceptable carriers, diluents or excipients.

19. A method of treating a disease or disorder mediated by a G protein-coupled receptor modulator, comprising administering to a subject in need thereof a therapeutically effective amount of the compound, the stereoisomer thereof or the pharmaceutically acceptable salt thereof according to claim 1.

20. A method of treating a central nervous system disease or psychiatric disease or disorder, comprising administering to a subject in need thereof a therapeutically effective amount of the compound, the stereoisomer thereof, or the pharmaceutically acceptable salt thereof according to claim 1.

* * * * *